(12) United States Patent
Ahmed et al.

(10) Patent No.: US 8,324,254 B2
(45) Date of Patent: Dec. 4, 2012

(54) OXADIAZOLE SUBSTITUTED INDAZOLE DERIVATIVES FOR USE AS SPHINGOSINE 1-PHOSPHATE (S1P) AGONISTS

(75) Inventors: Mahmood Ahmed, Singapore (SG); Gerard Martin Paul Giblin, Harlow (GB); James Myatt, Harlow (GB); David Norton, Harlow (GB); Dean Andrew Rivers, Singapore (SG)

(73) Assignee: Glaxo Group Limited, Greenford, Middlesex (GB)

( * ) Notice: Subject to any disclaimer, the term of this patent is extended or adjusted under 35 U.S.C. 154(b) by 464 days.

(21) Appl. No.: 12/596,488

(22) PCT Filed: Apr. 17, 2008

(86) PCT No.: PCT/EP2008/054647
§ 371 (c)(1), (2), (4) Date: Oct. 19, 2009

(87) PCT Pub. No.: WO2008/128951
PCT Pub. Date: Oct. 30, 2008

(65) Prior Publication Data
US 2010/0113528 A1 May 6, 2010

(30) Foreign Application Priority Data

Apr. 19, 2007 (GB) .................................. 0707617.7
Apr. 2, 2008 (GB) .................................. 0805993.3

(51) Int. Cl.
| | | |
|---|---|---|
| *A01N 43/40* | (2006.01) | |
| *A61K 31/44* | (2006.01) | |
| *C07D 271/06* | (2006.01) | |
| *C07D 271/12* | (2006.01) | |
| *C07D 413/00* | (2006.01) | |
| *C07D 498/00* | (2006.01) | |
| *C07D 413/04* | (2006.01) | |
| *C07D 413/14* | (2006.01) | |

(52) U.S. Cl. ...... 514/338; 514/364; 548/131; 546/269.4
(58) Field of Classification Search ................... 514/338, 514/364; 546/269.4; 548/131
See application file for complete search history.

(56) References Cited

U.S. PATENT DOCUMENTS

| | | | |
|---|---|---|---|
| 5,137,898 A | 8/1992 | Klausener et al. |
| 5,182,286 A | 1/1993 | Seitz et al. |
| 5,262,416 A | 11/1993 | Seitz et al. |
| 5,462,943 A | 10/1995 | Seitz et al. |
| 5,514,692 A | 5/1996 | Aldous et al. |
| 5,523,312 A | 6/1996 | Aldous et al. |
| 7,199,142 B2 | 4/2007 | Chen et al. |
| 2002/0102279 A1 | 8/2002 | Chiba et al. |
| 2005/0245575 A1 | 11/2005 | Chen et al. |
| 2008/0113961 A1 | 5/2008 | Nishi et al. |
| 2008/0188532 A1 | 8/2008 | Takeuchi et al. |
| 2008/0249093 A1 | 10/2008 | Colandrea et al. |
| 2008/0306124 A1 | 12/2008 | Albert et al. |
| 2008/0318855 A1 | 12/2008 | Bolli et al. |
| 2009/0042954 A1 | 2/2009 | Hale et al. |
| 2009/0076070 A1 | 3/2009 | Harada et al. |
| 2009/0221547 A1 | 9/2009 | Gao et al. |

FOREIGN PATENT DOCUMENTS
WO WO2008/074821 12/2007

OTHER PUBLICATIONS

Szczucinski et al. Acta Neurol. Scand. Published online Oct. 2006, pp. 137-146.*
Allende, et al 2003 102:3665, Blood.
Brinkman, et al 2002 JBC 277:21453.
Brinkman, et al 2004 American J Transplantation, 4:1019.
Chiba, et al 1998, J Immunology 160:5037.
Chiba 2005 Pharmacology and Therapeutics 108:308.
Chun et al 2002 Pharmacological Reviews 54:265.
Forrest, et al 2004 J Pharmacol Exp Ther 309:758.
Fujino, et al 2003 J Pharmacol Exp Ther 305:70.
Graler and Goetzl 2004 Faseb J 18:551.
Hale, et al 2004 Bioorganic & Medicinal Chemistry Letters 14:3501.
Jo, et al 2005 Chem Biol 12:703.
Kluk and Hla 2002 Biochem et Biophysica Acta 1582:72.
Kahan, et al 2003, Transplanation 76:1079.
Kappos, et al 2006 New Eng J Medicine 355:1124.
Koyrakh, et al 2005 American J Transplantation 5:529.
Mandala, et al 2002 Science 296:346.
Matloubian, et al 2004 Nature 427:355.
Morris, et al 2005 EurJ Immunol 35:3570.
Okamoto, et al 1998 J Biol Chem 273(42):27104.
Pyne and Pyne 2000, Biochem J. 349:385.
Rausch, et al 2004 J Magn Reson Imaging 20:16.
Rosen and Goetzl 2005 Nat Rev Immunol, 5:560.
Sanchez and Hla 2004, J Cell Biochem 92:913.
Sanna, et al 2004 JBC 279:13839.
Singelton, et al 2005 FASEB J 19:1646.
Webb, et al 2004 J Neuroimmunol 153:108.
Wei, et al 2005, Nat. Immunology 6:1228.

* cited by examiner

*Primary Examiner* — Samira Jean-Louis
(74) *Attorney, Agent, or Firm* — Linda E. Hall; John L. Lemanowicz

(57) ABSTRACT

The present invention provides compounds of formula (I) or salts thereof:

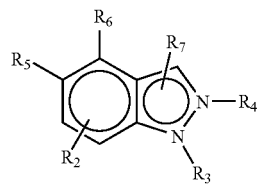

(I)

having pharmacological activity, processes for their preparation, pharmaceutical compositions containing them and their use in the treatment of various disorders mediated by S1P1 receptors.

7 Claims, No Drawings

OXADIAZOLE SUBSTITUTED INDAZOLE DERIVATIVES FOR USE AS SPHINGOSINE 1-PHOSPHATE (S1P) AGONISTS

This application is a 371 of International Application No. PCT/EP2008/054647, filed Apr. 17, 2008, which claims the priority of GB0707617.7, filed Apr. 19, 2007, which are incorporated herein in their entirety.

The present invention relates to novel oxadiazole derivatives having pharmacological activity, processes for their preparation, pharmaceutical compositions containing them and their use in the treatment of various disorders.

Sphingosine 1-phosphate (S1P) is a bioactive lipid mediator formed by the phosphorylation of sphingosine by sphingosine kinases and is found in high levels in the blood. It is produced and secreted by a number of cell types, including those of hematopoietic origin such as platelets and mast cells (Okamoto et al 1998 J Biol Chem 273(42):27104; Sanchez and Hla 2004, J Cell Biochem 92:913). It has a wide range of biological actions, including regulation of cell proliferation, differentiation, motility, vascularisation, and activation of inflammatory cells and platelets (Pyne and Pyne 2000, Biochem J. 349: 385). Five subtypes of S1P responsive receptor have been described, S1P1 (Edg-1), S1P2 (Edg-5), S1P3 (Edg-3), S1P4 (Edg-6), and S1P5 (Edg-8), forming part of the G-protein coupled endothelial differentiation gene family of receptors (Chun et al 2002 Pharmacological Reviews 54:265, Sanchez and Hla 2004 J Cellular Biochemistry, 92:913). These 5 receptors show differential mRNA expression, with S1P1-3 being widely expressed, S1P4 expressed on lymphoid and hematopoietic tissues and S1P5 primarily in brain and to a lower degree in spleen. They signal via different subsets of G proteins to promote a variety of biological responses (Kluk and Hla 2002 Biochem et Biophysica Acta 1582:72, Sanchez and Hla 2004, J Cellular Biochem 92:913).

Proposed roles for the S1P1 receptor include lymphocyte trafficking, cytokine induction/suppression and effects on endothelial cells (Rosen and Goetzl 2005 Nat Rev Immunol. 5:560). Agonists of the S1P1 receptor have been used in a number of autoimmune and transplantation animal models, including Experimental Autoimmune Encephalomelitis (EAE) models of MS, to reduce the severity of the induced disease (Brinkman et al 2003 JBC 277:21453; Fujino et al 2003 J Pharmacol Exp Ther 305:70; Webb et al 2004 J Neuroimmunol 153:108; Rausch et al 2004 J Magn Reson Imaging 20:16). This activity is reported to be mediated by the effect of S1P1 agonists on lymphocyte circulation through the lymph system. Treatment with S1P1 agonists results in the sequestration of lymphocytes within secondary lymphoid organs such as the lymph nodes, inducing a reversible peripheral lymphopoenia in animal models (Chiba et al 1998, J Immunology 160:5037, Forrest et al 2004 J Pharmacol Exp Ther 309:758; Sanna et al 2004 JBC 279:13839). Published data on agonists suggests that compound treatment induces loss of the S1P1 receptor from the cell surface via internalisation (Graler and Goetzl 2004 FASEB J 18:551; Matloubian et al 2004 Nature 427:355; Jo et al 2005 Chem Biol 12:703) and it is this reduction of S1P1 receptor on immune cells which contributes to the reduction of movement of T cells from the lymph nodes back into the blood stream.

S1P1 gene deletion causes embryonic lethality. Experiments to examine the role of the S1P1 receptor in lymphocyte migration and trafficking have included the adoptive transfer of labelled S1P1 deficient T cells into irradiated wild type mice. These cells showed a reduced egress from secondary lymphoid organs (Matloubian et al 2004 Nature 427:355).

S1P1 has also been ascribed a role in endothelial cell junction modulation (Allende et al 2003 102:3665, Blood Singelton et al 2005 FASEB J 19:1646). With respect to this endothelial action, S1P1 agonists have been reported to have an effect on isolated lymph nodes which may be contributing to a role in modulating immune disorders. S1P1 agonists caused a closing of the endothelial stromal 'gates' of lymphatic sinuses which drain the lymph nodes and prevent lymphocyte egress (Wei et al 2005, Nat. Immunology 6:1228).

The immunosuppressive compound FTY720 (JP11080026-A) has been shown to reduce circulating lymphocytes in animals and man, have disease modulating activity in animal models of immune disorders and reduce remission rates in relapsing remitting Multiple Sclerosis (Brinkman et al 2002 JBC 277:21453, Mandala et al 2002 Science 296:346, Fujino et al 2003 J Pharmacology and Experimental Therapeutics 305:45658, Brinkman et al 2004 American J Transplantation 4:1019, Webb et al 2004 J Neuroimmunology 153:108, Morris et al 2005 Eur J Immunol 35:3570, Chiba 2005 Pharmacology and Therapeutics 108: 308, Kahan et al 2003, Transplantation 76:1079, Kappos et al 2006 New Eng J Medicine 335:1124). This compound is a prodrug that is phosphorylated in vivo by sphingosine kinases to give a molecule that has agonist activity at the S1P1, S1P3, S1P4 and S1P5 receptors. Clinical studies have demonstrated that treatment with FTY720 results in bradycardia in the first 24 hours of treatment (Kappos et al 2006 New Eng J Medicine 335:1124). The bradycardia is thought to be due to agonism at the S1P3 receptor, based on a number of cell based and animal experiments. These include the use of S1P3 knock-out animals which, unlike wild type mice, do not demonstrate bradycardia following FTY720 administration and the use of S1P1 selective compounds. (Hale et al 2004 Bioorganic & Medicinal Chemistry Letters 14:3501, Sanna et al 2004 JBC 279: 13839, Koyrakh et al 2005 American J Transplantation 5:529)

The following patent applications describe oxadiazole derivatives as S1P1 agonists: WO03/105771, WO05/058848, WO06/047195, WO06/100633, WO06/115188 and WO06/131336.

The following patent application describes indole-oxadiazole derivatives as antipicornaviral agents: WO96/009822. The following patent applications describe indole-carboxylic acid derivatives as leukotriene receptor antagonists, pesticides and agrochemical fungicides respectively: WO06/090817, EP 0 439 785 and DE 39 39 238.

International patent application WO06/001463 discloses various compounds as agonists of the S1P1 receptor.

International patent application PCT/EP2007/064185 discloses indole-oxadiazole compounds as agonists of the S1P1 receptor.

A structurally novel class of compounds has now been found which provides agonists of the S1P1 receptor.

The present invention therefore provides compounds of formula (I) or a salt thereof:

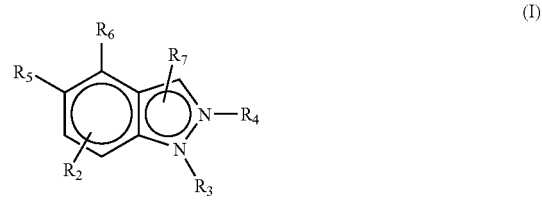

(I)

wherein
one of $R_5$ and $R_6$ is hydrogen or $R_2$ and the other is (a)

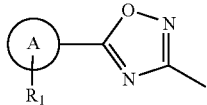
(a)

one of $R_3$ and $R_4$ is (b)

(b)

A is a phenyl or a 5 or 6-membered heteroaryl ring;
$R_1$ is hydrogen or up to three substituents independently selected from halogen, $C_{(1-4)}$alkyl, $C_{(1-4)}$alkoxy, $C_{(5-7)}$cycloalkyl, $C_{(5-7)}$cycloalkoxy, trifluoromethoxy, difluoromethoxy, trifluoromethyl, cyano, phenyl, 5 or 6 membered heteroaryl rings, piperidinyl and pyrrolidinyl;
$R_2$ is hydrogen or up to three substituents independently selected from halogen, $C_{(1-4)}$alkyl, $C_{(1-4)}$alkoxy, trifluoromethoxy, difluoromethoxy, trifluoromethyl and cyano;
$R_7$ is hydrogen or halogen;
Z is $C_{(1-4)}$alkyl may be optionally interrupted once by N or O and may be optionally substituted on carbon by up to four substituents independently selected from halogen, methyl and hydroxyl, with the proviso that no carbon atom is substituted by two hydroxyl groups.

The present invention therefore provides compounds of formula (IA) or salts thereof:

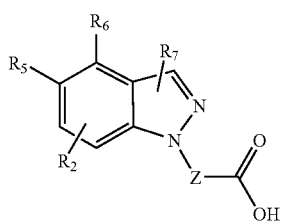
(IA)

wherein A, $R_1$, $R_2$, $R_5$, $R_6$, $R_7$ and Z are as defined for formula (I).

The present invention therefore provides compounds of formula (IB) or salts thereof:

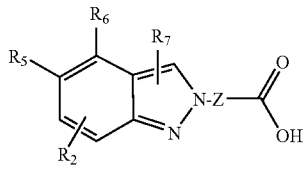
(IB)

wherein A, $R_1$, $R_2$, $R_5$, $R_6$, $R_7$ and Z are as defined for formula (I).

The present invention therefore provides compounds of formula (II) or pharmaceutically acceptable derivatives thereof:

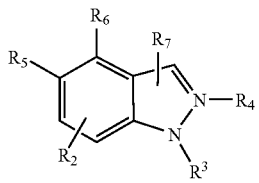
(II)

wherein
one of $R_5$ and $R_6$ is hydrogen or $R_2$ and the other is (a)

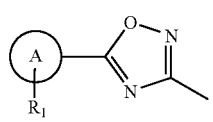
(a)

one of $R_3$ and $R_4$ is hydrogen and the other is (b)

(b)

A is a phenyl or a 5 or 6-membered heteroaryl ring;
$R_1$ is hydrogen or up to three substituents independently selected from halogen, $C_{(1-4)}$alkyl, $C_{(1-4)}$alkoxy, trifluoromethoxy, difluoromethoxy, trifluoromethyl, cyano, and optionally substituted phenyl or optionally substituted 5 or 6 membered heteroaryl rings;
$R_2$ is hydrogen or up to three substituents independently selected from halogen, $C_{(1-4)}$alkyl, $C_{(1-4)}$alkoxy, trifluoromethoxy, difluoromethoxy, trifluoromethyl and cyano;
$R_7$ is hydrogen or halogen;
Z is $C_{(1-4)}$alkyl which is optionally interrupted by N or O and is optionally substituted by halogen or methyl.

When $R_1$ is phenyl or a 5 or 6 membered heteroaryl ring it may be substituted by up to three substituents selected from halogen, $C_{(1-4)}$alkyl, $C_{(1-4)}$alkoxy, trifluoromethoxy, difluoromethoxy, trifluoromethyl and cyano.

It will be appreciated that for compounds of formula (II), when $R_4$ is (b) $R_3$ will not be present and the bonds in the aromatic rings will be arranged as depicted in formula (IB) described above.

The term "alkyl" as a group or part of a group e.g. alkoxy or hydroxyalkyl refers to a straight or branched alkyl group in all isomeric forms. The term "$C_{(1-4)}$alkyl" refers to an alkyl group, as defined above, containing at least 1, and at most 4 carbon atoms Examples of such alkyl groups include methyl, ethyl, propyl, iso-propyl, n-butyl, iso-butyl, sec-butyl, tert-butyl, 1-methylpropyl or 2-methylpropyl Examples of such alkoxy groups include methoxy, ethoxy, propoxy, iso-propoxy, butoxy, iso-butoxy, sec-butoxy, tert-butoxy, or 1-methylpropoxy.

Suitable $C_{(5-7)}$cycloalkyl groups include cyclopentyl, cyclohexyl and cycloheptyl.

Suitable $C_{(5-7)}$cycloalkyloxy groups include cyclopentoxy, cyclohexyloxy and cycloheptoxy.

As used herein, the term "halogen" refers to fluorine (F), chlorine (Cl), bromine (Br), or iodine (I) and the term "halo" refers to the halogen: fluoro (—F), chloro (—Cl), bromo (—Br) and iodo (—I).

The term "heteroaryl" represents an unsaturated ring which comprises one or more heteroatoms. When the term heteroaryl represents a 5-membered group it contains a heteroatom selected from O, N or S and may optionally contain a further 1 to 3 nitrogen atoms. When heteroaryl represents a 6-membered group it contains from 1 to 3 nitrogen atoms. Examples of such 5 or 6 membered heteroaryl rings include pyrrolyl, triazolyl, thiadiazolyl, tetrazolyl, imidazolyl, pyrazolyl, isothiazolyl, thiazolyl, isoxazolyl, oxazolyl, oxadiazolyl, furazanyl, furanyl, thienyl, pyridyl, pyrimidinyl, pyrazinyl, pyridazinyl and triazinyl.

One embodiment of the invention is a compound of formula (I) wherein
A is thiophene, pyridyl or phenyl; and
$R_1$ is two substituents independently selected from, chloro, bromo, isopropoxy, propoxy, methoxy, 1-methylpropoxy, cyano, trifluoromethyl, trifluoromethoxy, cyclohexyl, piperidine, pyrrolidinyl, ethyl, 2-methylpropyl, phenyl and cyclopentoxy; and
$R_2$ is hydrogen; and
$R_7$ is hydrogen; and
Z is ethylene or propylene, each optionally substituted by gem-dimethyl.

One embodiment of the invention is a compound of formula (I) wherein
$R_6$ is (a) and $R_5$ is hydrogen; and
A is thiophene, pyridyl or phenyl; and
$R_1$ is two substituents independently selected from chloro, bromo, isopropoxy, propoxy, methoxy, 1-methylpropoxy, cyano, trifluoromethyl, trifluoromethoxy, cyclohexyl, piperidine, pyrrolidinyl, ethyl, 2-methylpropyl, phenyl andcyclopentoxy; and
$R_2$ is hydrogen; and
$R_7$ is hydrogen; and
Z is ethylene or propylene, each optionally substituted by gem-dimethyl.

One embodiment of the invention is a compound of formula (IA) wherein
$R_6$ is (a) and $R_5$ is hydrogen; and
A is phenyl; and
$R_1$ is two substituents independently selected from chloro, isopropoxy, cyano, trifluoromethyl, trifluoromethoxy, piperidine, ethyl and phenyl; and
$R_2$ is hydrogen; and
$R_7$ is hydrogen; and
Z is ethylene or propylene.

One embodiment of the invention is a compound of formula (IA) wherein
$R_6$ is (a) and $R_5$ is hydrogen; and
A is phenyl; and
$R_1$ is chloro and isopropoxy; and
$R_2$ is hydrogen; and
$R_7$ is hydrogen; and
Z is ethylene or propylene.

One embodiment of the invention is a compound of formula (IB) wherein
$R_6$ is (a) and $R_5$ is hydrogen; and
A is phenyl; and
$R_1$ is two substituents independently selected from chloro, isopropoxy and cyano; and
$R_2$ is hydrogen; and
$R_7$ is hydrogen; and
Z is ethylene or propylene.

One embodiment of the invention is a compound of formula (I) wherein
$R_5$ is (a) and $R_6$ is hydrogen; and
A is thiophene, pyridyl or phenyl; and
$R_1$ is two substituents independently selected from chloro, bromo, isopropoxy, propoxy, methoxy, 1-methylpropoxy, cyano, trifluoromethyl, trifluoromethoxy, cyclohexyl, piperidine, pyrrolidinyl, ethyl, 2-methylpropyl, phenyl and cyclopentoxy; and
$R_2$ is hydrogen; and
$R_7$ is hydrogen; and
Z is ethylene or propylene, each optionally substituted by gem-dimethyl.

One embodiment of the invention is a compound of formula (IA) wherein
$R_5$ is (a) and $R_6$ is hydrogen; and
A is phenyl; and
$R_1$ is chloro and isopropoxy; and
$R_2$ is hydrogen; and
$R_7$ is hydrogen; and
Z is ethylene.

One embodiment of the invention is a compound of formula (IB) wherein
$R_5$ is (a) and $R_6$ is hydrogen; and/or
A is phenyl; and
$R_1$ is two substituents independently selected from chloro, isopropoxy, phenyl and trifluoromethyl; and
$R_2$ is hydrogen; and
$R_7$ is hydrogen; and
Z is propylene.

In one embodiment of the invention are compounds of formula (II) wherein
$R_3$ is (b); and/or
$R_5$ is (a) and $R_6$ is hydrogen; and/or
A is optionally substituted thiophene or phenyl; and/or
$R_1$ is hydrogen, halogen, $C_{1-4}$alkoxy, or trifluoromethyl; and/or
$R_2$ is hydrogen; and/or
Z is ethylene.

In another embodiment of the invention are compounds of formula (II) wherein
$R_3$ is (b); and/or
$R_5$ is (a) and $R_6$ is hydrogen; and/or
A is thiophene substituted by phenyl; and/or
$R_1$ is hydrogen, halogen, $C_{1-4}$alkoxy, or trifluoromethyl; and/or
$R_2$ is hydrogen; and/or
Z is ethylene.

The invention extends to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

Suitable compounds of the invention are:
3-[5-(5-{3-Chloro-4-[(1-methylethyl)oxy]phenyl}-1,2,4-oxadiazol-3-yl)-1H-indazol-1-yl]propanoic acid
3-(5-{5-[3-Chloro-4-(ethyloxy)phenyl]-1,2,4-oxadiazol-3-yl}-1H-indazol-1-yl)propanoic acid
3-[5-(5-{3-Cyano-4-[(1-methylethyl)oxy]phenyl}-1,2,4-oxadiazol-3-yl)-1H-indazol-1-yl]propanoic acid
3-[5-(5-{3-Cyano-4-[(1-methylethyl)oxy]phenyl}-1,2,4-oxadiazol-3-yl)-1H-indazol-1-yl]propanoic acid
4-[5-(5-{3-Cyano-4-[(1-methylethyl)oxy]phenyl}-1,2,4-oxadiazol-3-yl)-1H-indazol-1-yl]butanoic acid
3-(5-{5-[4-[(1-Methylethyl)oxy]-3-(trifluoromethyl)phenyl]-1,2,4-oxadiazol-3-yl}-1H-indazol-1-yl)propanoic acid
4-[4-(5-{3-Chloro-4-[(1-methylethyl)oxy]phenyl}-1,2,4-oxadiazol-3-yl)-1H-indazol-1-yl]butanoic acid 4-[4-(5-{3-Chloro-4-[(1-methylethyl)oxy]phenyl}-1,2,4-oxadiazol-3-yl)-1H-indazol-1-yl]butanoic acid 3-[4-(5-{3-Chloro-4-[(1-methylethyl)oxy]phenyl}-1,2,4-oxadiazol-3-yl)-1H-indazol-1-yl]propanoic acid 3-(5-{5-[3-Chloro-4-(propyloxy)phenyl]-1,2,4-oxadiazol-3-yl}-1H-indazol-1-yl)propanoic acid 3-[5-(5-{3-Chloro-4-[(trifluoromethyl)oxy]phenyl}-1,2,4-oxadiazol-3-yl)-1H-indazol-1-yl]propanoic acid 3-(5-{5-[4-Cyclohexyl-3-(trifluoromethyl)phenyl]-1,2,4-oxadiazol-3-yl}-1H-indazol-1-yl)propanoic acid 3-(5-{5-[4-(Methyloxy)-3-(trifluoromethyl)phenyl]-1,2,4-oxadiazol-3-yl}-1H-indazol-1-yl)propanoic acid

[5-(5-{3-Cyano-4-[(1-methylethyl)oxy]phenyl}-1,2,4-oxadiazol-3-yl)-1H-indazol-1-yl]acetic acid 3-(5-{5-[3-Chloro-4-(methyloxy)phenyl]-1,2,4-oxadiazol-3-yl}-1H-indazol-1-yl)propanoic acid 3-(5-{5-[3-Ethyl-4-(1-piperidinyl)phenyl]-1,2,4-oxadiazol-3-yl}-1H-indazol-1-yl)propanoic acid 3-{5-[5-(4-Cyclohexyl-3-ethylphenyl)-1,2,4-oxadiazol-3-yl]-1H-indazol-1-yl}propanoic acid 3-(5-{5-[3-Cyano-4-(2-methylpropyl)phenyl]-1,2,4-oxadiazol-3-yl}-1H-indazol-1-yl)propanoic acid 3-[5-(5-{3-Bromo-4-[(1-methylethyl)oxy]phenyl}-1,2,4-oxadiazol-3-yl)-1H-indazol-1-yl]propanoic acid 3-(5-{5-[3-Chloro-4-(2-methylpropyl)phenyl]-1,2,4-oxadiazol-3-yl}-1H-indazol-1-yl)propanoic acid 4-(5-{5-[4-[(1-Methylethyl)oxy]-3-(trifluoromethyl)phenyl]-1,2,4-oxadiazol-3-yl}-1H-indazol-1-yl)butanoic acid 3-{5-[5-(2-Cyano-4-biphenylyl)-1,2,4-oxadiazol-3-yl]-1H-indazol-1-yl}propanoic acid 3-(5-{5-[3-Chloro-4-(1-pyrrolidinyl)phenyl]-1,2,4-oxadiazol-3-yl}-1H-indazol-1-yl)propanoic acid 4-[5-(5-{5-Chloro-6-[(1-methylethyl)oxy]-3-pyridinyl}-1,2,4-oxadiazol-3-yl)-1H-indazol-1-yl]butanoic acid hydrochloride 4-[5-(5-{5-Chloro-6-[(1-methylethyl)oxy]-3-pyridinyl}-1,2,4-oxadiazol-3-yl)-2H-indazol-2-yl]butanoic acid hydrochloride 4-(5-{5-[2-(Trifluoromethyl)-4-biphenylyl]-1,2,4-oxadiazol-3-yl}-1H-indazol-1-yl)butanoic acid 4-(5-{5-[2-(Trifluoromethyl)-4-biphenylyl]-1,2,4-oxadiazol-3-yl}-2H-indazol-2-yl)butanoic acid 3-[4-(5-{3-Cyano-4-[(1-methylethyl)oxy]phenyl}-1,2,4-oxadiazol-3-yl)-1H-indazol-1-yl]propanoic acid 3-[4-(5-{3-Chloro-4-[(1-methylethyl)oxy]phenyl}-1,2,4-oxadiazol-3-yl)-2H-indazol-2-yl]propanoic acid 3-[4-(5-{3-Cyano-4-[(1-methylethyl)oxy]phenyl}-1,2,4-oxadiazol-3-yl)-2H-indazol-2-yl]propanoic acid 4-[4-(5-{3-Cyano-4-[(1-methylethyl)oxy]phenyl}-1,2,4-oxadiazol-3-yl)-1H-indazol-1-yl]butanoic acid 4-(4-{5-[3-Ethyl-4-(1-piperidinyl)phenyl]-1,2,4-oxadiazol-3-yl}-1H-indazol-1-yl)butanoic acid 4-(4-{5-[2-(Trifluoromethyl)-4-biphenylyl]-1,2,4-oxadiazol-3-yl}-1H-indazol-1-yl)butanoic acid 4-[4-(5-{3-Chloro-4-[(trifluoromethyl)oxy]phenyl}-1,2,4-oxadiazol-3-yl)-1H-indazol-1-yl]butanoic acid 3-(4-{5-[4-[(1-Methylethyl)oxy]-3-(trifluoromethyl)phenyl]-1,2,4-oxadiazol-3-yl}-1H-indazol-1-yl)propanoic acid 4-[4-(5-{5-Chloro-6-[(1-methylethyl)oxy]-3-pyridinyl}-1,2,4-oxadiazol-3-yl)-1H-indazol-1-yl]butanoic acid 4-(4-{5-[4-Phenyl-5-(trifluoromethyl)-2-thienyl]-1,2,4-oxadiazol-3-yl}-1H-indazol-1-yl)butanoic acid 4-[4-(5-{3-Chloro-4-[(1-methylethyl)oxy]phenyl}-1,2,4-oxadiazol-3-yl)-2H-indazol-2-yl]butanoic acid 3-{5-[5-(3-Cyano-4-{[(1S)-1-methylpropyl]oxy}phenyl)-1,2,4-oxadiazol-3-yl]-1H-indazol-1-yl}propanoic acid sodium salt 3-{5-[5-(3-Cyano-4-{[(1R)-1-methylpropyl]oxy}phenyl)-1,2,4-oxadiazol-3-yl]-1H-indazol-1-yl}propanoic acid sodium salt 3-(5-{5-[3-Cyano-4-(cyclopentyloxy)phenyl]-1,2,4-oxadiazol-3-yl}-1H-indazol-1-yl)propanoic acid 4-[5-(5-{3-Chloro-4-[(1-methylethyl)oxy]phenyl}-1,2,4-oxadiazol-3-yl)-1H-indazol-1-yl]butanoic acid 4-(5-{5-[4-Phenyl-5-(trifluoromethyl)-2-thienyl]-1,2,4-oxadiazol-3-yl}-1H-indazol-1-yl)butanoic acid 4-[5-(5-{3-Cyano-4-[(1-methylethyl)oxy]phenyl}-1,2,4-oxadiazol-3-yl)-2H-indazol-2-yl]butanoic acid 3-[5-(5-{3-Chloro-4-[(1-methylethyl)oxy]phenyl}-1,2,4-oxadiazol-3-yl)-1H-indazol-1-yl]-2,2-dimethylpropanoic acid 3-[5-(5-{3-Chloro-4-[(1-methylethyl)oxy]phenyl}-1,2,4-oxadiazol-3-yl)-2H-indazol-2-yl]-2,2-dimethylpropanoic acid 3-[4-(5-{3-Chloro-4-[(1-methylethyl)oxy]phenyl}-1,2,4-oxadiazol-3-yl)-1H-indazol-1-yl]-2,2-dimethylpropanoic acid 3-[4-(5-{5-Chloro-6-[(1-methylethyl)oxy]-3-pyridinyl}-1,2,4-oxadiazol-3-yl)-1H-indazol-1-yl]-2,2-dimethylpropanoic acid 3-[5-(5-{3-Cyano-4-[(1-methylethyl)oxy]phenyl}-1,2,4-oxadiazol-3-yl)-1H-indazol-1-yl]-2,2-dimethylpropanoic acid 4-[5-(5-{3-Cyano-4-[(1-methylethyl)oxy]phenyl}-1,2,4-oxadiazol-3-yl)-1H-indazol-1-yl]-2,2-dimethylbutanoic acid 3-[4-(5-{3-Cyano-4-[(1-methylethyl)oxy]phenyl}-1,2,4-oxadiazol-3-yl)-1H-indazol-1-yl]-2,2-dimethylpropanoic acid 3-[5-(5-{5-Chloro-6-[(1-methylethyl)oxy]-3-pyridinyl}-1,2,4-oxadiazol-3-yl)-1H-indazol-1-yl]-2,2-dimethylpropanoic acid 4-[4-(5-{3-Cyano-4-[(1-methylethyl)oxy]phenyl}-1,2,4-oxadiazol-3-yl)-1H-indazol-1-yl]-2,2-dimethylbutanoic acid 4-[4-(5-{5-Chloro-6-[(1-methylethyl)oxy]-3-pyridinyl}-1,2,4-oxadiazol-3-yl)-1H-indazol-1-yl]-2,2-dimethylbutanoic acid or salts thereof.

Pharmaceutically acceptable derivatives of compounds of formula (I) include any pharmaceutically acceptable salt, ester or salt of such ester of a compound of formula (I) which, upon administration to the recipient is capable of providing (directly or indirectly) a compound of formula (I) or an active metabolic or residue thereof.

Certain esters of compounds of formula (I) are described herein as intermediates in the synthesis of some of the described Examples. Such esters may also exhibit activity as S1P1 agonists and as such form part of the invention.

The compounds of formula (I) can form salts. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms. Salts may also be prepared from pharmaceutically acceptable bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic bases include salts of primary, secondary, and tertiary amines; substituted amines including naturally occurring substituted amines; and cyclic amines. Particular pharmaceutically acceptable organic bases include arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, procaine, purines, theobromine, triethylamine, trimethylamine, tripropylamine, tris(hydroxymethyl)aminomethane (TRIS, trometamol) and the like. Salts may also be formed from basic ion exchange resins, for example polyamine resins. When the compound of the present invention is basic, salts may be prepared from pharmaceutically acceptable acids, including inorganic and organic acids. Such acids include acetic, benzenesulfonic, benzoic, camphorsulfonic, citric, ethanesulfonic, ethanedisulfonic, fumaric, gluconic, glutamic, hydrobromic, hydrochloric, isethionic, lactic, maleic, malic, mandelic, methanesulfonic, mucic, pamoic, pantothenic, phosphoric, propionic, succinic, sulfuric, tartaric, p-toluenesulfonic acid, and the like.

The compounds of formula (I) may be prepared in crystalline or non-crystalline form, and, if crystalline, may optionally be hydrated or solvated. This invention includes within its scope stoichiometric hydrates or solvates as well as compounds containing variable amounts of water and/or solvent.

In a further aspect, this invention provides processes for the preparation of a compound of formula (I). It will be appreciated by the person skilled in the art that Schemes 1 to 8 are also applicable to the production of compounds of formula (I) wherein $R_6$ is (a) (rather than $R_5$ is (a) as depicted) by using the appropriate intermediates. Compounds of formula (IV) are known in the literature and are commercially available for isomers where either $R_6$ is (a) or $R_5$ is (a).

One route which may be used to prepare compounds of formula (IA) is illustrated in scheme 1.

Scheme 1

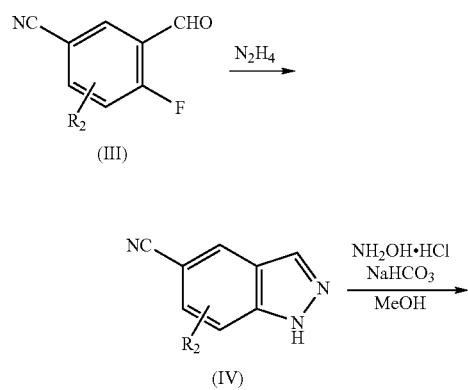

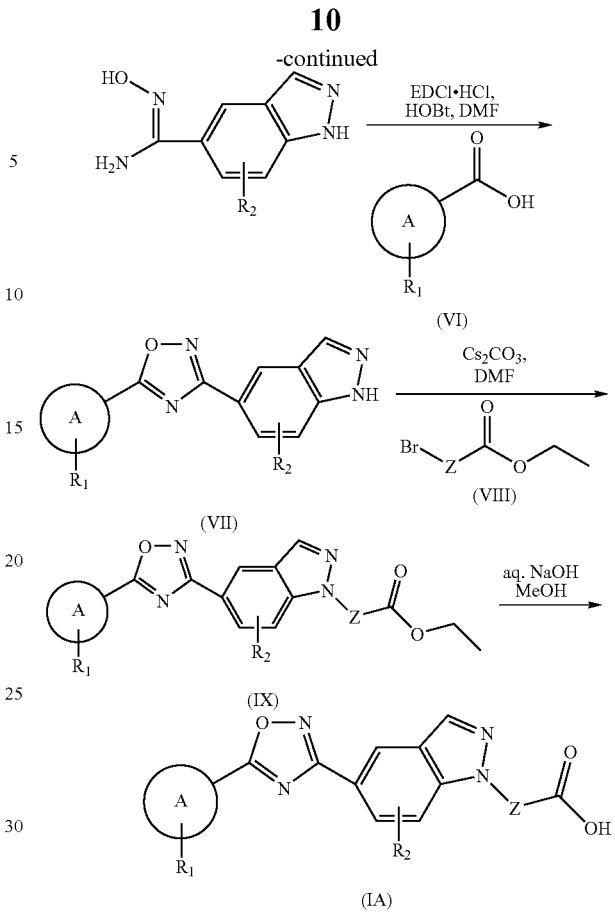

Compounds of formula (III) may be converted into compounds of formula (IV) by treatment with hydrazine hydrate, alternatively compounds of formula (IV) may be commercially available or may be prepared as described in the literature.

Compounds of formula (IV) may be converted into compounds of formula (V) by treatment with hydroxylamine hydrochloride and an appropriate base, such as sodium bicarbonate, in a solvent such as methanol or ethanol at an elevated temperature such as 50° C.

Compounds of formula (V) may be converted into compounds of formula (VII) by treatment with a carboxylic acid of formula (VI) in the presence of EDAC and HOBt in a suitable solvent such as DMF. Such reactions are typically carried out at elevated temperature, such as 50-80° C. Typically, the acid (VI), EDAC and HOBt are stirred for a period of time at room temperature prior to addition of the compound of formula (V). Acids of formula (VI) are either commercially available or may be prepared by a number of routes as in the descriptions which follow.

Compounds of formula (VII) may be converted into compounds of formula (IX) by treatment with an alkylating agent (VIII) in the presence of a base such as cesium carbonate in a solvent such as DMF or DMPU. Such reactions may be carried out at elevated temperature, such as 80° C. or in a microwave reactor at a temperature such as 140° C. The alkylating agents (VIII) are typically commercially available or may be prepared using standard methods.

Compounds of formula (IX) may be converted into compounds of formula (IA) by treatment with a base such as aqueous sodium hydroxide in an alcoholic solvent such as ethanol or methanol. A co-solvent, such as THF, may be added to aid dissolution. The hydrolysis reaction may be carried out at room temperature or at an elevated temperature such as 50-80° C. Alternatively, this transformation may be carried out using solid sodium hydroxide in ethanol in a microwave reactor at a temperature such as 100° C. Alternatively, such reactions may be carried out in a microwave reactor, using dimethylamine in ethanol with added water at a temperature such as 160° C.

The reaction between (VII) and (VIII) to generate (IX) may also generate isomeric compounds of formula (X) (Scheme 2). Treatment of a compound of formula (VII) with an alkylating agent of formula (VIII) with a base such as cesium carbonate in a solvent such as DMF as described previously, generates a mixture of compounds of formula (IX) and (X) which can typically be separated by chromatography.

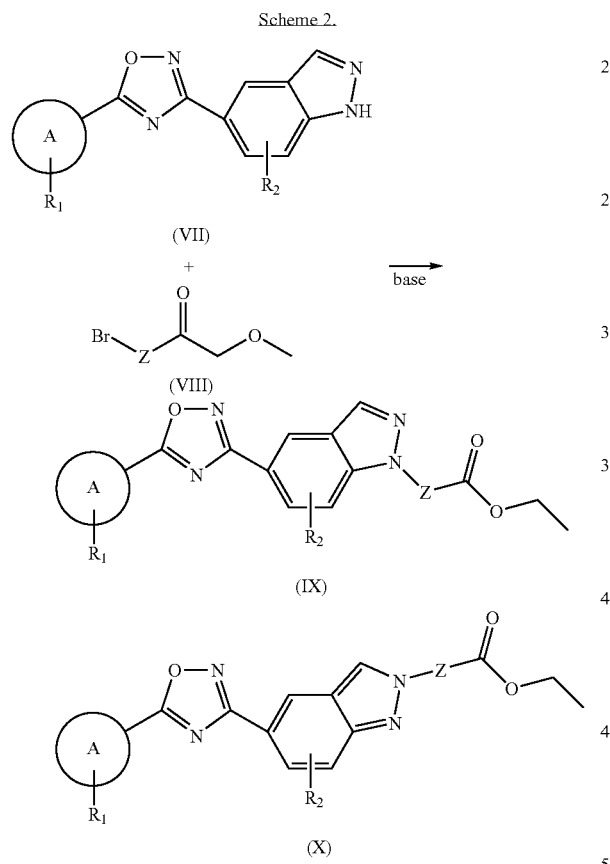

A compound of formula (X) may be converted into a compound of formula (IB) by a hydrolysis step described in Scheme 3.

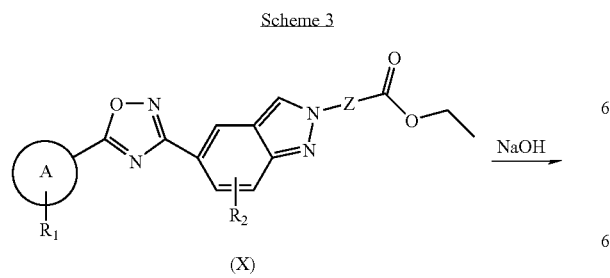

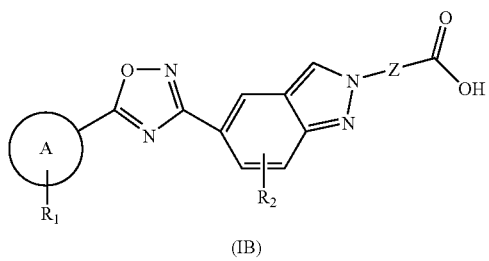

Alternatively, compounds of formula (IA) and (IB) may be prepared by the route outlined in schemes 4, 5 and 6. Compounds of formula (XI) and (XII) can be generated from compounds of formula (IV) by reaction with an alkylating agent of formula (VIII) in the presence of a base such as cesium carbonate in a solvent such as DMF. Typically such reactions are performed at an elevated temperature such as 80° C. On some occasions the compounds (XI) and (XII) are separated by chromatography whilst on other occasions a mixture of the two is used in subsequent reactions generating a mixture of (IX) and (X) which can typically be separated by chromatography.

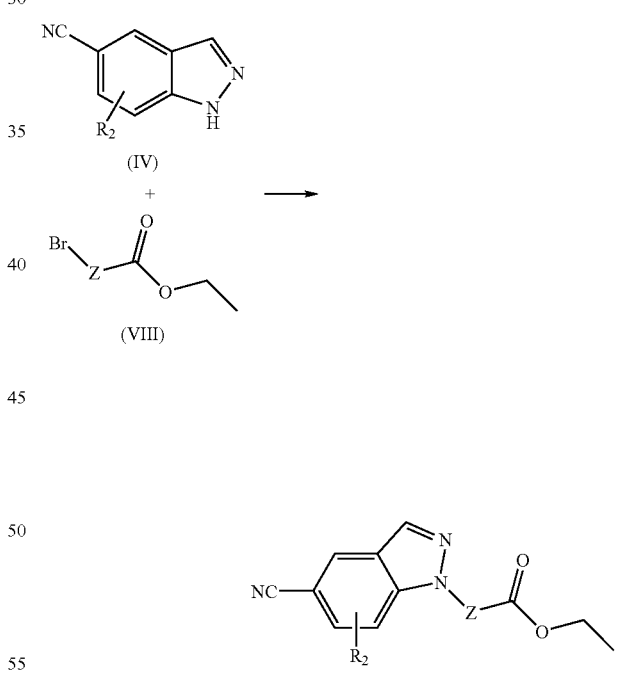

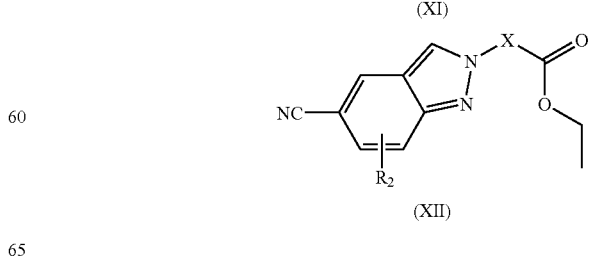

Compounds of formula (XI) can be converted into compounds of formula (IX) as outlined in scheme 5.

bined and heated together. Compounds of formula (IX) can be converted to compounds of formula (IA) as previously described.

Compounds of formula (XII) can be converted into compounds of formula (X) as outlined in Scheme 6

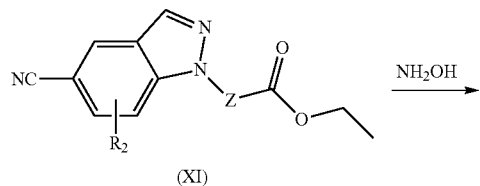

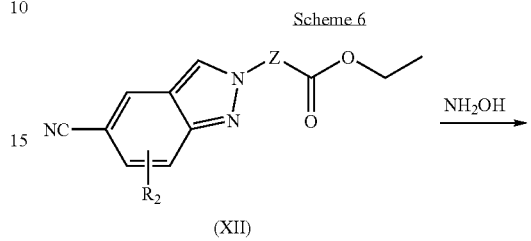

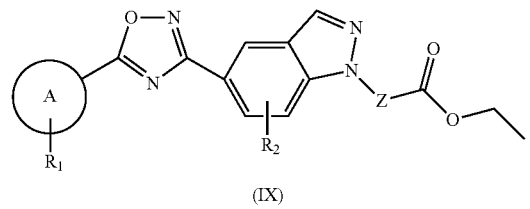

Compounds of formula (XI) can be converted into compounds of formula (XIII) by treatment with hydroxylamine hydrochloride and a base such as sodium bicarbonate in a solvent such as ethanol at elevated temperature, for example 50° C. Compounds of formula (XIII) can be converted into compounds of formula (IX) by treatment with a carboxylic acid of formula (VI) in the presence of EDAC and HOBt in a suitable solvent such as DMF. Such reactions are typically carried out at elevated temperature, such as 50-120° C. Sometimes the acid (VI), EDAC and HOBt are stirred for a period of time at room temperature prior to addition of the compound of formula (XII) alternatively all the reagents can be combined and heated together. Compounds of formula (IX) can be converted to compounds of formula (IA) as previously described.

Compounds of formula (XII) can be converted into compounds of formula (XIV) by treatment with hydroxylamine hydrochloride and a base such as sodium bicarbonate in a solvent such as ethanol at elevated temperature, for example 50° C.

Compounds of formula (XIV) can be converted into compounds of formula (X) by treatment with a carboxylic acid of formula (VI) in the presence of EDAC and HOBt in a suitable solvent such as DMF. Such reactions are typically carried out at elevated temperature, such as 80-120° C. The acid (VI), EDAC and HOBt may be stirred for a period of time at room temperature prior to addition of the compound of formula (IX) alternatively all the reagents may be combined and heated together. Compounds of formula (X) can be converted to compounds of formula (IB) as previously described.

Compounds of formula (XI) wherein Z is —CH$_2$—CH$_2$— (shown as compounds of formula (XVIII)) may also be prepared by the routes outlined in Scheme 7.

Scheme 7

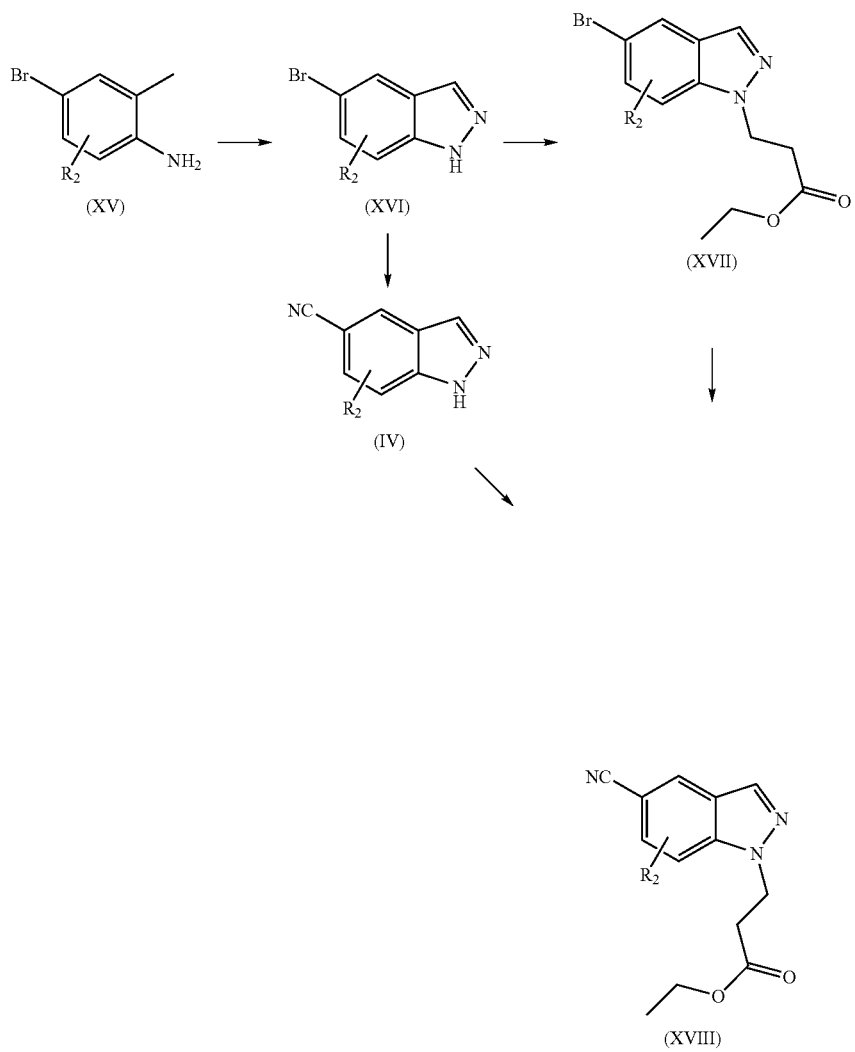

Compounds of formula (XV) can be converted into compounds of formula (XVI) by treatment with acetic anhydride in a solvent, such as chloroform at a temperature between 5° C. and 15° C., followed by treatment with a base such as potassium acetate and isoamyl nitrite at a temperature between room temperature and 80° C.

Compounds of formula (XVI) can be converted into compounds of formula (XVI) avoiding the formation of isomer (XIX):

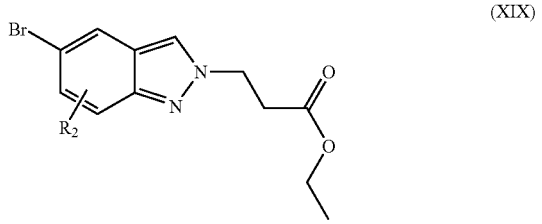

by treatment with ethyl 2-propenoate in the presence of a base such as DBU and in a solvent such as acetonitrile at a reflux temperature.

Compounds of formula (XVII) can be converted into compounds of formula (XVIII) by treatment with dicyanozinc in the presence of a catalyst such as $Pd_2(dba)_3$ and of a ligand such as DPPF in a solvent such as 1,4-dioxan at a reflux temperature.

Alternatively, compounds of formula (XVI) can be converted into compounds of formula (IV) by treatment with dicyanozinc [$Zn(CN)_2$] in the presence of a catalyst such as $Pd(PPh_3)_4$ in a solvent such as NMP at a temperature such as 80° C. Compounds of formula (IV) can then be converted into compounds of formula (XVIII) in a similar manner to those used to convert compounds of formula (XV) into compounds of formula (XVII).

Compounds of formula (XIII) can be converted into compounds of formula (IX) according to the route outlined in Scheme 8:

Scheme 8

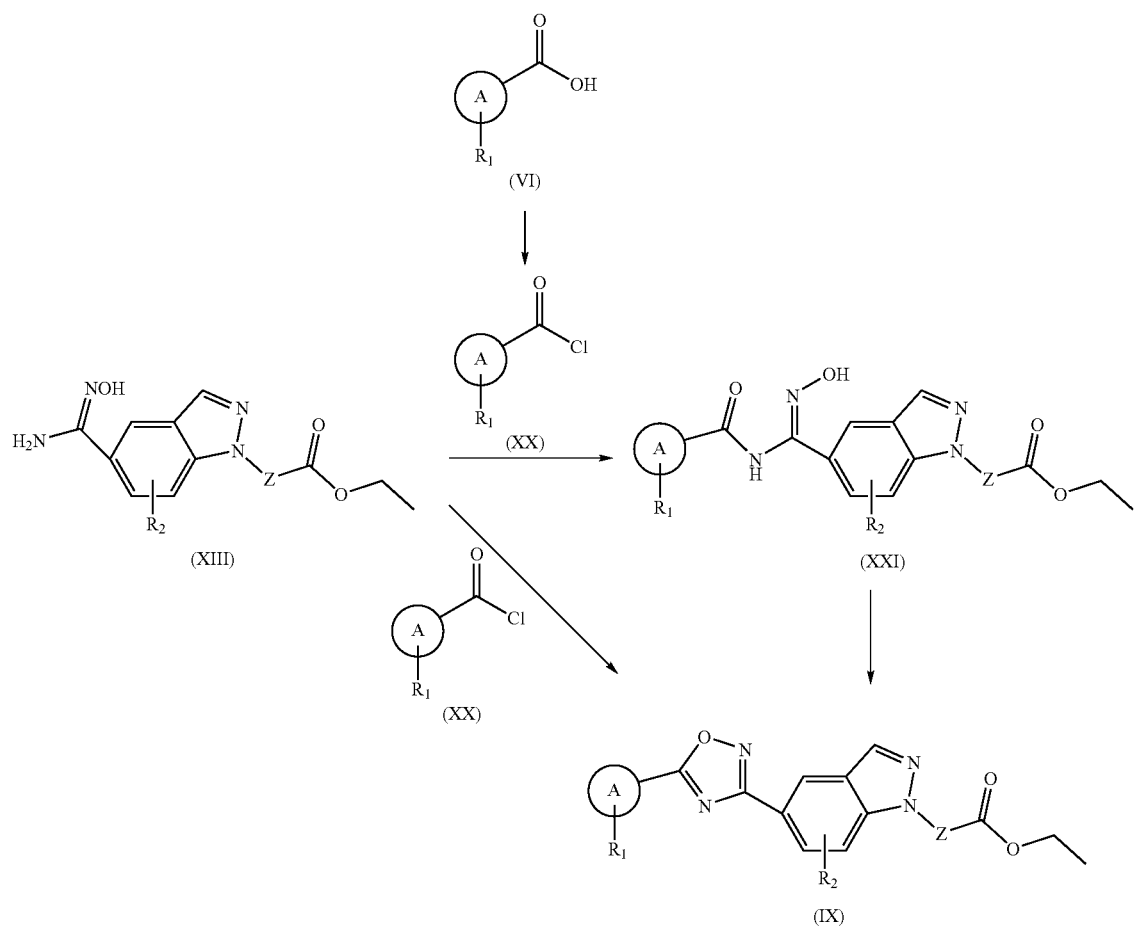

Compounds of formula (VI) can be converted into compounds of formula (XIX) by treatment with oxalyl chloride in the presence of DMF in a solvent such as dichloromethane at room temperature.

Compounds of formula (XIII) can be converted into compounds of formula (XXI) by treatment with compounds of formula (XX) in the presence of a base such as triethylamine in a solvent such as dichloromethane at 0° C.

Compounds of formula (XXI) can be converted into compounds of formula (IX) following heating at 100° C. in the presence of a solvent such as actonitrile.

"Alternatively, compounds of formula (XIII) can be converted into compounds of formula (IX) by treatment with compounds of formula (XX) and triethylamine in a solvent such as acetonitrile at a temperature between room temperature and 110° C.":

Compounds of formula (I) and their pharmaceutically acceptable salts are therefore of use in the treatment of conditions or disorders which are mediated via the S1P1 receptor. In particular the compounds of formula (I) and their pharmaceutically acceptable salts are of use in the treatment of multiple sclerosis, autoimmune diseases, chronic inflammatory disorders, asthma, inflammatory neuropathies, arthritis, transplantation, Crohn's disease, ulcerative colitis, lupus erythematosis, psoriasis, ischemia-reperfusion injury, solid tumours, and tumour metastasis, diseases associated with angiogenesis, vascular diseases, pain conditions, acute viral diseases, inflammatory bowel conditions, insulin and non-insulin dependant diabetes (herein after referred to as the "Disorders of the Invention").

It is to be understood that "treatment" as used herein includes prophylaxis as well as alleviation of established symptoms.

Thus the invention also provides a compound of formula (I) or a pharmaceutically acceptable salt thereof, for use as a therapeutic substance, in particular in the treatment of the conditions or disorders mediated via the S1P1 receptor. In particular the invention provides a compound of formula (I) or a pharmaceutically acceptable salt thereof for use as a therapeutic substance in the treatment of multiple sclerosis, autoimmune diseases, chronic inflammatory disorders, asthma, inflammatory neuropathies, arthritis, transplantation, Crohn's disease, ulcerative colitis, lupus erythematosis, psoriasis, ischemia-reperfusion injury, solid tumours, and tumour metastasis, diseases associated with angiogenesis, vascular diseases, pain conditions, acute viral diseases, inflammatory bowel conditions, insulin and non-insulin dependant diabetes. The invention further provides a method of treatment of conditions or disorders in mammals including humans which can be mediated via the S1P1 receptor, which comprises administering to the sufferer a therapeutically safe and effective amount of a compound of formula (I) or a pharmaceutically acceptable salt thereof.

In another aspect, the invention provides for the use of a compound of formula (I) or a pharmaceutically acceptable salt thereof in the manufacture of a medicament for use in the treatment of the conditions or disorders mediated via the S1P1 receptor In order to use the compounds of formula (I) in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier or excipient.

In a further aspect, the present invention provides a process for preparing a pharmaceutical composition, the process comprising mixing a compound of formula (I) or a pharmaceutically acceptable salt thereof and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

The potencies and efficacies of the compounds of this invention for the S1P1 receptor can be determined by GTPγS assay performed on the human cloned receptor as described herein or by the yeast binding assay, also described herein Compounds of formula (I) have demonstrated agonist activity at the S1P1 receptor, using the functional assays described herein.

Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound.

For parenteral administration, fluid unit dosage forms are prepared utilising a compound of the invention or pharmaceutically acceptable salt thereof and a sterile vehicle. Formulations for injection may be presented in unit dosage form e.g. in ampoules or in multi-dose, utilising a compound of the invention or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device. Thus compounds of formula (I) may be formulated for oral, buccal, parenteral, topical (including ophthalmic and nasal), depot or rectal administration or in a form suitable for administration by inhalation or insufflation (either through the mouth or nose).

The compounds of formula (I) or pharmaceutically acceptable salts thereof may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, 1.0 to 500 mg or 1.0 to 200 mg and such unit doses may be administered more than once a day, for example two or three times a day.

The compounds of formula (I) or pharmaceutically acceptable salts thereof may be used in combination preparations. For example, the compounds of the invention may be used in combination with cyclosporin A or other therapeutically active compounds.

The subject invention also includes isotopically-labeled compounds, which are identical to those recited in formulas I and following, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3$H, $^{11}$C, $^{14}$C, $^{18}$F, $^{123}$I and $^{125}$I.

Compounds of formula (I) and pharmaceutically acceptable salts of said compounds that contain the aforementioned isotopes and/or other isotopes of other atoms are within the scope of the present invention. Isotopically-labeled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^8$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of formula I and following of this invention can generally be prepared by carrying out the procedures disclosed in the Schemes and/or in the Examples below, by substituting a readily available isotopically labeled reagent for a non-isotopically labeled reagent.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of compounds of the invention.

The following information on hardware and software for analytical methods is given for purposes of illustration only.
Conditions, Hardware and Software for Analytical LCMS Systems
Hardware
Agilent 1100 Gradient Pump
Agilent 1100 Autosampler
Agilent 1100 DAD Dectector
Agilent 1100 Degasser
Agilent 1100 Oven
Agilent 1100 Controller
Waters Acquity Binary Solvent Manager
Waters Acquity Sample Manager
Waters Acquity PDA
Waters ZQ Mass Spectrometer
Sedere Sedex 55, Sedere Sedex 85, Sedere Sedex 75 or Polymer Labs PL-ELS-2100
Software
    Waters MassLynx version 4.0 SP2 or version 4.1
For 5 Minute Method
Column
    The column used is a Waters Atlantis, the dimensions of which are 4.6 mm×50 mm.
The stationary phase particle size is 3 μm.
Solvents
A: Aqueous solvent=Water+0.05% Formic Acid
B: Organic solvent=Acetonitrile+0.05% Formic Acid
Method
    The generic method used has a 5 minute runtime.

| Time/min | % B |
|---|---|
| 0 | 3 |
| 0.1 | 3 |
| 4 | 97 |
| 4.8 | 97 |
| 4.9 | 3 |
| 5.0 | 3 |

Flow Rate
    The above method has a flow rate of 3 ml/mins
For 2 Minute Method
Software
    Waters MassLynx version 4.1
Column
    The column used is a Waters Acquity BEH UPLC C18, the dimensions of which are 2.1 mm×50 mm. The stationary phase particle size is 1.7 μm.
Solvents
A: Aqueous solvent=Water+0.05% Formic Acid
B: Organic solvent=Acetonitrile+0.05% Formic Acid
Weak Wash=1:1 Methanol:Water
Strong Wash=Water
Method
    The generic method used has a 2 minute runtime.

| Time/min | % B |
|---|---|
| 0 | 3 |
| 0.1 | 3 |
| 1.5 | 97 |
| 1.9 | 97 |
| 2.0 | 3 |

The above method has a flow rate of 1 ml/min.
The injection volume for the generic method is 0.5 ul
The column temperature is 40 deg
The UV detection range is from 220 to 330 nm
Open Access Mass Directed Auto Prep System (MDAP)
Hardware
    Open Access Mass Directed Prep instruments consist of the following:
1 Waters 600 Gradient pump
1 Waters 2767 inject/collector
1 Waters Reagent manager
1 MicroMass ZQ Mass Spectrometer
1 Gilson Aspec—waste collector
1 Gilson 115 post-fraction UV detector
1 Computer System.
Software
    MicroMass MassLynx v4.0
Column
    The column used is typically a Supelco LCABZ++ column whose dimensions are 20 mm internal diameter by 100 mm in length. The stationary phase particle size is 5 μm.
Solvents
A: Aqueous solvent=Water+0.1% Formic Acid
B: Organic solvent=MeCN:Water 95:5+0.05% Formic Acid Make up solvent=MeOH:Water 80:20+50 mMol Ammonium Acetate
Needle rinse solvent=MeOH:Water:DMSO 80:10:10
Methods
One of five methods may be used depending on the analytical retention time of the compound of interest.
All have a 15-minute runtime, which comprises of a 10-minute gradient followed by a 5-minute column flush and re-equilibration step.
MDP 1.5-2.2=0-30% B
MDP 2.0-2.8=5-30% B
MDP 2.5-3.0=15-55% B
MDP 2.8-4.0=30-80% B
MDP 3.8-5.5=50-90% B
Flow Rate
All of the above methods have a flow rate of 20 ml/min.
Alternative System:
Hardware
  Waters 2525 Binary Gradient Module
  Waters 515 Makeup Pump
  Waters Pump Control Module
  Waters 2767 Inject Collect
  Waters Column Fluidics Manager
  Waters 2996 Photodiode Array Detector
  Waters ZQ Mass Spectrometer
  Gilson 202 fraction collector
  Gilson Aspec waste collector
Software
  Waters MassLynx version 4 SP2
Column
The columns used are Waters Atlantis, the dimensions of which are 19 mm×100 mm (small scale) and 30 mm×100 mm (large scale). The stationary phase particle size is 5 mm.
Solvents
A: Aqueous solvent=Water+0.1% Formic Acid
B: Organic solvent=Acetonitrile+0.1% Formic Acid
Make up solvent=Methanol:Water 80:20
Needle rinse solvent=Methanol
Methods
There are five methods used depending on the analytical retention time of the compound of interest. They have a 13.5-minute runtime, which comprises of a 10-minute gradient followed by a 3.5 minute column flush and re-equilibration step.
Large/Small Scale 1.0-1.5=5-30% B
Large/Small Scale 1.5-2.2=15-55% B
Large/Small Scale 2.2-2.9=30-85% B
Large/Small Scale 2.9-3.6=50-99% B
Large/Small Scale 3.6-5.0=80-99% B (in 6 minutes followed by 7.5 minutes flush and re-equilibration)
Flow Rate
All of the above methods have a flow rate of either 20 mls/min (Small Scale) or 40 mls/min (Large Scale).
Shallow Gradients
Large 1.5 to 2.3 min=13-29% B
Large 1.9 to 2.3 min=25-41% B
Large 2.3 to 2.6 min=37-53% B
Large 2.6 to 3.1 min=49-65% B
Large 3.1 to 3.6 min=61-77% B
Conditions Used for NMR
Hardware
Bruker 400 MHz Ultrashield
Bruker B-ACS60 Autosampler
Bruker Advance 400 Console
Bruker DPX250
Bruker AVANCE 500
Bruker DRX600
Software
  User interface—NMR Kiosk
  Controlling software—XWin NMR version 3.0
Chromatography
Unless stated otherwise, all chromatography was carried out using silica columns
Abbreviations:
g—grams
mg—milligrams
ml—millilitres
ul—microlitres
$CHCl_3$—chloroform
MeCN—acetonitrile
MeOH—methanol
EtOH—ethanol
EtOAc—ethyl acetate
DBA—dibenzylidenacetone
DCM—dichloromethane
DMF—N,N-dimethylformamide
DMPU—1,3-dimethyl-3,4,5,6-tetrahydro-2(1H)-pyrimidinone
DMSO—dimethylsulphoxide
DPPF—1,1'-bis(diphenylphosphino)ferrocene
EDC—N-(3-Dimethylaminopropyl)-N'-ethylcarbodiimide hydrochloride
EDAC—N-(3-Dimethylaminopropyl)-N'-ethylcarbodiimide hydrochloride
EDCl.HCl—N-(3-Dimethylaminopropyl)-N'-ethylcarbodiimide hydrochloride
HATU—2-(1H-7-Azabenzotriazol-1-yl)-1,1,3,3-tetramethyl uronium hexafluorophosphate Methanaminium
IPA—Isopropanol
NMP—N-Methyl-2-pyrrolidinone
PyBOP—Benzotriazol-1-yl-oxytripyrrolidinophosphonium hexafluorophosphate
THF—Tetrahydrofuran
dba—dibenzylidene acetone
RT—room temperature
° C.—degrees Celsius
M—Molar
H—proton
s—singlet
d—doublet
t—triplet
q—quartet
LCMS—Liquid Chromatography Mass Spectrometry
LC/MS—Liquid Chromatography Mass Spectrometry
NMR—Nuclear magnetic resonance
MS—mass spectrometry
ES—Electrospray
$MH^+$—mass ion+$H^+$
MDAP—mass directed automated preparative liquid chromatography
SCX—Strong cation exchange General Chemistry The intermediates for the preparation of the examples may not necessarily have been prepared from the specific batch described.

Description of D1

1H-indazole-5-carbonitrile (D1)

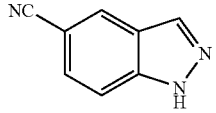

2-fluoro-5-cyanobenzaldehyde (1.1 g) is dissolved in hydrazine hydrate (19 ml) and stirred at room temperature for 18 hours. The solution is then distilled and the residue purified by flash column chromatography on silica, eluting with DCM. This gives the title compound (300 mg).

Description of D1 (Alternative Procedure)

1H-indazole-5-carbonitrile (D1)

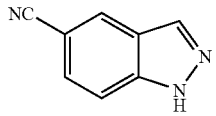

5-Cyano-3-fluorobenzaldehyde (4 g, 26.8 mmol) was dissolved in hydrazine hydrate and stirred at room temperature for 18 hours. The solution was poured onto ice and the resultant solid was separated by filtration and then dried under vacuum at 60° C. to afford the title compound (1.27 g) as a pink solid. Further material was isolated from the aqueous layer. MS (ES): $C_8H_5N_3$ requires 143; found 144 (MH$^+$).

1H-indazole-5-carbonitrile can also be prepared as described previously (Halley and Sava 1997, Synth. Commun. 27(7):1199-1207).

Description of D2

N-hydroxy-1H-indazole-5-carboximidamide (D2)

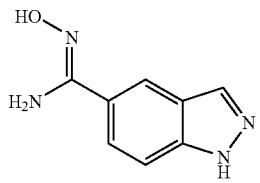

5-cyano indazole (D1) (500 mg), hydroxylamine.HCl (485 mg) and NaHCO$_3$ (1.47 g) were dissolved/suspended in MeOH (18 ml), heated to 50° C. and stirred for 19 hours and overnight. The reaction mixture was then filtered, washed with MeOH and evaporated to give the title compound (584 mg) as a white solid. MS (ES): $C_8H_8N_4O$ requires 176; found 177 (MH$^+$).

Description of D3

3-chloro-4-[(1-methylethyl)oxy]benzoic acid (D3)

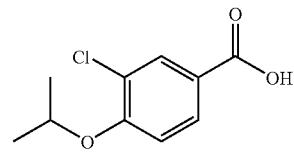

Methyl-4-hydroxy-3-chloro benzoate (13.4 g) was dissolved in DMF (150 ml), treated with K$_2$CO$_3$ (19.9 g) followed by isopropyl bromide (13.5 ml) and the resultant mixture heated to 70° C. and stirred overnight. The reaction mixture was then cooled to RT, evaporated to dryness, redissolved in EtOH, filtered and evaporated once more to give the intermediate ester (22.24 g) as a white solid. This compound was a 3:1 mixture of ethyl and methyl esters and used crude in the next reaction.

The crude intermediate (22.24 g) was dissolved in MeOH (75 ml), treated with 2M aqueous NaOH (75 ml), heated to 60° C. and stirred for 2 hours. The reaction mixture was then cooled to RT, the MeOH evaporated and the remaining aqueous solution acidified with 5M aqueous HCl (30 ml). The precipitate was filtered off and dried to give the title compound (15.1 g) as a white solid. δH (CDCl$_3$, 400 MHz): 1.42 (6H, d), 4.70 (1H, septet), 6.97 (1H, d), 7.97 (1H, d), 8.12 (1H, s). MS (ES): $C_{10}H_{11}ClO_3$ requires 214; found 213 (M−H$^+$).

3-Chloro-4-[(1-methylethyl)oxy]benzoic acid may be prepared as described in WO2006047195.

Description of D4

5-(5-{3-Chloro-4-[(1-methylethyl)oxy]phenyl}-1,2,4-oxadiazol-3-yl)-1H-indazole (D4)

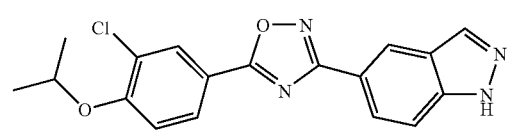

3-chloro-4-[(1-methylethyl)oxy]benzoic acid (D3) (712 mg), EDCl.HCl (699 mg) and HOBT (493 mg) were dissolved in DMF (16.5 ml) and stirred at RT for 10 minutes. N-hydroxy-1H-indazole-5-carboximidamide (D2) (584 mg) was added and the mixture heated to 80° C. for 12 hours. The reaction mixture was then cooled to RT and left to stand for the weekend, evaporated to dryness and re-dissolved in H$_2$O. This solution was extracted with EtOAc (×3) and the combined extracts washed with brine, evaporated and triturated with DCM twice, sonicated for 4 mins before filtering, drying and repeating once to give the title compound (407 mg) as a pink solid. δH (d$_6$-DMSO, 400 MHz): 1.37 (6H, d), 4.89 (1H, septet), 7.46 (1H, d), 7.73 (1H, d), 8.04 (1H, d), 8.13 (1H, d), 8.20 (1H, s), 8.28 (1H, s), 8.58 (1H, s). MS (ES): $C_{18}H_{15}ClN_4O_2$ requires 354; found 355 (M+H).

Description of D5

Ethyl 3-[5-(5-{3-chloro-4-[(1-methylethyl)oxy]phenyl}-1,2,4-oxadiazol-3-yl)-1H-indazol-1-yl]propanoate (D5)

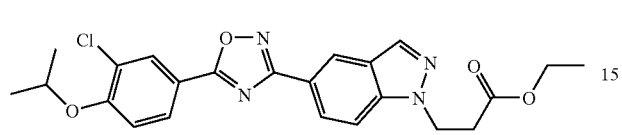

5-(5-{3-Chloro-4-[(1-methylethyl)oxy]phenyl}-1,2,4-oxadiazol-3-yl)-1H-indazole (D4) (200 mg) was dissolved in DMPU (2.8 ml) and treated with $Cs_2CO_3$ (367 mg) followed by ethyl 3-bromopropionate (145 ul). The resultant mixture was heated to 140° C. in a microwave reactor for 1.5 hours. The reaction mixture was then cooled to RT, evaporated to dryness and dissolved in $H_2O$. This solution was extracted with EtOAc (×3) and the combined extracts washed with brine and evaporated to give the title compound (240 mg) as a brown oil. MS (ES): $C_{23}H_{23}{}^{35}ClN_4O_4$ requires 454; found 455 (MH+).

Description of D5 (Alternative Procedure)

Ethyl 3-[5-(5-{3-chloro-4-[(1-methylethyl)oxy]phenyl}-1,2,4-oxadiazol-3-yl)-1H-indazol-1-yl]propanoate (D5)

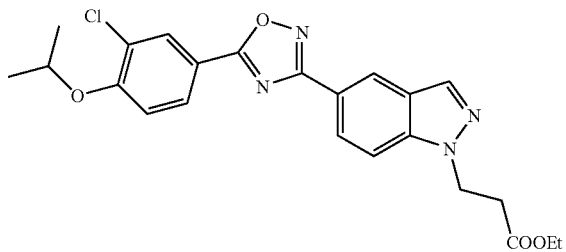

A solution of Ethyl 3-{5-[(hydroxyamino)(imino)methyl]-1H-indazol-1-yl}propanoate (D52) (2.04 g, 7.38 mmol), 3-chloro-4-[(1-methylethyl)oxy]benzoic acid (D3) (1.743 g, 8.12 mmol), EDC (2.123 g, 11.08 mmol) and HOBT (1.357 g, 8.86 mmol) in N,N-Dimethylformamide (DMF) (25 ml) was stirred overnight then heated at 120° C. during 4 hours. The mixture was dissolved in EtOAc then washed with water and $NaHCO_3$ and purified by flash chromatography, eluting with EtOAc/iso-Hexane 10-90% then 10-30%. The solvent was evaporated to give (1.95 g) of white solid. MS (ES): $C_{23}H_{23}{}^{35}ClN_4O_4$ requires 454; found (MH+) 455.

Description of D6

Methyl 3-chloro-4-(ethyloxy)benzoate (D6)

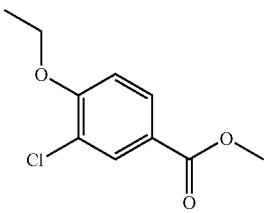

Methyl-4-hydroxy-3-chlorobenzoate (10 g, 53.6 mmol) and potassium carbonate (14.8 g, 107.2 mmol) were suspended in DMF (110 ml) and then ethyl iodide (8.56 ml, 107.2 mmol) was added. The reaction mixture was heated to 70° C. overnight. The reaction mixture was filtered and the residue washed with ether. The organic solutions were evaporated in vacuo and then dissolved in EtOAc and washed with aq. NaOH and water, dried and evaporated to dryness in vacuo to afford the title compound (11.24 g) as a yellow oil. MS (ES): $C_{10}H_{11}{}^{35}ClO_3$ requires 214; found (MH+) 215.

Description of D7

3-Chloro-4-(ethyloxy)benzoic acid (D7)

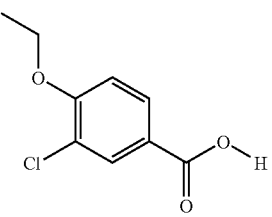

To a stirred suspension of Methyl 3-chloro-4-(ethyloxy) benzoate (D6) (11.24 g, 52.4 mmol) in methanol (40 ml) was added 2M aq. NaOH (40 ml) and the resultant mixture was heated at 60° C. for 2 hours. The reaction mixture was partitioned between EtOAc and dilute hydrochloric acid. The organics were separated, dried and evaporated in vacuo to give the crude product. This material was triturated with ether to give the title compound as a white solid (8.21 g). MS (ES): $C_9H_9{}^{35}ClO_3$ requires 200; found (MH+) 201.

Description of D8

3-Ethyl-4-(1-piperidinyl)benzonitrile (D8)

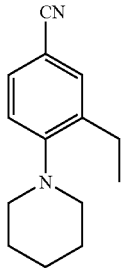

4-Amino-3-ethylbenzonitrile (3.0 g, 20.5 mmol), 1,5-dibromopentane (11.1 mL, 82.1 mmol), potassium carbonate (5.67 g, 41.0 mmol) and water (39.6 mL) were all split equally between ten microwave vials and each heated at 160° C. for 1 h. All the reaction mixtures were combined and extracted twice with ethyl acetate (40 mL) and the combined organic fractions dried (phase separator) and concentrated in vacuo. Dichloromethane was added, the mixture filtered and then the filtrate was purified by silica chromatography, eluting with 2-5% ethyl acetate in hexane to give the title compound as a colourless oil (823 mg, 3.85 mmol). Analysis indicated that the compound contained small amounts of a dibromopentane impurity. MS (ES): $C_{14}H_{18}N_2$ requires 214; found 215 (MH$^+$).

Description of D9

3-Ethyl-4-(1-piperidinyl)benzoic acid (D9)

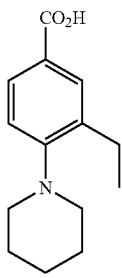

3-Ethyl-4-(1-piperidinyl)benzonitrile (D8) (817 mg, 3.82 mmol) and potassium hydroxide (2.14 g, 38.2 mmol) in ethanol (35 mL) and water (8 mL) were heated to 90° C. (block temperature) for 9 h. Further potassium hydroxide (2.14 g, 38.2 mmol) and water (8 mL) were added and the reaction heated for a further 18 h. The reaction was allowed to cool and was neutralised with aqueous HCl. A white solid was separated by filtration and an attempt was made to purify the filtrate by SCX cartridge, but this failed. Both the solid and product of SCX were combined, methanol added and then the mixture acidified with acetic acid. The mixture was filtered to obtain the filtrate, which was then trapped on SCX cartridge, washed with methanol and eluted with 2M ammonia in methanol. On test scale this gave the title compound as a white solid (96 mg, 0.41 mmol) and on the remaining material gave a colourless oil (563 mg, 2.41 mmol). MS (ES): $C_{14}H_{19}NO_2$ requires 233; found 234 (MH$^+$).

Description of D10

3-Ethyl-4-iodobenzonitrile (D10)

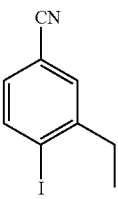

To 4-amino-3-ethylbenzonitrile (2.50 g, 17.1 mmol) stirred in water (14 mL) at 0° C. was added concentrated hydrochloric acid (7.80 mL, 257 mmol) dropwise followed by a solution of sodium nitrite (1.24 g, 18.0 mmol) in water (3.43 mL) dropwise. The resultant mixture was stirred for 15 minutes and then added over 15 minutes to a solution of potassium iodide (2.98 g, 18.0 mmol) in water (6.0 mL) at 0° C. The mixture was stirred at room temperature for 2 h. The mixture was extracted with ethyl acetate (3×100 mL) and the combined organic fractions washed with brine (100 mL), dried (phase separator) and concentrated in vacuo to give the title compound as a brown solid (4.21 g, 16.4 mmol). δH (methanol-d$_4$, 400 MHz): 8.02 (1H, d), 7.61 (1H, d), 7.24 (1H, dd), 2.80 (2H, q), 1.21 (3H, t).

Description of D11

4-(1-Cyclohexen-1-yl)-3-ethylbenzonitrile (D11)

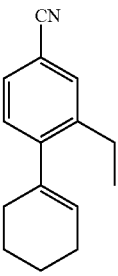

A mixture of 3-ethyl-4-iodobenzonitrile (D10) (1.23 g, 4.80 mmol), 1-cyclohexen-1-ylboronic acid (907 mg, 7.20 mmol), sodium methoxide (778 mg, 14.4 mmol) and bis(triphenylphosphine)palladium (II) chloride (337 mg, 0.48 mmol) in anhydrous methanol (12 mL) was heated at 80° C. for 10 minutes in the microwave. The reaction mixture was partitioned between ethyl acetate (40 mL) and water (40 mL) before the organic layer was further washed with water (40 mL), dried (phase separator) and concentrated in vacuo. The crude material was purified by silica chromatography, eluting 0-5% EtOAc in hexane over 30 minutes to give the title compound as a yellow oil (824 mg, 3.91 mmol). δH (methanol-d$_4$, 400 MHz) 7.56 (1H, d), 7.46 (1H, dd), 7.19 (1H, d), 5.61-5.56 (1H, m), 2.68 (2H, quart), 2.23-2.16 (4H, m), 1.85-1.68 (4H, m), 1.20 (3H, t).

Description of D12

4-(1-Cyclohexen-1-yl)-3-ethylbenzoic acid (D12)

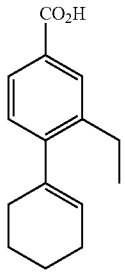

4-(1-Cyclohexen-1-yl)-3-ethylbenzonitrile (D11) (824 mg, 3.91 mmol) and potassium hydroxide (2.19 g, 39.1 mmol) in ethanol (36 mL) and water (8 mL) were heated at 90° C. (block temperature) for 20 h. The reaction mixture was concentrated in vacuo and the residue partitioned between ethyl acetate (120 mL) and aqueous hydrochloric acid (2M, 50 mL) before the organic phase was washed with further hydrochloric acid (2M, 50 mL), dried (phase separator) and concentrated in vacuo to give the title compound as a yellow oil (808 mg, 3.51 mmol). LCMS (ES): $C_{15}H_{18}O_2$ requires 230; found 229 (M–H$^+$).

Description of D13

4-Cyclohexyl-3-ethylbenzoic acid (D13)

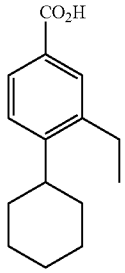

4-(1-Cyclohexen-1-yl)-3-ethylbenzoic acid (D12) (803 mg, 3.49 mmol) was dissolved in methanol (70 mL) and hydrogenated on an H-Cube using a palladium on carbon cartridge. The product solution was concentrated in vacuo to give the title compound as a white solid (792 mg, 3.41 mmol). δH (methanol-d$_4$, 400 MHz): 7.82-7.68 (2H, m), 7.33 (1H, d), 2.83 (1H, m), 2.73 (2H, q), 1.87 (2H, m), 1.85-1.70 (3H, m), 1.58-1.30 (5H, m), 1.22 (3H, t).

Description of D14

1-Methylethyl 3-bromo-4-[(1-methylethyl)oxy]benzoate (D14)

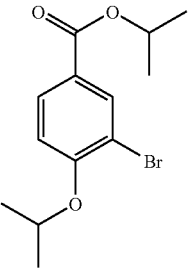

A mixture of 3-bromo-4-hydroxybenzoic acid (2.00 g, 9.22 mmol), 2-iodopropane (1.85 mL, 18.4 mmol) and potassium carbonate (2.55 g, 18.4 mmol) in DMF (175 mL) was heated to reflux for 5 h. The reaction was allowed to cool and was filtered. The filtrate was concentrated in vacuo and the residue partitioned between ethyl acetate (150 mL) and water (150 mL), which was basified with 2M NaOH. The organic phase was dried (phase separator) and concentrated in vacuo to give the title compound as a yellow oil (2.36 g, 7.84 mmol). δH (methanol-d$_4$, 400 MHz): 8.05 (1H, d), 7.90 (1H, dd), 7.25 (1H, d), 5.10 (1H, septet), 4.81 (1H, septet), 1.32 (6H, d), 1.31 (6H, d).

Description of D15

3-Bromo-4-[(1-methylethyl)oxy]benzoic acid (D15)

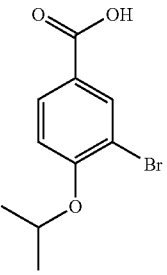

A solution of 1-methylethyl 3-bromo-4-[(1-methylethyl)oxy]benzoate (D14) (2.36 g, 7.84 mmol) in ethanol (100 mL) and aqueous sodium hydroxide (2M, 39 mL) was heated to reflux for 5 h. The reaction mixture was concentrated in vacuo and partitioned between ethyl acetate (125 mL) and water (125 mL), the latter acidified with 2M HCl (40 mL). The aqueous layer was extracted with further ethyl acetate (70 mL) and the combined organic extracts dried (phase separator) and concentrated in vacuo to give the title compound as an off-white solid (1.83 g, 7.06 mmol). MS (ES): $C_{10}H_{11}BrO_3$ requires 258, 260; found 257, 259 (M–H$^+$).

Description of D16

Ethyl 4-bromo-3-chlorobenzoate (D16)

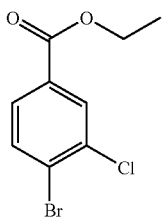

To a suspension of 4-bromo-3-chlorobenzoic acid (5.00 g, 21.2 mmol) in ethanol (50 mL) was added sulphuric acid (5 mL) and the resultant mixture heated to reflux for 60 h. The reaction was partitioned between ethyl acetate (50 mL) and water (50 mL). The aqueous layer was extracted with further ethyl acetate and the combined organic fractions dried (phase separator) and concentrated in vacuo to give the title compound as a brown oil/solid (5.09 g, 19.3 mmol). δH (d$_6$-DMSO, 400 MHz): 8.06 (1H, d), 7.96 (1H, d), 7.80 (1H, dd), 4.33 (2H, q), 1.33 (3H, t).

Description of D17

Ethyl 3-chloro-4-(2-methyl propyl)benzoate (D17)

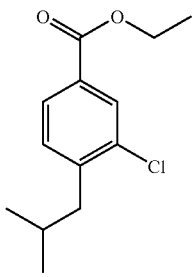

A solution of isobutylzinc bromide in THF (0.5 M, 30 mL, 15.0 mmol) was added under argon to ethyl 4-bromo-3-chlorobenzoate (D16) (2.00 g, 7.60 mmol) and then 1,1'-bis(diphenylphosphino)ferrocene-palladium(II) dichloride dichloromethane complex (930 mg, 1.14 mmol) was added. The reaction was heated to reflux for 4.5 h. The mixture concentrated in vacuo and the residue partitioned between ethyl acetate (125 mL) and water (125 mL). A solid formed, which was filtered off and discarded. The organic layer was washed with water (100 mL), dried (phase separator) and concentrated in vacuo. The crude product was purified by silica chromatography, eluting with 0-5% EtOAc in hexane over 30 minutes to give the title compound as a colourless oil (1.76 g, 7.33 mmol). δH (d$_6$-DMSO, 400 MHz): 7.91 (1H, d), 7.80 (1H, dd), 7.46 (1H, d), 4.30 (2H, q), 2.66 (2H, d), 1.88-2.01 (1H, m), 1.32 (3H, t), 0.89 (6H, d).

Description of D18

3-Chloro-4-(2-methylpropyl)benzoic acid (D18)

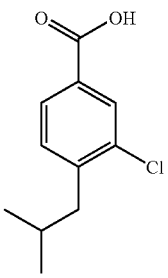

A solution of ethyl 3-chloro-4-(2-methylpropyl)benzoate (D17) (1.76 g, 7.33 mmol), and aqueous sodium hydroxide (2M, 3.70 mL, 7.4 mmol) in ethanol (30 mL) was heated at 40° C. for 3 h. The reaction mixture was concentrated in vacuo and the residue partitioned between ethyl acetate (100 mL) and water (100 mL), the latter acidified with 2M HCl (4 mL). The aqueous layer was extracted with ethyl acetate (100 mL) and the combined organic extracts dried (phase separator) and concentrated in vacuo to give the title compound as a white solid (1.35 g, 6.36 mmol). MS (ES): $C_{11}H_{13}{}^{35}ClO_2$ requires 212; found 211 (M−H$^+$).

Description of D19

Methyl 3-cyano-4-{[(trifluoromethyl)sulfonyl]oxy}benzoate (D19)

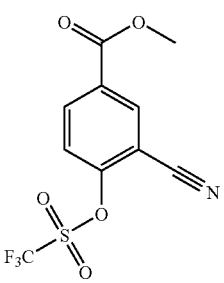

To a solution of methyl 3-cyano-4-hydroxybenzoate (3 g, 16.93 mmol) and triethylamine (3.54 ml, 25.4 mmol) in dry dichloromethane (60 ml) at 0° C. under a flush of argon was added trifluoromethanesulfonic anhydride (3.15 ml, 18.63 mmol) slowly dropwise. The reaction was allowed to warm to room temperature and stirred for 1 h. The reaction mixture was washed with 10% aqueous potassium carbonate (2×50 mL) and then aqueous HCl (2M, 2×50 mL) before the organic phase was dried (phase separator) and the solvent removed in vacuo to give the title compound as a dark brown oil, (5.165 g, 16.70 mmol). δH (CDCl$_3$, 400 MHz): 8.44 (1H, d), 8.38 (1H, dd), 7.60 (1H, d), 3.99 (3H, s).

Description of D20

Methyl 2-cyano-4-biphenylcarboxylate (D20)

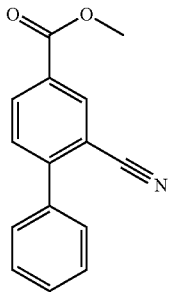

The following reaction was split into two batches with half the amounts: methyl 3-cyano-4-{[(trifluoromethyl)sulfonyl]oxy}benzoate (D19) (1.5 g, 4.85 mmol), phenylboronic acid (1.183 g, 9.70 mmol), potassium carbonate (2.011 g, 14.55 mmol) and palladium tetrakistriphenylphosphine(0) (0.561 g, 0.485 mmol) were dissolved in DMF (24 ml) and the mixture heated in the microwave for 30 min at 150° C. The two reactions were combined and diluted with ethyl acetate (50 mL) and the mixture filtered through kieselguhr to remove palladium residues. The filtrate was concentrated in vacuo to reduce the amount of DMF and then the residue partitioned between saturated aqueous sodium bicarbonate (50 mL) and ethyl acetate (50 mL). The organic phase was washed with further sodium bicarbonate (50 mL) and then water (50 mL) before it was dried (MgSO$_4$), filtered and the solvent removed in vacuo. The brown solid was purified by silica chromatography, eluting with 0-25% EtOAc in iso-hexane over 35 minutes to give the title compound as a white solid (935 mg, 3.94 mmol). δH (d$_6$-DMSO, 400 MHz): 8.42 (1H, d), 8.29 (1H, dd), 7.81 (1H, d), 7.65 (2H, m), 7.60-7.50 (3H, m), 3.92 (3H, s).

Description of D21

2-Cyano-4-biphenylcarboxylic acid (D21)

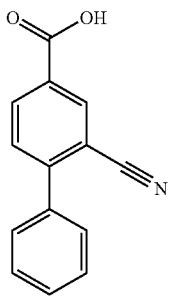

To methyl 2-cyano-4-biphenylcarboxylate (D20) (935 mg, 3.94 mmol) was added ethanol (18 ml) but dissolution did not occur so dichloromethane (10 ml) was added. 2M aqueous sodium hydroxide (2 ml, 4.00 mmol) was then added and the reaction stirred for 2 h. To the mixture was added dichloromethane (20 mL) and 2M aqueous HCl (10 mL). The layers were separated and the aqueous extracted with further dichloromethane (20 mL). The combined organic phase was dried (phase separator) and the solvent removed in vacuo to give a white solid, which was dissolved in methanol (30 mL) and aqueous sodium hydroxide was added (2M, 3 mL). The reaction was stirred at room temperature for 1 h before addition of water (20 mL). The reaction was stirred for a further 1 h. Dichloromethane (60 mL) was added and the mixture shaken and the layers separated. The aqueous phase was extracted with further dichloromethane (50 mL) before the combined organic phase was dried (phase separator) and the solvent removed in vacuo to give the title compound as a white solid, (849 mg, 3.80 mmol). MS (ES): $C_{14}H_9NO_2$ requires 223; found 222 (M–H$^+$).

Description of D22

Ethyl 4-chloro-3-(trifluoromethyl)benzoate (D22)

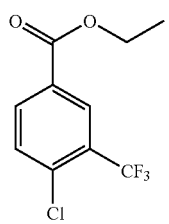

4-Chloro-3-(trifluoromethyl)benzoic acid (1 g, 4.45 mmol) was dissolved in ethanol (3 ml) and concentrated sulfuric acid (0.15 ml) was added. The mixture was heated in the microwave at 100° C. for 5 minutes and then 120° C. for 15 minutes. The solvent was removed in vacuo and the residue partitioned between saturated aq. sodium bicarbonate (50 ml) and ethyl acetate (50 ml). The aqueous layer was extracted with further EtOAc (50 ml) and the organic phases were combined, dried with a phase separator and concentrated in vacuo to give the title compound (1.026 g) as a colourless oil. δH (methanol-d$_4$, 400 MHz) 1.40 (3H, t), 4.41 (2H, q), 7.76 (1H, d), 8.21 (1H, dd), 8.33 (1H, d).

Description of D22 (Alternative Procedure)

Ethyl 4-chloro-3-(trifluoromethyl)benzoate (D22)

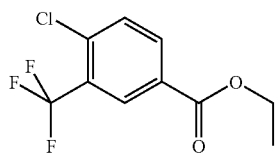

A solution of 4-chloro-3-trifluoromethyl benzoic acid (10 g, 44.5 mmol) in ethanol (10 ml) was split equally between two microwave vials. Concentrated sulfuric acid (0.75 ml) was added to each vial (1.5 ml in total). The reactions were heated in the microwave at 120° C. for 30 minutes in total. The reaction mixtures were combined and concentrated in vacuo. The residue was partitioned between EtOAc (100 ml) and aq. sodium bicarbonate (100 ml), the organic phase was separated, washed with aq. sodium bicarbonate (100 ml) and water (2×100 ml) and then dried (phase separator) and the solvent removed in vacuo to give the title compound (4.126 g) as a colourless oil. δH (400 MHz, methanol-$d_4$) consistent with previous example.

Description of D23

2-(Trifluoromethyl)-4-biphenylcarboxylic acid (D23)

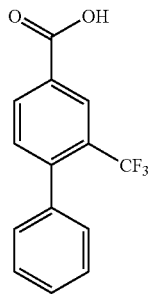

The reaction was split into 4, using a quarter of the reagents in each: to a mixture of 4-bromo-3-(trifluoromethyl)benzonitrile (4 g, 16.00 mmol), phenylboronic acid (3.90 g, 32.0 mmol) and potassium carbonate (6.63 g, 48.0 mmol) in N,N-dimethylformamide (DMF) (64 ml) was added palladium tetrakistriphenylphosphine(0) (1.849 g, 1.600 mmol). Each reaction was heated in the microwave at 150° C. for 30 min. The combined reaction mixtures were filtered through celite, washed with ethyl acetate and the solvent removed in vacuo. The residue was partitioned between ethyl acetate (100 mL) and water (100 mL) and the organic phase washed with sodium bicarbonate solution (100 mL). The organic phase was dried (MgSO$_4$), filtered and the solvent removed in vacuo. The brown oil was triturated with dichloromethane and filtered to give a pale yellow solid, 2-(trifluoromethyl)-4-biphenylcarboxamide (2.47 g) which was used without further purification. To 2-(trifluoromethyl)-4-biphenylcarboxamide (2 g, 7.54 mmol) in ethanol (80 ml) was added potassium hydroxide (4.23 g, 75 mmol) and water and the mixture heated to 90° C. for 18 h. The reaction mixture was concentrated in vacuo and the residue partitioned between dichloromethane (100 mL) and 2M HCl (100 mL). The organic phase was isolated and dried (phase separator) and the solvent removed in vacuo to give the crude product. Purification using the Biotage Horizon, reverse phase cartridge, eluting 5-100% MeCN in water gave as an off-white solid the title compound (960 mg). MS (ES): $C_{14}H_9F_3O_2$ requires 266; found 265 (M−H$^+$).

Description of D23 (Alternative Procedure)

2-(Trifluoromethyl)-4-biphenylcarboxylic acid (D23)

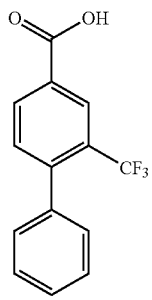

Batch A: A mixture of Ethyl 4-chloro-3-(trifluoromethyl) benzoate (D22) (1.0 g, 3.96 mmol), phenyl boronic acid (724 mg, 5.94 mmol), palladium acetate (44 mg), (dicyclohexylphosphino)biphenyl (140.2 mg) and potassium fluoride (689 mg, 11.9 mmol) in THF (8 ml) was heated in the microwave at 120° C. for a total of 40 minutes.

Batch B: A mixture of Ethyl 4-chloro-3-(trifluoromethyl) benzoate (D22) (500 mg, 1.98 mmol), phenyl boronic acid (290 mg, 2.38 mmol), palladium acetate (2.2 mg), (dicyclohexylphosphino)biphenyl (7 mg) and potassium fluoride (344 mg, 5.8 mmol) in THF (4 ml) was heated in the microwave at 120° C. for 20 minutes.

The reaction mixtures from batches A & B were combined filtered and the filtrate concentrated in vacuo. The residue was purified by flash chromatography (SiO$_2$, 0 to 5% EtOAc in hexane) to give a mixture of starting material and coupled product. This material was dissolved in ethanol (10 ml) and 2M NaOH (aq) (5 ml) and then heated to reflux for 3 h. The solvent was removed in vacuo and the residue partitioned between DCM and 2M aq. HCl. The aqueous layer was extracted with further DCM. The organic phases were combined and concentrated in vacuo. The crude material was purified by reversed phase chromatography on the Horizon eluting with 5 to 100% MeCN in water to afford the title compound as a white solid (367 mg) (DN108121-170A2, GSK1869780A). MS (ES): $C_{14}H_9F_3O_2$ requires 266; found 265 (M−H$^+$).

Description of D24

Methyl 3-cyano-4-(2-methylpropyl)benzoate (D24)

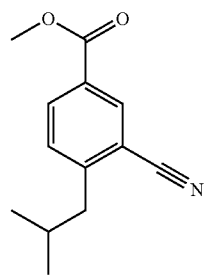

To methyl 3-cyano-4-{[(trifluoromethyl)sulfonyl]oxy}benzoate (D19) (1.5 g, 4.85 mmol) was added bromo(2-methylpropyl)zinc (48.5 ml, 24.25 mmol) in tetrahydrofuran (50 ml) under argon. To the solution was then added 1,1'-bis(diphenylphosphino)ferrocenedichloro palladium(II) dichloromethane complex (0.355 g, 0.485 mmol) and the reaction heated to reflux for 6 h. The mixture was quenched with water (2 mL) and then filtered through celite, washing with ethyl acetate. The solvent was removed in vacuo. The residue was partitioned between ethyl acetate (50 mL) and water (50 mL) and the organic phase dried (phase separator) and the solvent removed in vacuo. The residue was purified by silica chromatography, eluting 0-15% EtOAc in iso-hexane over 40 min. Two batches were collected, one of which was the title compound as a colourless oil (233 mg, 1.072 mmol). δH (CDCl$_3$, 400 MHz): 8.28 (1H, d), 8.15 (1H, dd), 7.38 (1H, d), 3.94, 3H, s), 2.78 (2H, d), 2.02 (1H, m), 0.96 (6H, d).

39

Description of D25

3-Cyano-4-(2-methylpropyl)benzoic acid (D25)

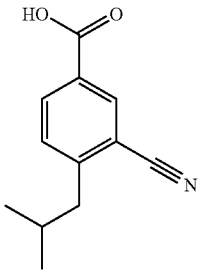

Methyl 3-cyano-4-(2-methylpropyl)benzoate (D24) (233 mg, 1.072 mmol) was dissolved in ethanol (4 ml) and 2M aqueous sodium hydroxide (1 ml, 2 mmol) was added. The reaction was stirred for 1 h. 2M aqueous HCl (10 mL) was added and the mixture extracted with dichloromethane (20 mL+10 mL). The organic phases were isolated and dried by phase separator and combined before the solvent was removed in vacuo to give the title compound as a white solid (203 mg, 0.999 mmol). MS (ES): $C_{12}H_{13}NO_2$ requires 203; found 202 (M−H$^+$).

Description of D26

5-Formyl-2-{[(1S)-1-methylpropyl]oxy}benzonitrile (D26)

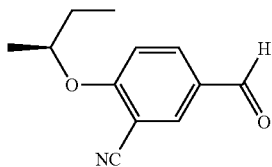

(2S)-2-Butanol (0.99 g, 0.013 mol) was dissolved in DMF (50 ml) and the solution cooled to 0° C. To this was added sodium hydride, (60% dispersion in mineral oil, 1.54 g, 0.036 mol) in a portion-wise manner, the mixture was stirred at 0° C. for 10 minutes after complete addition. 2-Fluoro-5-formyl-benzonitrile (2.0 g, 0.013 mol) was then added and the reaction mixture allowed to warm to room temperature (slowly within the ice bath) and the reaction mixture was stirred overnight at room temperature. The reaction mixture was then cooled to 0° C., quenched with brine and diluted with EtOAc (~25 ml). The mixture was partitioned and the organic fraction extracted with water (~30 ml), the combined organics were dried by passing through a phase separating cartridge and then evaporated to dryness under reduced pressure to give the crude product. The crude residue was purified on a 40+M Biotage cartridge, eluting with a 20 to 50% mixture of EtOAc in hexane. This gave the title compound (220 mg) as a white solid. MS (ES): $C_{12}H_{13}NO_2$ requires 203; found 204 (MH$^+$).

40

Description of D27

3-Cyano-4-{[(1S)-1-methylpropyl]oxy}benzoic acid (D27)

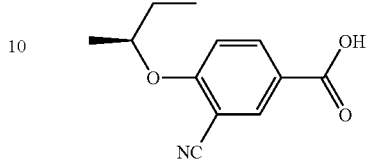

To a solution of 5-formyl-2-{[(1S)-1-methylpropyl]oxy}benzonitrile (D26) (220 mg, 1.08 mmol) in acetic acid (20 ml) was added sodium perborate tetrahydrate (334 mg, 2.17 mmol), the reaction mixture was heated at 50° C. over the weekend. The reaction mixture was concentrated in vacuo. Water (~50 ml) was added, EtOAc (~30 ml) was added and the layers partitioned, the aqueous layer was extracted twice more with EtOAc (~30 ml) and the combined organics were evaporated to dryness under reduced pressure to give the title compound (245 mg) as an off-white solid. MS (ES): $C_{12}H_{13}NO_2$ requires 219; found 220 (MH$^+$).

Description of D28

5-Formyl-2-{[(1R)-1-methylpropyl]oxy}benzonitrile (D28)

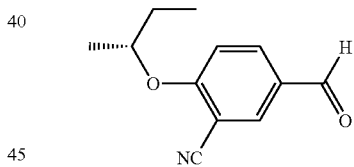

(2R)-2-Butanol (0.99 g, 0.013 mol) was dissolved in DMF (50 ml) and the solution cooled to 0° C. To this was added sodium hydride, 60% dispersion in mineral oil (1.54 g, 0.036 mol) in a portion-wise manner, the mixture was stirred at 0° C. for 10 minutes after complete addition. 2-Fluoro-5-formyl-benzonitrile (2.0 g, 0.013 mol) was then added and the reaction mixture allowed to warm to room temperature (slowly within the ice bath) and the reaction mixture was stirred overnight at room temperature. The reaction mixture was then cooled to 0° C., quenched with brine and diluted with EtOAc (~25 ml). The mixture was partitioned and the organic fraction extracted with water (~30 ml), the combined organics were dried by passing through a phase separating cartridge and evaporated to dryness under reduced pressure to give the crude product. The crude residue was purified on a 40+M Biotage cartridge, eluting with a 20 to 50% mixture of EtOAc in hexane. This gave the title compound (310 mg) as a yellow oil. δH (d$_6$-DMSO, 400 MHz): 9.88 (1H, s), 8.30 (1H, s), 8.15 (1H, d), 7.49 (1H, d), 4.73-4.81 (1H, m), 1.63-1.79 (2H, m), 1.33 (3H, d), 0.95 (3H, t).

Description of D29

3-Cyano-4-{[(1R)-1-methylpropyl]oxy}benzoic acid (D29)

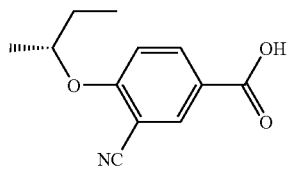

To a solution of 5-formyl-2-{[(1R)-1-methylpropyl]oxy}benzonitrile (D37) (310 mg, 1.53 mmol) in acetic acid (30 ml) was added sodium perborate tetrahydrate (471 mg, 3.05 mmol), the reaction mixture was heated at 50° C. over the weekend. The reaction mixture was concentrated in vacuo and water (~50 ml) added, EtOAc (~30 ml) was added and the layers partitioned, the aqueous layer was extracted twice more with EtOAc (~30 ml) and the combined organics evaporated to dryness under reduced pressure to give the title compound (315 mg) as an off-white solid. MS (ES): C$_{12}$H$_{13}$NO$_2$ requires 219; found 220 (MH$^+$).

Description of D30

1-Methylethyl 5-chloro-6-[(1-methylethyl)oxy]-3-pyridinecarboxylate (D30)

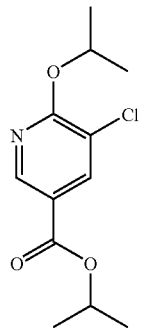

5-Chloro-6-hydroxy-3-pyridinecarboxylic acid (3.00 g, 17.28 mmol) was suspended in toluene (75 ml) and treated with silver carbonate (12.4 g, 24.8 mmol) and 2-iodopropane (6.9 ml, 69.12 mmol) and stirred at RT in the dark for 18 hours. The mixture was filtered and the filtrate evaporated to give the title compound with impurities (1.32 g). δH (d$_6$-DMSO) 1.31 (6H, d), 1.35 (6H, d), 5.13 (1H, sept), 5.40 (1H, sept), 8.22 (1H, d), 8.65 (1H, d).

Description of D30 (Alternative Procedure)

1-Methylethyl 5-chloro-6-[(1-methylethyl)oxy]-3-pyridinecarboxylate (D30)

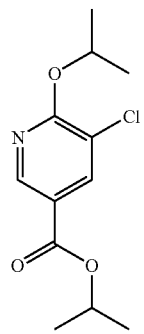

5-Chloro-6-hydroxy-3-pyridinecarboxylic acid (1 g, 5.76 mmol) was suspended in toluene (200 ml) and treated with silver carbonate (3.97 g, 14.40 mmol) and 2-iodopropane (3.46 ml, 34.6 mmol) and stirred at RT in the dark for 3 days. Added further 2-iodopropane (3 ml) and stirred for 24 hours. Added EtOAc (200 ml) and washed with water (200 ml) and saturated NaHCO$_3$ (50 ml) followed by water (200 ml). Dried over MgSO$_4$ and evaporated off the solvent to yield 1.0 g of the title compound as a clear, colourless oil used without further characterisation.

Description of D30 (Alternative Procedure)

1-Methylethyl 5-chloro-6-[(1-methylethyl)oxy]-3-pyridinecarboxylate (D30)

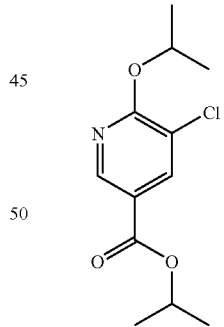

2-Iodopropane (12.42 ml, 124 mmol) was added to a suspension of 5-chloro-6-hydroxy-3-pyridinecarboxylic acid (commercially available from Fluka, 5.4 g, 31.1 mmol) and Ag$_2$CO$_3$ (21.45 g, 78 mmol) in CHCl$_3$ (200 ml) and the reaction was stirred at room temperature for 3 days. The precipitate was filtered off and the solvent was removed in vacuo to give the title compound (4 g, 47%) as a yellow oil which was used in the next step without further purification. MS (ES) C$_{12}$H$_{16}$ClNO$_3$ requires 257, found 258 [M–H]$^+$

Description of D31

5-Chloro-6-[(1-methylethyl)oxy]-3-pyridinecarboxylic acid (D31)

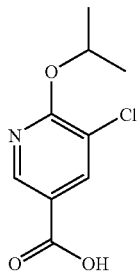

1-Methylethyl 5-chloro-6-[(1-methylethyl)oxy]-3-pyridinecarboxylate (D30) (1.6 g, 6.21 mmol) in isopropanol (70 ml) and water (35.0 ml) was treated with 2N sodium hydroxide (6.21 ml, 12.42 mmol) and stirred for 3 hours to give a single product. Evaporated off the IPA, acidified with glacial acetic acid and extracted product into EtOAc (100 ml). Dried over MgSO$_4$ and evaporated off the solvent to yield 1.30 g of the title compound as a white solid. MS (ES) C$_9$H$_{10}$$^{35}$ClNO$_3$ requires 215; found 214 (M−H$^+$).

Description of D31 (Alternative Procedure)

5-Chloro-6-[(1-methylethyl)oxy]-3-pyridinecarboxylic acid (D31)

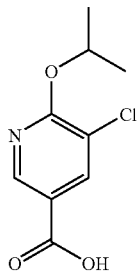

Sodium hydroxide (29.1 ml, 58.2 mmol) was added to a solution of 1-methylethyl 5-chloro-6-[(1-methylethyl)oxy]-3-pyridinecarboxylate (D30) (3 g, 11.64 mmol) in methanol (25 ml) and stirred at room temperature overnight. The solvent was evaporated before neutralising with 2M HCl and extracting with ether. It was then dried over magnesium sulfate and evaporated to give an impure white solid. Trituration with DCM gave the title compound as a pure white solid. MS (ES) C$_9$H$_{10}$ClNO$_3$ requires 215, found 216 [M+H]$^+$

Description of D32

4-(1-Cyclohexen-1-yl)-3-(trifluoromethyl)benzamide (D32)

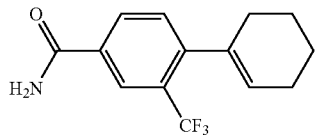

4-Bromo-3-(trifluoromethyl)benzonitrile (commercial) (1.2 g, 4.80 mmol), 1-cyclohexen-1-ylboronic acid (0.907 g, 7.20 mmol), sodium methoxide (0.778 g, 14.40 mmol) and bis(triphenylphosphine)palladium(II) chloride (0.337 g, 0.480 mmol) were added to dry methanol (12 mL) and the mixture heated in the microwave at 80° C. for 10 minutes. The reaction mixture was partitioned between ethyl acetate (40 mL) and water (40 mL) and then the organic phase washed with further water (40 mL). The organic phase was dried (MgSO$_4$), filtered and the solvent removed in vacuo. The crude product was purified by flash silica chromatography, eluting with 0-75% ethyl acetate in hexane to give the title compound as a white solid (1.02 g). MS (ES): C$_{14}$H$_{14}$F$_3$NO requires 269; found 270 (MH$^+$).

Description of D33

4-Cyclohexyl-3-(trifluoromethyl)benzamide (D33)

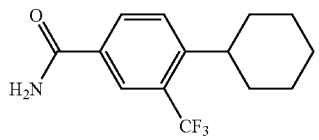

4-(1-Cyclohexen-1-yl)-3-(trifluoromethyl)benzamide (D32) (850 mg, 3.16 mmol) was dissolved in methanol (63 ml) and hydrogenated using an H-Cube, using palladium on carbon at 40° C. with a flow rate of 2 mL/min. The solvent was removed in vacuo to give the title compound as a white solid (822 mg). MS (ES): C$_{14}$H$_{16}$F$_3$NO requires 271; found 272 (MH$^+$).

Description of D34

4-Cyclohexyl-3-(trifluoromethyl)benzoic acid (D34)

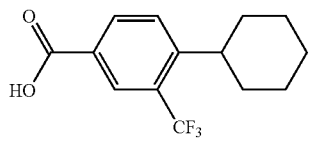

To a solution of 4-cyclohexyl-3-(trifluoromethyl)benzamide (D33) (822 mg, 3.03 mmol) in ethanol (40 ml) was added potassium hydroxide (1.700 g, 30.3 mmol) and water (5 ml) and the reaction heated to 90° C. block temperature for 3 h and stirred at room temperature for 16 h. Further potassium hydroxide (1.700 g, 30.3 mmol) was added and the reaction heated at reflux for 27 h. A further 5 mL of water was added and the reaction heated for 66 hours (weekend). The reaction mixture was concentrated in vacuo and the residue partitioned between ethyl acetate (25 mL) and aqueous hydrochloric acid (2M, 25 mL). The aqueous layer was further extracted with ethyl acetate (25 mL) and the combined organic phases dried (MgSO$_4$), filtered and the solvent removed in vacuo to give the title compound as a white solid (737 mg). MS (ES): $C_{14}H_{15}F_3O_2$ requires 272; found 271 (M−H$^+$).

Description of D35

1-Methylethyl 4-[(1-methylethyl)oxy]-3-(trifluoromethyl)benzoate (D35)

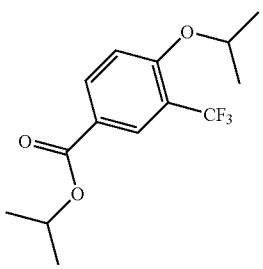

A mixture of 4-hydroxy-3-(trifluoromethyl)benzoic acid (commercial) (450 mg, 2.18 mmol), 2-iodopropane (435 μL, 4.36 mmol) and potassium carbonate (603 mg, 4.36 mmol) in N,N'-dimethylformamide (40 mL) was heated at 70° C. for 4 h before further 2-iodopropane (218 μL, 2.18 mmol) was added and the heating continued for 18 h. The inorganic solid was filtered off and rinsed with ethyl acetate. The filtrate was concentrated in vacuo and partitioned between ethyl acetate (150 mL) and water (150 mL) containing some aqueous sodium hydroxide. The organic layer was dried (phase separator) and concentrated in vacuo to give the crude title compound (704 mg) as a yellow oil. MS (ES): $C_{14}H_{17}F_3O_3$ requires 290; found 291 (MH$^+$).

Description of D36

4-[(1-Methylethyl)oxy]-3-(trifluoromethyl)benzoic acid (D36)

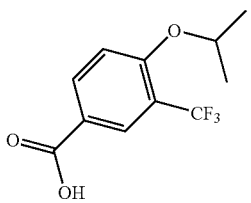

To a mixture of 1-methylethyl 4-[(1-methylethyl)oxy]-3-(trifluoromethyl)benzoate (D35) (704 mg, 2.43 mmol) in ethanol (110 mL) was added aqueous sodium hydroxide (2M, 12.2 mL, 24.3 mmol) and the reaction heated to reflux for 1 h. The mixture was concentrated in vacuo and the residue partitioned between ethyl acetate (100 mL) and water (100 mL) and acidified with aqueous hydrochloric acid (2M, 13 mL). The aqueous layer was extracted further with ethyl acetate (100 mL) and the combined organic layers dried and concentrated in vacuo to give the title compound as a yellow solid (563 mg). MS (ES): $C_{11}H_{11}F_3O_3$ requires 248; found 247 (M−H$^+$).

Description of D37

Methyl 3-chloro-4-(propyloxy)benzoate (D37)

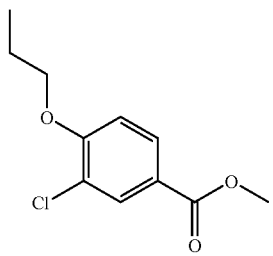

Methyl 4-hydroxy-3-chlorobenzoate (10 g, 53.6 mmol) was dissolved in DMF (110 ml) and then potassium carbonate (14.8 g, 107.2 mmol) was added followed by n-propyliodide (10.4 ml, 107.2 mmol). The reaction was heated to 70° C. overnight, filtered and then the fitrate was partitioned between EtOAc and water. The organic layer was separated, dried and evaporated to give the title compound as a yellow oil (12.37 g). MS (ES) $C_{11}H_{13}{}^{35}ClO_3$ requires 228; found 229 (MH$^+$).

Description of D38

3-Chloro-4-(propyloxy)benzoic acid (D38)

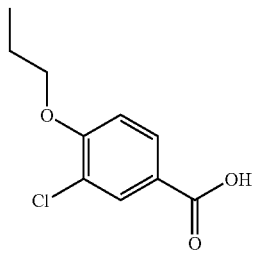

A solution of methyl 3-chloro-4-(propyloxy)benzoate (D37) (RD108825-58-B1) (12.22 g, 0.053 mol) in ethanol (40 ml) and 2M NaOH aq. (40 ml) was heated at 60° C. for 3 hours. The reaction was allowed to cool and then left at room temperature over the weekend. The reaction mixture was poured into a mixture of dilute aq. HCl and EtOAc. The organic layer was separated, dried and evaporated to give a solid which was triturated with ether to give the title compound as a white solid (7.7 g). MS (ES) $C_{10}H_{11}{}^{35}ClO_3$ requires 214; found 213 (M−H$^+$).

Description of D39

Ethyl 3-chloro-4-(1-pyrrolidinyl)benzoate (D39)

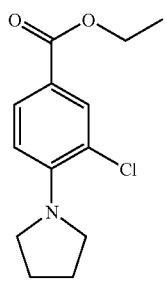

A mixture of ethyl 4-bromo-3-chlorobenzoate (D16) (2.53 g, 9.62 mmol), pyrrolidine (1.03 mL, 12.5 mmol), sodium tert-butoxide (1.29 g, 13.5 mmol), BINAP (196 mg, 0.29 mmol) and tris(dibenzylideneacetone)dipalladium(0) (58 mg, 0.10 mmol) in toluene (120 mL) was heated to reflux under argon for 3 h. The reaction was allowed to cool and was filtered. The solid was washed with toluene and then the filtrate was concentrated. The residue was partitioned between ethyl acetate (150 mL) and water (100 mL) with aqueous sodium bicarbonate (50 mL) added. The organic phase was dried (phase separator) and concentrated to give an orange oil. The oil was purified by reverse phase chromatography, eluting 5-100% acetonitrile in water to give the title compound as an orange oil (600 mg). This contained some impurities. MS (ES): $C_{13}H_{16}{}^{35}ClNO_2$ requires 253; found 254 (MH$^+$).

Further title compound (85 mg) was made by a similar method.

Description of D40

3-Chloro-4-(1-pyrrolidinyl)benzoic acid (D40)

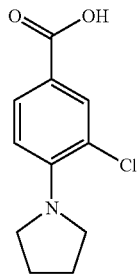

A mixture of ethyl 3-chloro-4-(1-pyrrolidinyl)benzoate (D39) (685 mg, 2.71 mmol) and aqueous sodium hydroxide (2M, 1.36 mL, 2.72 mmol) in ethanol (15 mL) was heated at 40° C. for 17 h. Further sodium hydroxide (1.36 mL, 2.72 mmol) was added and the reaction heated for a further 8 h. The mixture was concentrated and the residue dissolved in water (100 mL). The aqueous phase was washed with ethyl acetate (2×100 mL) and then acidified to pH 6. A white solid formed and hence was filtered off, washed with water and dried in a vacuum oven to give the title compound as an off-white solid (362 mg). MS (ES): $C_{11}H_{12}{}^{35}ClNO_2$ requires 225; found 226 (MH$^+$).

Description of D41

2-(Cyclopentyloxy)-5-formylbenzonitrile (D41)

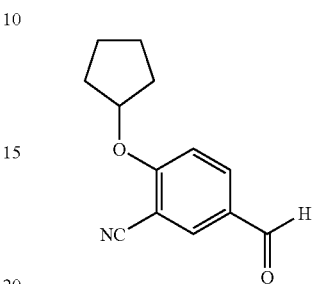

A solution of cyclopentanol (1.15 g, 0.013 mol), in DMF (50 ml) was cooled to 0° C. Sodium hydride (1.54 g, 0.016 mol) was added portionwise to the solution and the mixture stirred at 0° C. for 10 minutes after complete addition. 3-Cyano-4-fluorobenzaldehyde (commercial) (2.0 g, 0.013 mol) was then added and the mixture allowed to warm to room temperature and stirred overnight. The reaction mixture was cooled to 0° C. and brine was added, the mixture was diluted with ethyl acetate (~25 ml) and partitioned, the organic layer was washed with water (~30 ml) and passed through a phase separating cartridge to dry. The solution was concentrated in vacuo and the residue purified by Biotage SP4, 40M with 20-60% ethylacetate/hexane as eluant. The product containing fractions were concentrated in vacuo to yield the title compound (1.02 g, 4.2 mmol) as a yellow liquid. MS (ES): requires $C_{13}H_{13}NO_2$ 215; found 216 (MH$^+$).

Description of D42

3-Cyano-4-(cyclopentyloxy)benzoic acid (D42)

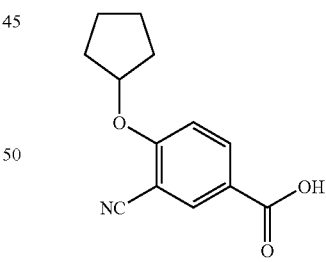

To a solution of (D41) (0.13 g, 0.604 mmol) in acetic acid (20 ml) at 50° C. was added sodium perborate tetrahydrate (0.186 g, 1.208 mmol) portion-wise. The reaction mixture was stirred at 50° C. overnight. Stirring was continued at 50° C. for 48 h, sodium perborate tetrahydrate (0.093 g, 0.604 mmol) was added to the reaction mixture and stirring continued for a further 2 days, the reaction mixture was then left to stand for 2 days at room temperature.

The solvent was removed in vacuo and the mixture partitioned between ethyl acetate (~20 ml) and water (~20 ml), the aqueous layer was extracted with ethyl acetate (2×~15 ml) and the combined organic layers were concentrated in vacuo to yield the title compound (106 mg, 0.435 mmol) as a yellow solid. MS (ES): requires $C_{13}H_{13}NO_3$ 231; found 230 (M-H$^+$).

Description of D43

5-[3-(1H-indazol-5-yl)-1,2,4-oxadiazol-5-yl]-2-[(1-methylethyl)oxy]benzonitrile (D43)

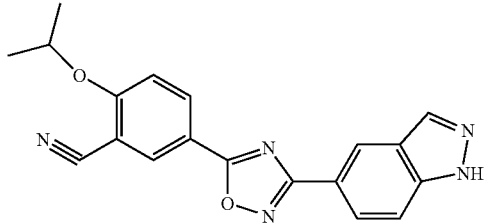

3-Cyano-4-[(1-methylethyl)oxy]benzoic acid (can be prepared as described in WO2005/58848) (1.52 g), EDAC (2.14 g) and HOBt (1.51 g) were dissolved in DMF (30 ml) and then stirred for 5 minutes. N-hydroxy-1H-indazole-5-carboximidamide (D2) (1.3 g) was added and the reaction was heated to 80° C. for 6 hours and left to cool overnight. The solvent was removed in vacuo and the crude was partitioned between EtOAc and aq. sodium bicarbonate. The organic layer was separated, dried and evaporated to dryness in vacuo. The resulting solid was triturated with ether and ethyl acetate, washed with methanol and ether to give the title compound (816 mg) as a pink solid. MS (ES): $C_{19}H_{15}N_5O_2$ requires 345; found (MH$^+$) 346

Description of D43 (Alternative Procedure)

5-[3-(1H-indazol-5-yl)-1,2,4-oxadiazol-5-yl]-2-[(1-methylethyl)oxy]benzonitrile (D43)

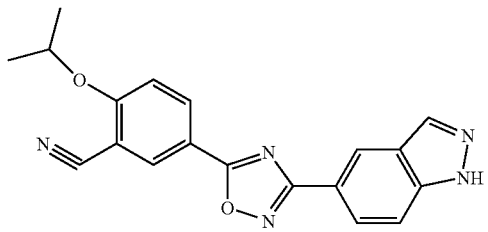

3-Cyano-4-[(1-methylethyl)oxy]benzoyl chloride (D106) (545 mg, 2.437 mmol) and N-hydroxy-1H-indazole-5-carboximidamide (D2) (685 mg, 2.437 mmol) were dissolved in acetonitrile (30 ml) before adding triethylamine (0.374 ml, 2.68 mmol). The resulting mixture was stirred at room temperature for 3 h then at 80° C. for 48 h, then cooled at room temperature. The precipitate formed was filtered off and dissolved in EtOAc and washed with water, evaporated and chromatographed [0-15% EtOAc in cyclohexane] to give the title compound (170 mg, 17%) as a pink solid. MS (ES): $C_{19}H_{15}N_5O_2$ requires 345; found (MH$^+$) 346

Description of D44 and D45

Ethyl 4-[5-(5-{3-cyano-4-[(1-methylethyl)oxy]phenyl}-1,2,4-oxadiazol-3-yl)-1H-methylethyl)oxy]phenyl}-1,2,4-oxadiazol-3-yl)-2H-indazol-2-yl]butanoate (D44) & ethyl 4-[5-(5-{3-cyano-4-[(1-methylethyl)oxy]phenyl}-1,2,4-oxadiazol-3-yl)-2H-indazol-2-yl]butanoate (D45)

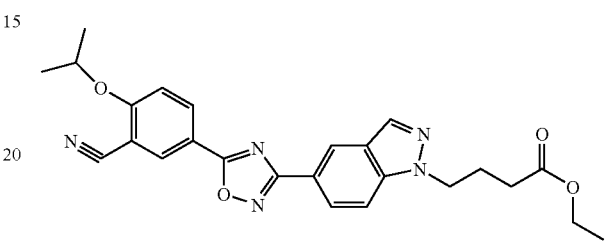

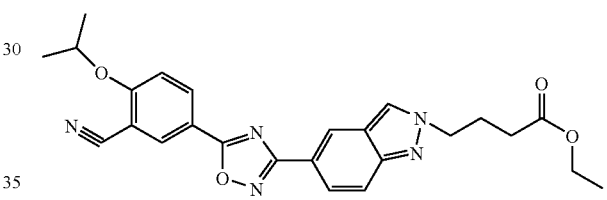

5-[3-(1H-indazol-5-yl)-1,2,4-oxadiazol-5-yl]-2-[(1-methylethyl)oxy]benzonitrile (D43) (200 mg, 0.58 mmol) was dissolved in DMF (5 ml) and $Cs_2CO_3$ (567 mg, 1.74 mmol) and ethyl 4-bromobutanoate (0.166 ml, 1.16 mmol) were added. The reaction was heated to 80° C. for 12 hours then allowed to cool. The reaction mixture was partitioned between water and EtOAc. The organic layer was separated, dried and evaporated in vacuo to generate the crude product which was purified by flash chromatography (EtOAc/petrol 1:6 to 1:1) to generate ethyl 4-[5-(5-{3-cyano-4-[(1-methylethyl)oxy]phenyl}-1,2,4-oxadiazol-3-yl)-1H-indazol-1-yl]butanoate (D44) (151 mg) as a white solid. δH (d$_6$-DMSO) 1.14 (3H, t), 1.39 (6H, d), 2.04-2.18 (2H, m), 2.31 (2H, t), 4.01 (2H, q), 4.51 (2H, t), 4.99 (1H, sept), 7.57 (1H, d), 7.87 (1H, d), 8.08 (1H, dd), 8.29 (1H, d), 8.43 (1H, dd), 8.52 (1H, d), 8.57-8.58 (1H, m). MS (ES): $C_{25}H_{25}N_5O_4$ requires 459; found (MH$^+$) 460 and RD108825-187A2 ethyl 4-[5-(5-{3-cyano-4-[(1-methylethyl)oxy]phenyl}-1,2,4-oxadiazol-3-yl)-2H-indazol-2-yl]butanoate (D45) (66 mg) as a white solid. 5H (d$_6$-DMSO) 1.16 (3H, t), 1.37 (6H, d), 2.14-2.26 (2H, m), 2.32 (2H, t), 4.03 (2H, q), 4.51 (2H, t), 4.99 (1H, sept), 7.57 (1H, d), 7.78-7.80 (1H, m), 7.89 (1H, dd), 8.42 (1H, dd), 8.52 (1H, d), 8.57-8.58 (1H, m), 8.62 (1H, s). MS (ES) $C_{25}H_{25}N_5O_4$ requires 459; found (MH$^+$) 460.

Description of D46

Ethyl [5-(5-{3-cyano-4-[(1-methylethyl)oxy]phenyl}-1,2,4-oxadiazol-3-yl)-1H-indazol-1-yl]acetate (D46)

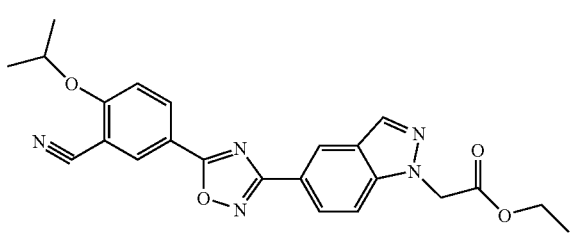

Prepared in a similar fashion to (D44) from 5-[3-(1H-indazol-5-yl)-1,2,4-oxadiazol-5-yl]-2-[(1-methylethyl)oxy]benzonitrile (D43) and ethyl bromoacetate. The crude material was purified by trituration with diethyl ether to give the title compound as a yellow solid. MS (ES) $C_{23}H_{21}N_5O_4$ requires 431; found (MH$^+$) 432.

Description of D47

Ethyl 3-(5-cyano-1H-indazol-1-yl)propanoate (D47)

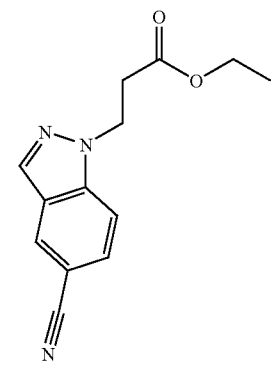

To a solution of 1H-indazole-5-carbonitrile (D1) (2.8 g, 19.72 mmol) in DMF (60 ml) was added cesium carbonate (12.86 g, 39.4 mmol) followed by ethyl 3-bromopropanoate (3.8 ml, 29.6 mmol). The reaction mixture was stirred at 80° C. for 3 hours and then allowed to cool. The solvent was removed in vacuo and the crude material was partitioned between EtOAc (×2) and water, the organics were combined, dried and evaporated. The crude was azeotroped with toluene and then purified by flash chromatography (EtOAc/hexane 1:3) to give 3.75 g of a pink solid which after trituration with hexane afforded the title compound (3.2 g) as a pink solid. MS (ES): $C_{13}H_{13}N_3O_2$ requires 243 found (MH$^+$) 244.

Description of D47 (Alternative Procedure)

Ethyl 3-(5-cyano-1H-indazol-1-yl)propanoate (D47)

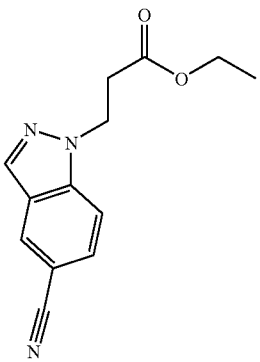

To a solution of 1H-indazole-5-carbonitrile (D1) (3.88 g, 27.3 mmol) in DMF (85 ml) was added $Cs_2CO_3$ (17.8 g, 54.6 mmol) and then ethyl 3-bromopropanoate (3.5 ml), 27 mmol) and ethyl 3-chloropropanoate (3.3 g, 24.2 mmol) were added. The reaction mixture was stirred at 80° C. for 4 hours and then allowed to cool. The solvent was removed in vacuo and the crude material was partitioned between EtOAc and water, the organics were separated, washed with brine, dried and evaporated. The crude was azeotroped with toluene and then purified by flash chromatography (EtOAc/hexane 1:9 to 1:1) to give 3.84 g of a yellow gum. MS data as for previous example.

Description of D47 (Alternative Procedure)

Ethyl 3-(5-cyano-1H-indazol-1-yl)propanoate (D47)

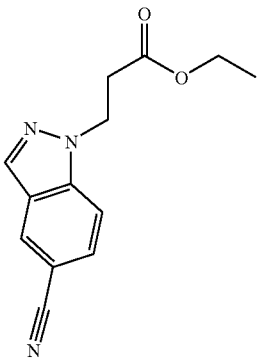

1H-indazole-5-carbonitrile (D1) (3.5 g, 24.45 mmol) was dissolved in N,N-dimethylformamide (60 ml). cesium carbonate (15.93 g, 48.9 mmol) and ethyl 3-bromopropanoate (4.68 ml, 36.7 mmol) were added. The mixture was heated at 80° C. for 4 hours. Diluted with EtOAc and washed with water (3×40 ml), dried over $MgSO_4$ and evaporated. The mixture was purified by flash chromatography, eluting EtOAc/iso-Hexane 10-30% then 10-20% to give (3.682 g) for the first isomer (yellow oil) and (1.509 g) for the second isomer (pink solid). Analysis of the first isomer by 1H nmr indicated that is was the 1-isomer contaminated with the 2-isomer (ca. 20%) δH (d$_6$-DMSO, 400 MHz) 1.05 (3H, t), 2.95 (2H, t), 3.97 (2H, q), 4.69 (2H, t), 7.74 (1H, dd), 7.92 (1H, dt), 8.28 (1H, d), 8.38 (1H, dd). MS (ES$^+$): C$_{13}$H$_{13}$N$_3$O$_2$ requires 243; found (MH$^+$) 244.

Description of D48

A Mixture of ethyl 4-(4-cyano-2H-indazol-2-yl)butanoate & ethyl 4-(4-cyano-1H-indazol-1-yl)butanoate (D48)

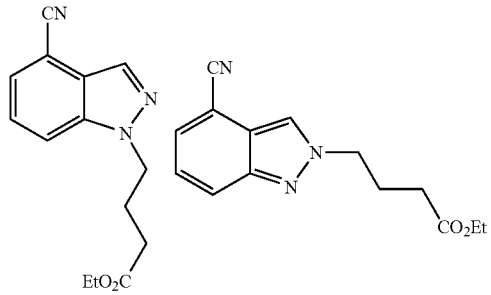

A mixture of ethyl 4-bromobutanoate (0.390 g, 1.998 mmol), 1H-indazole-4-carbonitrile (0.143 g, 0.999 mmol) and cesium carbonate (0.976 g, 3.00 mmol) in N,N-dimethylformamide (4 ml) was stirred and heated at 80° C. for 90 mins. Cooled, diluted with ethyl acetate/water (30 ml of each) and the organic washed with 3×15 ml of water, dried (magnesium sulphate), evaporated and purified by flash chromatography eluting with 1:2 ethyl acetate/hexane to give partial separation of the two isomers which after characterisation were recombined to give the title mixture of isomers (249 mg). δH (CDCl$_3$, 400 MHz) for 1-isomer: 1.24 (3H, t), 2.29 (4H, m), 4.12, (2H, q), 4.53 (2H, t), 7.45 (1H, dd), 7.54 (1H, dd), 7.71 (1H, dd), 8.19 (1H, d). δH (CDCl$_3$, 400 MHz) for 2-isomer 1.25 (3H, t), 2.35 (4H, m), 4.14, (2H, q), 4.58 (2H, t), 7.33 (1H, dd), 7.54 (1H, dd), 7.96 (1H, dd), 8.15 (1H, d).

Description of D48 (Alternative Procedure)

A mixture of ethyl 4-(4-cyano-2H-indazol-2-yl)butanoate & ethyl 4-(4-cyano-1H-indazol-1-yl)butanoate (D48)

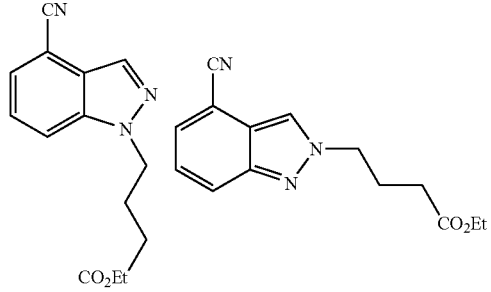

A mixture of ethyl 4-bromobutanoate (5.36 ml, 37.4 mmol), 1H-indazole-4-carbonitrile (2.68 g, 18.72 mmol) and cesium carbonate (18.30 g, 56.2 mmol) in N,N-dimethylformamide (50 ml) was heated at 80° C. for 90 mins. Cooled, diluted with EtOAc/water and the organic washed with 3×30 ml of water, dried (magnesium sulphate) and evaporated. Purified by flash chromatography eluting with EtOAc/hexane 1:3 to give the title mixture of isomers (4.7 g) as a yellow oil. MS (ES+): C$_{14}$H$_{15}$N$_3$O$_2$ requires 257; found (MH$^+$) 258.

Description of D49

A mixture of ethyl 3-(4-cyano-2H-indazol-2-yl)propanoate & ethyl 3-(4-cyano-1H-indazol-1-yl)propanoate (D49)

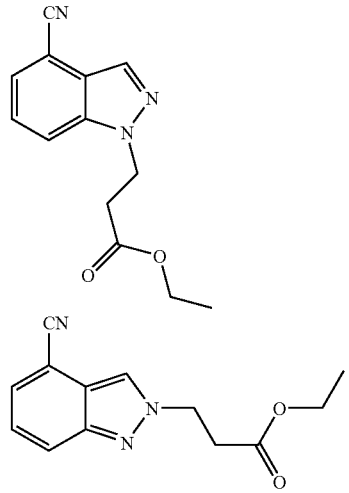

A mixture of ethyl 3-bromopropanoate (1.808 g, 9.99 mmol), 1H-indazole-4-carbonitrile (0.715 g, 4.99 mmol) and cesium carbonate (4.88 g, 14.98 mmol) in N,N-dimethylformamide (DMF) (10 ml) was stirred and heated at 80° C. for 2 hours. Cooled, diluted with ethyl acetate (40 ml) and water (40 ml) and the organic washed with 3×15 ml of water, dried (magnesium sulphate), evaporated and purified by flash chromatography eluting with 3:7 ethyl acetate/hexane to give 1.19 g of colourless oil which slowly crystallised to a white solid. NMR and LC/MS showed this to be a ~3:1 mix of isomers. MS (ES): C$_{13}$H$_{13}$N$_3$O$_2$ requires 243 found (MH$^+$) 244.

Description of D50 and D51

Ethyl 4-(5-cyano-1H-indazol-1-yl)butanoate (D50) and ethyl 4-(5-cyano-2H-indazol-2-yl)butanoate (D51)

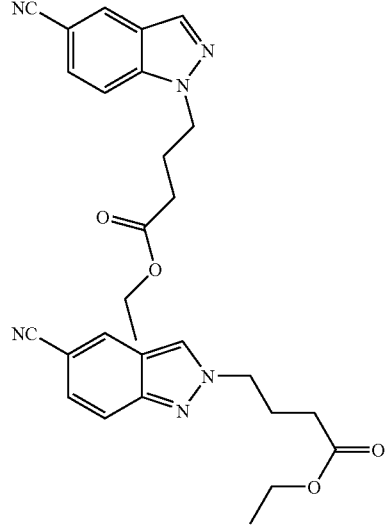

To a solution of 1H-indazole-5-carbonitrile (D1) (1.93 g, 13.59 mmol) in DMF (45 ml) was added cesium carbonate (9.1 g, 27.9 mmol) and then ethyl 4-bromobutanoate (2.92 ml, 20.4 mmol). The reaction was heated at 80° C. for 6 hours. Most of the DMF was removed in vacuo and the resultant material was partitioned between ethyl acetate and water, the organics were washed with brine, dried and evaporated to afford 4 g of a gum. The crude material was purified by flash chromatography using 1:4 EtOAc in hexane. The top running spot was isolated to afford RD107973-39B1 which was identified as ethyl 4-(5-cyano-1H-indazol-1-yl)butanoate (D50). δH (d$_6$-DMSO) 1.13 (3H, t), 2.04-2.13 (2H, m), 2.29 (2H, t), 3.99 (2H, q), 4.51 (2H, t), 7.74 (1H, dd), 7.88 (1H, d), 8.28 (1H, d), 8.41-8.44 (1H, m). MS (ES): $C_{14}H_{15}N_3O_2$ requires 257 found (MH$^+$) 258.

The lower running spot was isolated to afford the title compound. δH (d$_6$-DMSO) 1.15 (3H, t), 2.15-2.22 (2H, m), 2.31 (2H, t), 4.01 (2H, q), 4.49-4.55 (2H, m), 7.78 (1H, dd), 7.78 (1H, dd), 8.43-8.44 (1H, m), 8.67 (1H, d). $C_{14}H_{15}N_3O_2$ requires 257 found (MH$^+$) 258.

Description of D52

Ethyl 3-{5-[(hydroxyamino)(imino)methyl]-1H-indazol-1-yl}propanoate (D52)

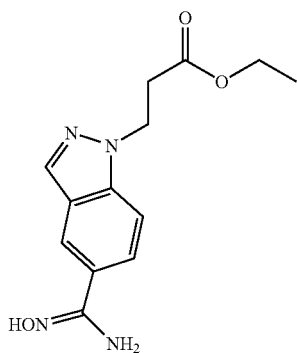

Ethyl 3-(5-cyano-1H-indazol-1-yl)propanoate (D47) (1 g, 4.11 mmol) was dissolved in ethanol (30 ml) and sodium bicarbonate (1.73 g, 20.55 mmol) and hydroxylamine hydrochloride (571 mg, 8.22 mmol) were added. The reaction was heated at 50° C. overnight and then allowed to cool. The reaction mixture was filtered and the residue washed with ethanol. The filtrate was evaporated to dryness in vacuo and the resultant crude title compound (1.06 g) was used the subsequent reactions.

Description of D52 (Alternative Procedure)

Ethyl 3-{5-[(hydroxyamino)(imino)methyl]-1H-indazol-1-yl}propanoate (D52)

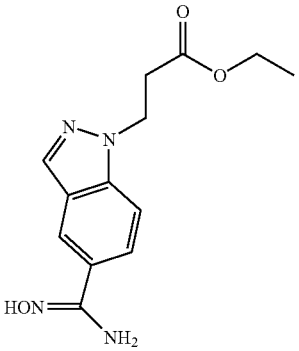

Ethyl 3-(5-cyano-1H-indazol-1-yl)propanoate (D47) (1 g, 4.11 mmol) was dissolved in ethanol (30 ml) and sodium bicarbonate (1.73 g, 20.88 mmol) and hydroxylamine hydrochloride (571 mg, 8.22 mmol) were added. The reaction was left at room temperature overnight and then heated to 50° C. for 4 hours then left to cool overnight. The reaction mixture was filtered and the residue washed with ethanol. The ethanolic filtrate was evaporated to dryness in vacuo and then triturated with ether to give the title compound (764 mg) as a white solid of approximately 90% purity. MS (ES): $C_{13}H_{16}N_4O_3$ requires 276; found (MH$^+$) 277.

Description of D52 (Alternative Procedure)

Ethyl 3-{5-[(hydroxyamino)(imino)methyl]-1H-indazol-1-yl}propanoate (D52)

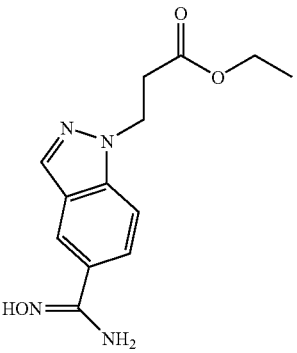

Ethyl 3-(5-cyano-1H-indazol-1-yl)propanoate (D47) (3.84 g, 15.8 mmol) was dissolved in ethanol (100 ml) and sodium bicarbonate (6.6 g, 79 mmol) and then hydroxylamine hydrochloride (3.3 g, 47.4 mmol) were added. The reaction was heated to 50° C. for a total of 11 hours and then left to cool overnight. The reaction was filtered and the residue washed with ethanol. The filtrate was evaporated to dryness in vacuo and the resultant solid triturated with ether to generate the title compound (3.79 g) as a white solid. MS (ES): $C_{13}H_{16}N_4O_3$ requires 276; found (MH$^+$) 277.

Description of D52 (Alternative Procedure)

Ethyl 3-{5-[(hydroxyamino)(imino)methyl]-1H-indazol-1-yl}propanoate (D52)

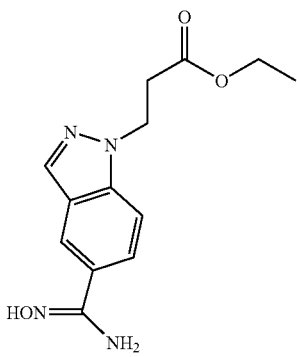

Ethyl 3-(5-cyano-1H-indazol-1-yl)propanoate D47 (3.6 g, 14.80 mmol) was dissolved in ethanol (40 ml), hydroxylamine hydrochloride (2.057 g, 29.6 mmol) and sodium bicarbonate (6.22 g, 74.0 mmol) were added. The mixture was heated at 60° C. overnight. Cooled, filtered and the filtrate was evaporated, dissolved in EtOAc, washed with water (3×20 ml), dried over MgSO$_4$ and evaporated again to give (1.75 g) of product. A further 0.290 g of white crystals were recovered from the rotary evaporator. MS (ES$^+$): $C_{13}H_{16}N_4O_3$ requires 276; found (MH$^+$) 277.

Description of D53

Ethyl 4-{5-[(hydroxyamino)(imino)methyl]-1H-indazol-1-yl}butanoate (D53)

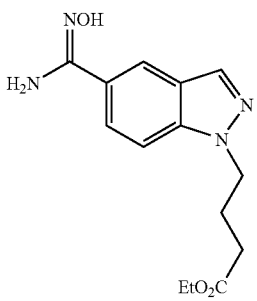

This was prepared by a similar method to that described above from D50 RD107973-039B1. MS (ES): $C_{14}H_{18}N_4O_3$ requires 290; found (MH$^+$) 291.

Description of D54

Ethyl 4-{5-[(hydroxyamino)(imino)methyl]-2H-indazol-2-yl}butanoate (D54)

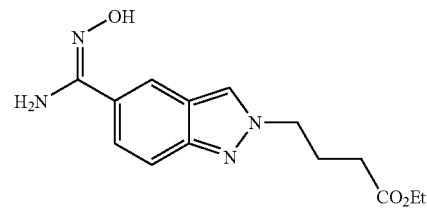

This was prepared by a similar method to that described above from ethyl 4-(5-cyano-2H-indazol-2-yl)butanoate (D51). MS (ES): $C_{14}H_{18}N_4O_3$ requires 290; found (MH$^+$) 291.

Description of D55

A mixture of ethyl 3-{4-[(hydroxyamino)(imino)methyl]-2H-indazol-2-yl}propanoate & ethyl 3-{4-[(hydroxyamino)(imino)methyl]-1H-indazol-1-yl}propanoate (D55)

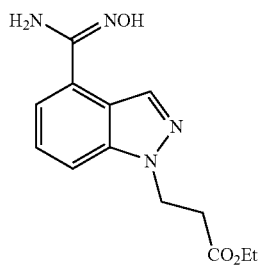

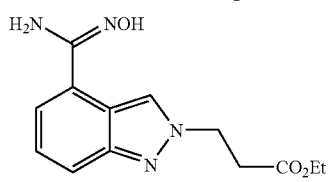

A mixture of ethyl 3-(4-cyano-2H-indazol-2-yl)propanoate & ethyl 3-(4-cyano-1H-indazol-1-yl)propanoate (D49) (1.2 g, 4.938 mmol) (sample was a ~3:1 mixture of 1 and 2-isomers), hydroxylamine hydrochloride (0.686 g, 9.87 mmol) and sodium bicarbonate (2.072 g, 24.66 mmol) in ethanol (15 ml) were heated at 50° C. for 3 hrs. The solid was filtered and the filtrate evaporated to dryness to give (1.4 g) colourless oil. LCMS and NMR confirmed ~3:1 mixture of isomers. MS (ES): $C_{13}H_{16}N_4O_3$ requires 276; found (MH$^+$) 277.

Description of D56

A mixture of ethyl 4-{4-[(hydroxyamino)(imino)methyl]-2H-indazol-2-yl}butanoate & ethyl 4-{4-[(hydroxyamino)(imino)methyl]-1H-indazol-1-yl}butanoate (D56)

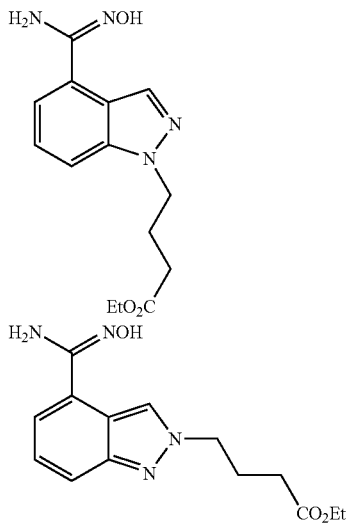

A mixture of ethyl 4-(4-cyano-2H-indazol-2-yl)butanoate & ethyl 4-(4-cyano-1H-indazol-1-yl)butanoate (D48) (0.249 g, 0.968 mmol) (sample was a ~3:2 mixture of 1 and 2-isomers), hydroxylamine hydrochloride (0.135 g, 1.936 mmol) and sodium bicarbonate (0.407 g, 4.84 mmol) in ethanol (5 ml) was stirred and heated at 80° C. for 90 minutes then diluted with ethyl acetate (30 ml)/water (50 ml) and the organic dried (magnesium sulphate) and evaporated to give the title mixture (270 mg) as a colourless gum. LC/MS showed a 3:2 mix of isomers with a couple of small impurities. MS (ES): $C_{14}H_{18}N_4O_3$ requires 290; found (MH$^+$) 291

Description of D56 (Alternative Procedure)

A mixture of ethyl 4-{4-[(hydroxyamino)(imino)methyl]-2H-indazol-2-yl}butanoate & ethyl 4-{4-[(hydroxyamino)(imino)methyl]-1H-indazol-1-yl}butanoate (D56)

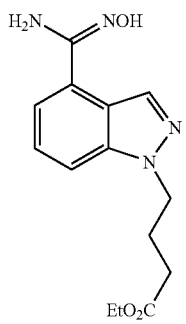

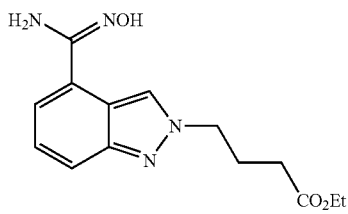

A suspension of A mixture of ethyl 4-(4-cyano-2H-indazol-2-yl)butanoate & ethyl 4-(4-cyano-1H-indazol-1-yl)butanoate (D48) (4.7 g, 9.13 mmol) (sample was a ~2:1 mixture of 1 and 2-isomers), hydroxylamine hydrochloride (2.54 g, 36.5 mmol) and sodium bicarbonate (7.67 g 91 mmol) in ethanol (50 ml) was heated at 50° C. for 3 hrs, cooled and evaporated and partitioned between EtOAc/water. The organic layer was dried (magnesium sulphate), evaporated and triturated with ether to give the title mixture (4 g) as a white solid. NMR and LCMS showed 2:1 mixture of isomers. MS (ES): $C_{14}H_{18}N_4O_3$ requires 290; found (MH+) 291.

Description of D57

Ethyl 3-(5-{5-[3-chloro-4-(ethyloxy)phenyl]-1,2,4-oxadiazol-3-yl}-1H-indazol-1-yl)propanoate (D57)

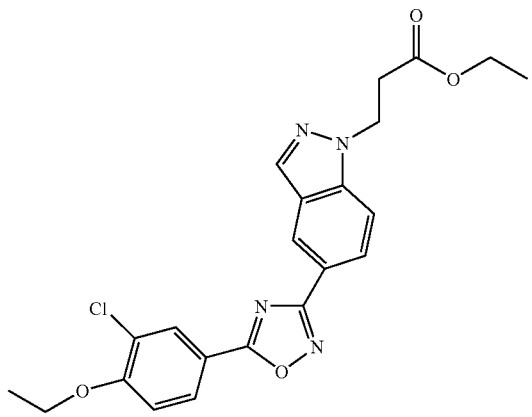

Ethyl 3-{5-[(hydroxyamino)(imino)methyl]-1H-indazol-1-yl}propanoate (D52) (265 mg, 0.96 mmol) and 3-Chloro-4-(ethyloxy)benzoic acid (D7) (192 mg, 0.96 mmol) were stirred together in DMF (5 ml) at 80° C. and EDAC (203 mg) and HOBt (142 mg) were added. When the reaction was judged to be complete (analysis by LCMS) it was cooled and the reaction mixture was partitioned between EtOAc and aq. sodium bicarbonate solution. The organic layer was separated and washed with water, dried and evaporated and triturated with ethanol to give the crude product. Purification by flash chromatography (EtOAc/hexane 1:3 to 1:1) to afforded the title compound (87 mg) as a white solid. MS (ES): $C_{22}H_{21}{}^{35}ClN_4O_4$ requires 440 found (MH$^+$) 441.

Description of D58

Ethyl 3-[5-(5-{3-cyano-4-[(1-methylethyl)oxy]phenyl}-1,2,4-oxadiazol-3-yl)-1H-indazol-1-yl]propanoate (D58)

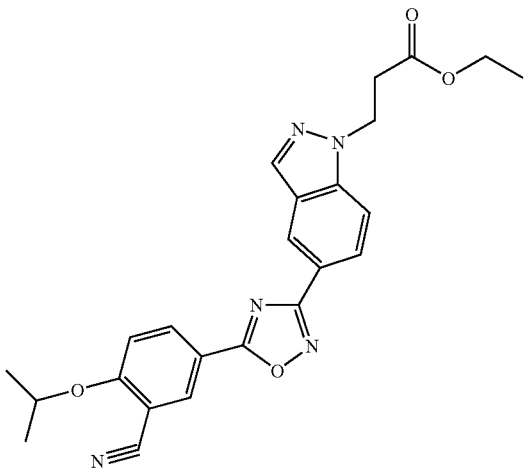

Ethyl 3-{5-[(hydroxyamino)(imino)methyl]-1H-indazol-1-yl}propanoate (D52) (265 mg, 0.96 mmol), 3-cyano-4-[(1-methylethyl)oxy]benzoic acid (can be prepared as described in WO2005/58848) (197 mg, 0.96 mmol), EDAC (203 mg) and HOBt (142 mg) were stirred in DMF (5 ml) at 80° C. for 2 hours. Stirred at room temperature over the weekend, then heated at 80° C. for a further 4 hours. The reaction mixture was cooled and then partitioned between EtOAc and sodium bicarbonate. The organic layer was separated, washed with brine, dried and evaporated to dryness in vacuo. The crude material was purified by flash chromatography to afford the title compound (214 mg) as a white solid. MS (ES): $C_{24}H_{23}N_5O_4$ requires 445; found (MH$^+$) 446.

Description of D58 (Alternative Procedure)

Ethyl 3-[5-(5-{3-cyano-4-[(1-methylethyl)oxy]phenyl}-1,2,4-oxadiazol-3-yl)-1H-indazol-1-yl]propanoate (D58)

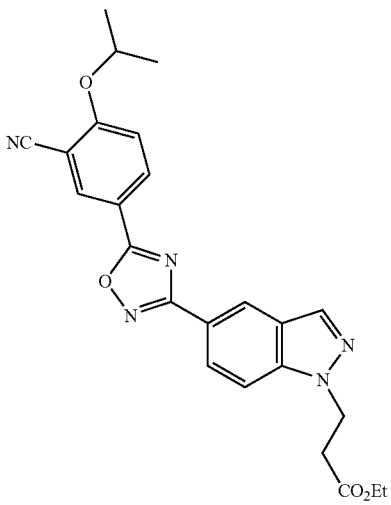

A mixture of 3-cyano-4-[(1-methylethyl)oxy]benzoic acid (can be prepared as described in WO2005/58848) (371 mg, 1.81 mmol), EDAC (547 mg, 2.85 mmol) and HOBt (437 mg, 2.85 mmol) in DMF (5 ml) was left standing at RT for 10 minutes. Added ethyl 3-{5-[(hydroxyamino)(imino)methyl]-1H-indazol-1-yl}propanoate (D52) (500 mg, 1.81 mmol) and left standing overnight at RT. Added EDAC (200 mg, 1.04 mmol) and left standing for 24 hours. The mixture was heated at 80° C. for 2 days, standing at RT each night. The mixture was heated at 80° C. for a further 4 hours. Added EtOAc (50 ml) and washed with water (60 ml), sat. NaHCO$_3$ (60 ml) and water (60 ml). The EtOAc layer was dried (MgSO$_4$) and the solvent evaporated. Triturating with ethanol gave the title compound (523 mg) as a beige solid. MS (ES): $C_{24}H_{23}N_5O_4$ requires 445; found (MH$^+$) 446.

Description of D59

Ethyl 3-(5-{5-[4-[(1-methylethyl)oxy]-3-(trifluoromethyl)phenyl]-1,2,4-oxadiazol-3-yl}-1H-indazol-1-yl)propanoate (D59)

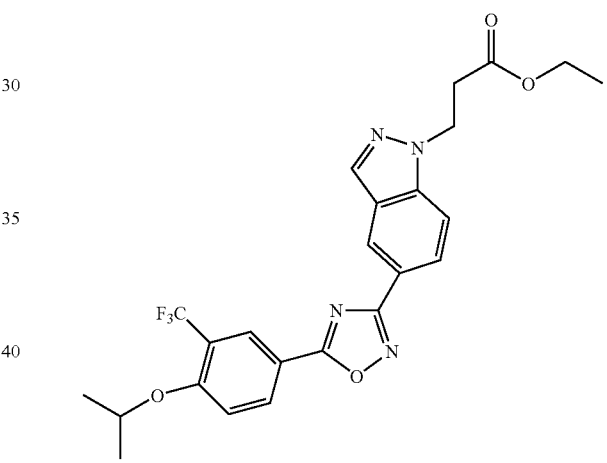

4-[(1-Methylethyl)oxy]-3-(trifluoromethyl)benzoic acid (D36) (100 mg, 0.4 mmol) was dissolved in DMF (5 ml) and then EDAC (115 mg, 0.6 mmol) and HOBt (81 mg, 0.6 mmol) were added. The mixture was stirred for 30 minutes and then Ethyl 3-{5-[(hydroxyamino)(imino)methyl]-1H-indazol-1-yl}propanoate (D52) (111 mg, 0.40 mmol) was added and the reaction was heated overnight at 80° C. Further EDAC (50 mg) was added and the reaction was heated for another 4 hours. Further EDAC (20 mg) was added and the reaction was heated overnight. The reaction mixture was added to a mixture of ethyl acetate and sodium bicarbonate, the organics were separated and the aqueous extracted with further ethyl acetate. The combined organics were washed with water and then brine, dried and evaporated to give the crude product. This material was purified by flash chromatography (SiO$_2$) to afford the title compound (82 mg). MS (ES): $C_{24}H_{23}F_3N_4O_4$ requires 488; found (MH$^+$) 489.

Description of D60

Ethyl 4-[4-(5-{3-chloro-4-[(1-methylethyl)oxy]phenyl}-1,2,4-oxadiazol-3-yl)-1H-indazol-1-yl]butanoate (D60)

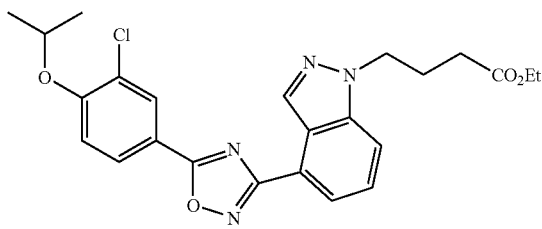

A mixture of ethyl 4-{4-[(hydroxyamino)(imino)methyl]-2H-indazol-2-yl}butanoate & ethyl 4-{4-[(hydroxyamino)(imino)methyl]-1H-indazol-1-yl}butanoate (D56) (0.27 g, 0.930 mmol) (a 3:2 mix of 1 and 2-isomers), 3-chloro-4-[(1-methylethyl)oxy]benzoic acid (D3) (0.200 g, 0.930 mmol), EDC (0.196 g, 1.023 mmol) and HOBT (0.157 g, 1.023 mmol) in N,N-dimethylformamide (5 ml) was stirred at 80° C. for 16 hrs then at 120° C. for 2 hours. The reaction was cooled, diluted with ethyl acetate (40 ml) and water (40 ml) and the organic washed with 3×15 ml of water, dried (magnesium sulphate) and evaporated. The crude material was purified by flash chromatography eluting with 3:7 ethyl acetate/hexane to give two products which were triturated with 1:1 ether/hexane to give 66 mgs of upper spot and 36 mgs of lower. The upper spot was the desired 1-substituted indazole. δH (CDCl$_3$, 400 MHz): 1.24 (3H, t), 1.46 (6H, d), 2.31 (4H, m), 4.12 (2H, q), 4.55 (2H, t), 4.73 (1H, m), 7.08 (1H, d), 7.52 (1H, dd), 7.62 (1H, d), 8.07 (1H, dd), 8.11 (1H, dd), 8.29 (1H, d), 8.70 (1H, d).

Description of D60 (Alternative Procedure)

Ethyl 4-[4-(5-{3-chloro-4-[(1-methylethyl)oxy]phenyl}-1,2,4-oxadiazol-3-yl)-1H-indazol-1-yl]butanoate (D60) N2665-84-A1

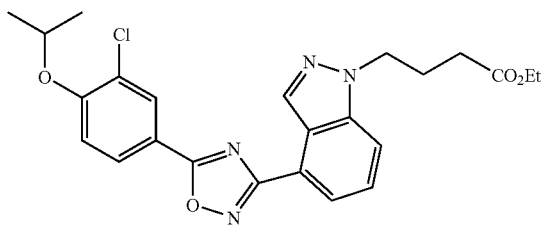

A solution of a mixture of ethyl 4-{4-[(hydroxyamino)(imino)methyl]-2H-indazol-2-yl}butanoate & ethyl 4-{4-[(hydroxyamino)(imino)methyl]-1H-indazol-1-yl}butanoat (D56) (4 g, 13.78 mmol), 3-chloro-4-[(1-methylethyl)oxy]benzoic acid (D3) (2.96 g, 13.78 mmol), EDC (2.91 g, 15.16 mmol) and HOBT (2.321 g, 15.16 mmol) in DMF (40 ml) was stirred at RT for 3 hrs to form intermediate then heated at 120° C. for 2 hrs to cyclise. The solution was cooled, diluted with EtOAc, washed with water 3× dried (magnesium sulphate) and evaporated. Purified by flash chromatography eluting with EtOAc/iso-hexane 1:3. The combined fractions were evaporated to give the title compound (1.5 g) as a white solid. MS (ES): C$_{24}$H$_{25}$$^{35}$ClN$_4$O$_4$ requires 468; found (MH$^+$) 469. δH (CDCl$_3$, 400 MHz): 1.24 (3H, t), 1.46 (6H, d), 2.31 (4H, m), 4.12 (2H, q), 4.55 (2H, t), 4.73 (1H, m), 7.08 (1H, d), 7.52 (1H, dd), 7.62 (1H, d), 8.06 (1H, dd), 8.10 (1H, dd), 8.29 (1H, d), 8.70 (1H, d).

Description of D61

Ethyl 3-[4-(5-{3-chloro-4-[(1-methylethyl)oxy]phenyl}-1,2,4-oxadiazol-3-yl)-1H-indazol-1-yl]propanoate (D61)

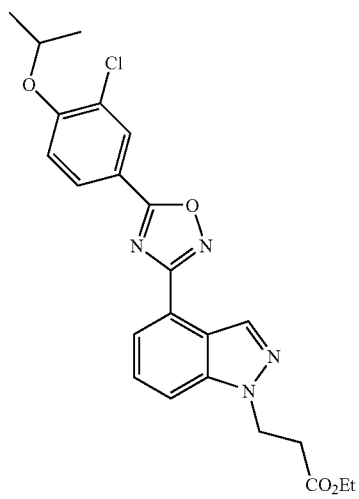

A mixture of ethyl 3-{4-[(hydroxyamino)(imino)methyl]-2H-indazol-2-yl}propanoate & ethyl 3-{4-[(hydroxyamino)(imino)methyl]-1H-indazol-1-yl}propanoate (D55) (700 mg, 1.27 mmol) (a 3:1 mix of 1 and 2-isomers), 3-chloro-4-[(1-methylethyl)oxy]benzoic acid (D3) (0.544 g, 2.53 mmol), EDC (0.534 g, 2.79 mmol) and HOBT (0.427 g, 2.79 mmol) in N,N-dimethylformamide (10 ml) was heated at 120° C. for 2 hrs, cooled, diluted with ethyl acetate (60 ml) and washed with water (3×20 ml). The organic layer was dried (MgSO$_4$), evaporated and purified by flash chromatography eluting with EtOAc/hexane 1:4 to give the title compound (380 mg) as a white solid. δH (CDCl$_3$, 400 MHz): 1.17 (3H, t), 1.46 (6H, d), 3.02 (2H, t), 4.10 (2H, q), 4.70-4.77 (3H, m), 7.08 (1H, d), 7.53 (1H, dd), 7.69 (1H, d), 8.05-8.12 (2H, m), 8.29 (1H, d), 8.71 (1H, d). MS (ES): C$_{23}$H$_{23}$$^{35}$ClN$_4$O$_4$ requires 454; found (MH$^+$) 455.

The following compounds were prepared by similar chemistry to the previous examples. In some cases the carboxylic acid, EDAC and HOBt were stirred together prior to addition of the amidoxime. In some cases the reaction mixture was stirred at room temperature prior to heating. Unless stated otherwise, the reactions were carried out at a temperature between 80 and 120° C. in DMF. In some cases further EDAC and/or HOBt were added. In the case of D91 further carboxylic acid was added. The products were purified by either flash chromatography, trituration, MDAP, reversed phase chromatography, precipitation of the product from the reaction mixture using ethanol or a combination of these methods.

| Number | Structure | Name | Precursor | MS |
|---|---|---|---|---|
| D62 | 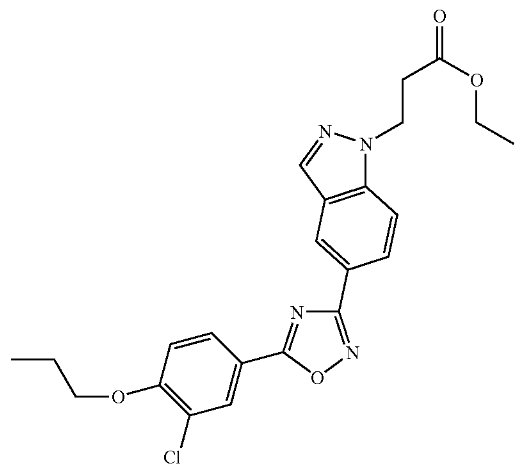 | ethyl 3-(5-{5-[3-chloro-4-(propyloxy)phenyl]-1,2,4-oxadiazol-3-yl}-1H-indazol-1-yl)propanoate | D38 & D52 | [MH+] 455 |
| D63 | 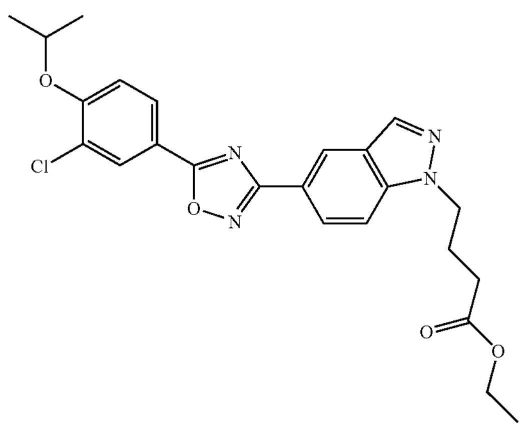 | ethyl 4-[5-(5-{3-chloro-4-[(1-methylethyl)oxy]phenyl}-1,2,4-oxadiazol-3-yl)-1H-indazol-1-yl]butanoate | D53 & D3 | [MH+] 469 |
| D64 | 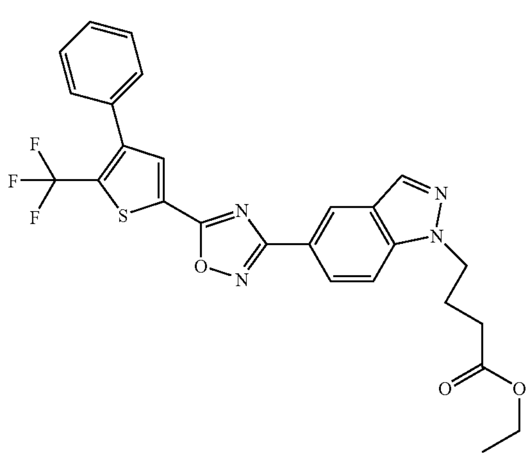 | Ethyl 4-(5-{5-[4-phenyl-5-(trifluoromethyl)-2-thienyl]-1,2,4-oxadiazol-3-yl}-1H-indazol-1-yl)butanoate | D53 | [MH+] 527 |

-continued

| Number | Structure | Name | Precursor | MS |
|---|---|---|---|---|
| D65 | 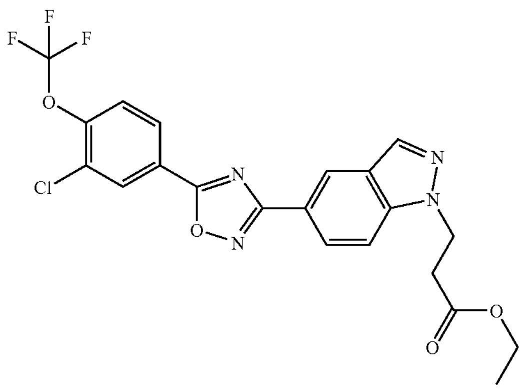 | ethyl 3-[5-(5-{3-chloro-4-[(trifluoromethyl)oxy]phenyl}-1,2,4-oxadiazol-3-yl)-1H-indazol-1-yl]propanoate | D52 | [MH+] 481 |
| D66 | 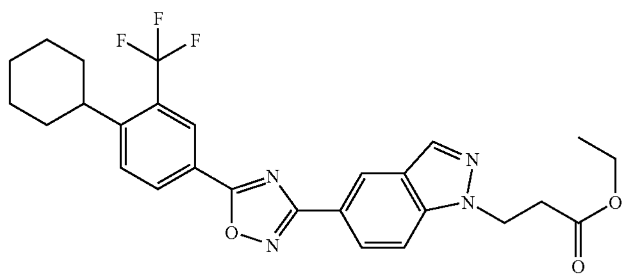 | ethyl 3-(5-{5-[4-cyclohexyl-3-(trifluoromethyl)phenyl]-1,2,4-oxadiazol-3-yl}-1H-indazol-1-yl)propanoate | D34 & D52 | [MH+] 513 |
| D67 | 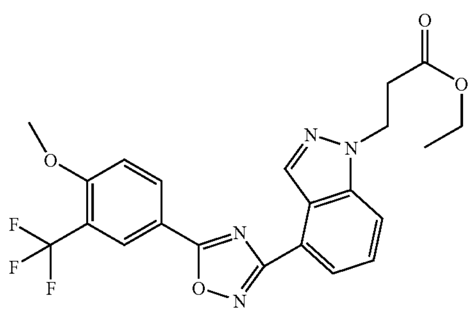 | ethyl 3-(5-{5-[4-(methyloxy)-3-(trifluoromethyl)phenyl]-1,2,4-oxadiazol-3-yl}-1H-indazol-1-yl)propanoate | D52 | [MH+] 461 |
| D68 | 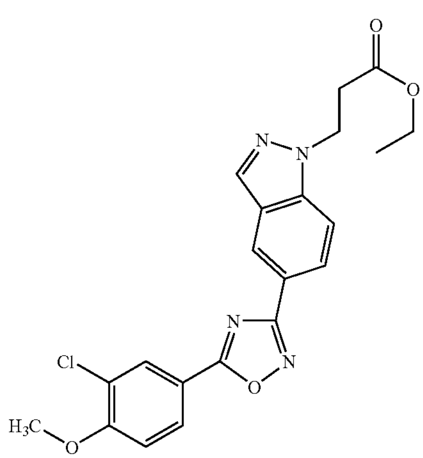 | ethyl 3-(5-{5-[3-chloro-4-(methoxlyoxy)phenyl]-1,2,4-oxadiazol-3-yl}-1H-indazol-1-yl)propanoate | D52 | [MH+] 427 |

-continued

| Number | Structure | Name | Precursor | MS |
|---|---|---|---|---|
| D69 | 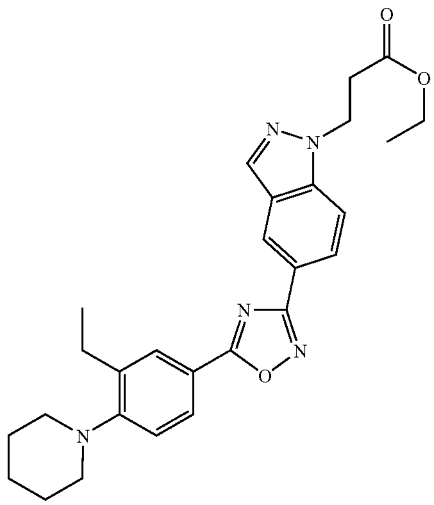 | ethyl 3-(5-{5-[3-ethyl-4-(1-piperidinyl)phenyl]-1,2,4-oxadiazol-3-yl}-1H-indazol-1-yl)propanoate | D52, D9 | [MH+] 474 |
| D70 | 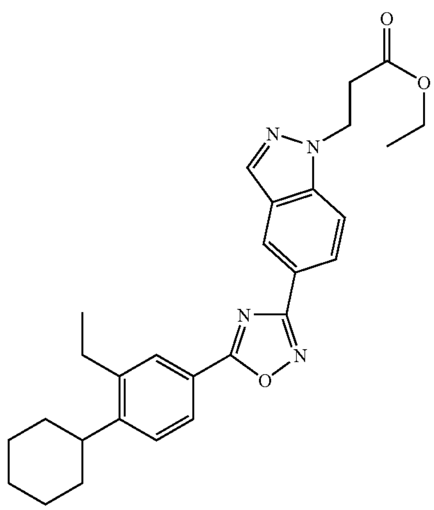 | ethyl 3-{5-[5-(4-cyclohexyl-3-ethylphenyl)-1,2,4-oxadiazol-3-yl]-1H-indazol-1-yl}propanoate | D13, D52 | [MH+] 473 |
| D71 | 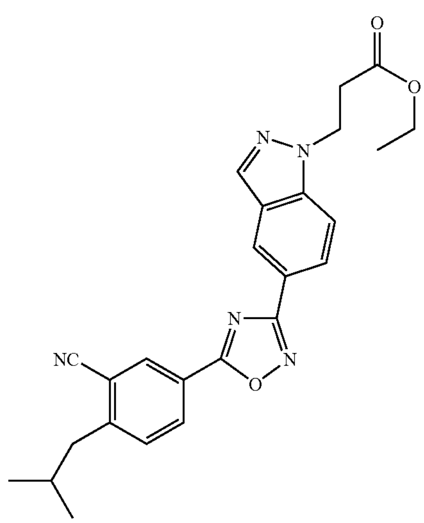 | ethyl 3-(5-{5-[3-cyano-4-(2-methylpropyl)phenyl]-1,2,4-oxadiazol-3-yl}-1H-indazol-1-yl)propanoate | D52 & D25 | [MH+] 444 |

| Number | Structure | Name | Precursor | MS |
|---|---|---|---|---|
| D72 | 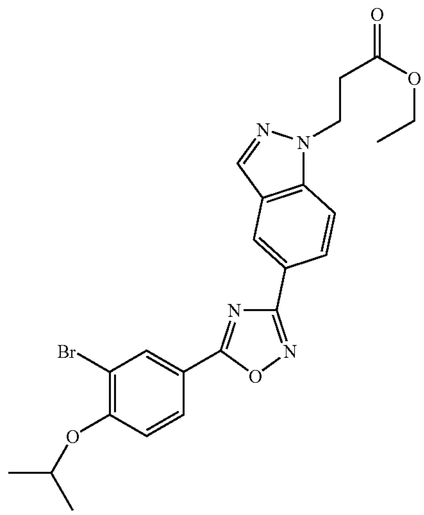 | ethyl 3-[5-(5-{3-bromo-4-[(1-methylethyl)oxy]phenyl}-1,2,4-oxadiazol-3-yl)-1H-indazol-1-yl]propanoate | D52 & D15 | [MH+] 499, 501 |
| D73 | 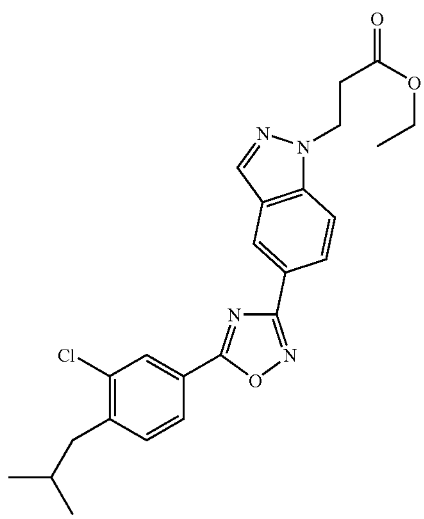 | ethyl 3-(5-{5-[3-chloro-4-(2-methylpropyl)phenyl]-1,2,4-oxadiazol-3-yl}-1H-indazol-1-yl)propanoate | D52 & D18 | [MH+] 453, 455 |
| D74 | 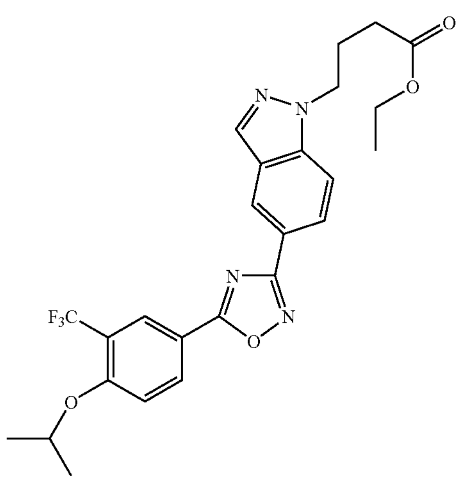 | ethyl 4-(5-{5-[4-[(1-methylethyl)oxy]-3-(trifluoromethyl)phenyl]-1,2,4-oxadiazol-3-yl}-1H-indazol-1-yl)butanoate | D53 & D36 | [MH+] 503 |

| Number | Structure | Name | Precursor | MS |
|---|---|---|---|---|
| D75 | 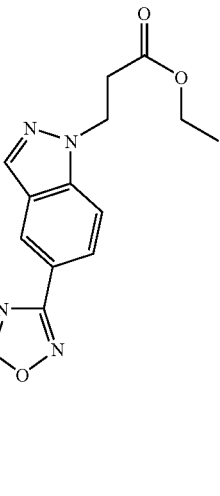 | ethyl 3-{5-[5-(2-cyano-4-biphenylyl)-1,2,4-oxadiazol-3-yl]-1H-indazol-1-yl}propanoate | D52 & D21 | [MH+] 464 |
| D76 | 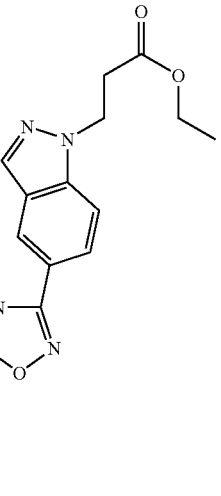 | ethyl 3-(5-{5-[3-chloro-4-(1-pyrrolidinyl)phenyl]-1,2,4-oxadiazol-3-yl}-1H-indazol-1-yl)propanoate | D52 & D40 | [MH+] 466 |
| D77 | 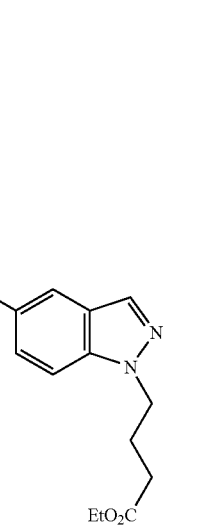 | ethyl 4-[5-(5-{5-chloro-6-[(1-methylethyl)oxy]-3-pyridinyl}-1,2,4-oxadiazol-3-yl)-1H-indazol-1-yl]butanoate | D31 & D53 | 470 (MH+) for $^{35}$Cl |

| Number | Structure | Name | Precursor | MS |
|---|---|---|---|---|
| D78 | 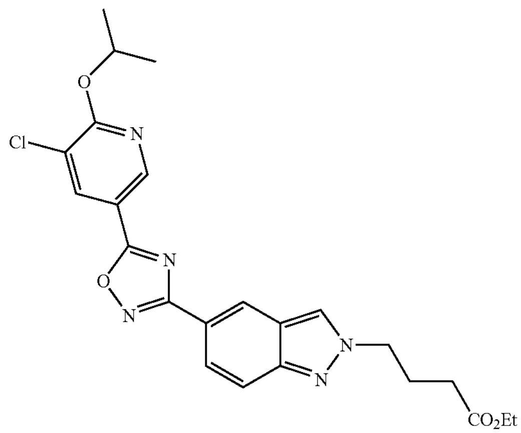 | ethyl 4-[5-(5-{5-chloro-6-[(1-methylethyl)oxy]-3-pyridinyl}-1,2,4-oxadiazol-3-yl)-2H-indazol-2-yl]butanoate | D54 and D31 | 470 (MH$^+$) for $^{35}$Cl |
| D79 | 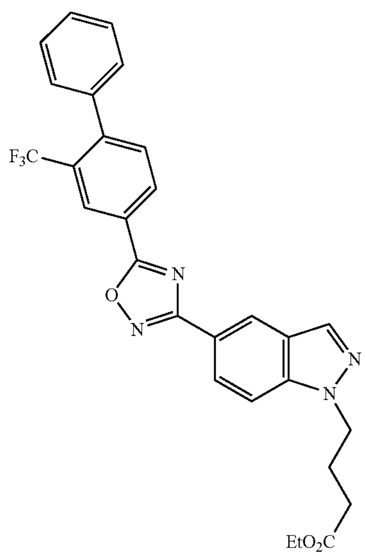 | ethyl 4-(5-{5-[2-(trifluoromethyl)-4-biphenylyl]-1,2,4-oxadiazol-3-yl}-1H-indazol-1-yl)butanoate | D53 & D23 | [MH$^+$] 521 |
| D80 | 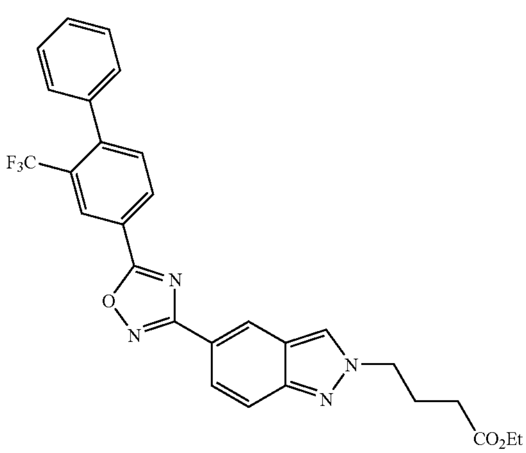 | ethyl 4-(5-{5-[2-(trifluoromethyl)-4-biphenylyl]-1,2,4-oxadiazol-3-yl}-2H-indazol-2-yl)butanoate | D54 and D23 | [MH$^+$] 521 |

-continued

| Number | Structure | Name | Precursor | MS |
|---|---|---|---|---|
| D81 | 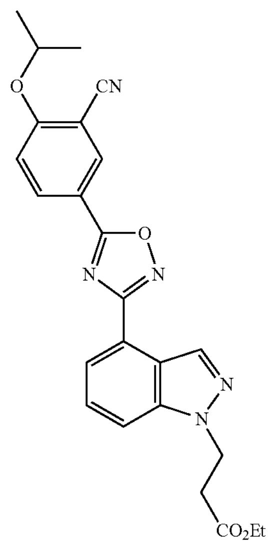 | ethyl 3-[4-(5-{3-cyano-4-[(1-methylethyl)oxy]phenyl}-1,2,4-oxadiazol-3-yl)-1H-indazol-1-yl]propanoate | D55 | [MH+] 446 |
| D82 | 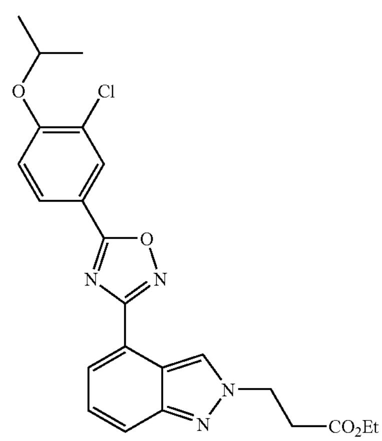 | ethyl 3-[4-(5-{3-chloro-4-[(1-methylethyl)oxy]phenyl}-1,2,4-oxadiazol-3-yl)-2H-indazol-2-yl]propanoate | D55 & D3 | [MH+] 455, 457 |
| D83 | 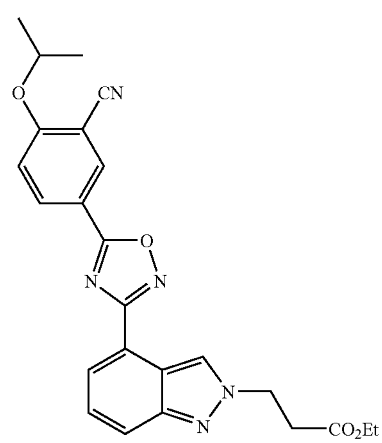 | ethyl 3-[4-(5-{3-cyano-4-[(1-methylethyl)oxy]phenyl}-1,2,4-oxadiazol-3-yl)-2H-indazol-2-yl]propanoate | D55 | [MH+] 446 |

| Number | Structure | Name | Precursor | MS |
|---|---|---|---|---|
| D84 | 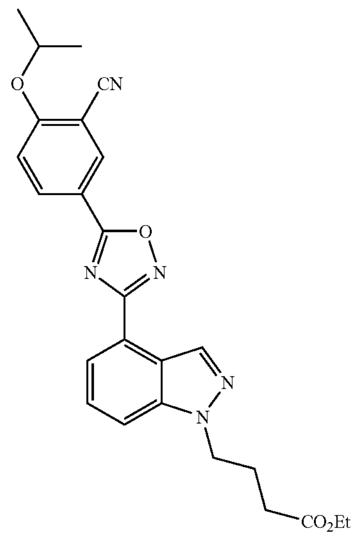 | ethyl 4-[4-(5-{3-cyano-4-[(1-methylethyl)oxy]phenyl}-1,2,4-oxadiazol-3-yl)-1H-indazol-1-yl]butanoate | D56 | [MH+] 460 |
| D85 | 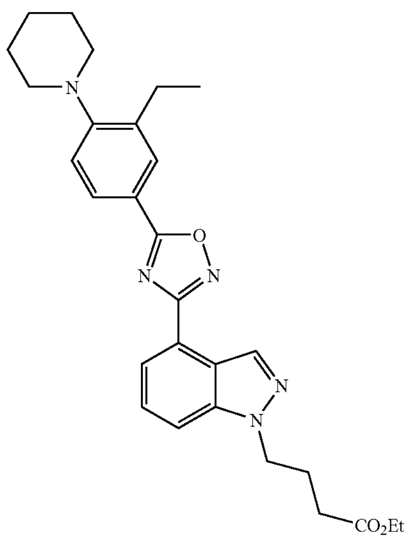 | ethyl 4-(4-{5-[3-ethyl 4-(1-piperidinyl)phenyl]-1,2,4-oxadiazol-3-yl}-1H-indazol-1-yl)butanoate | D56 & D9 | [MH+] 488 |
| D86 | 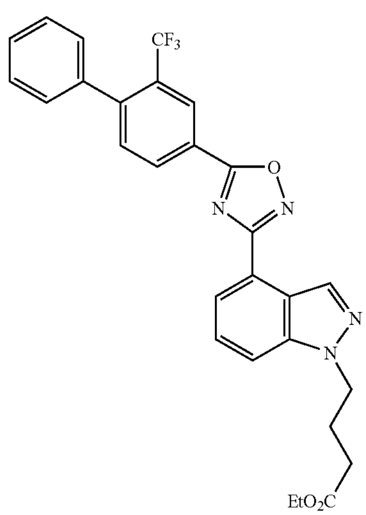 | ethyl 4-(4-{5-[2-(trifluoromethyl)-4-biphenylyl]-1,2,4-oxadiazol-3-yl}-1H-indazol-1-yl)butanoate | D56 & D23 | [MH+] 521. |

| Number | Structure | Name | Precursor | MS |
|---|---|---|---|---|
| D87 | 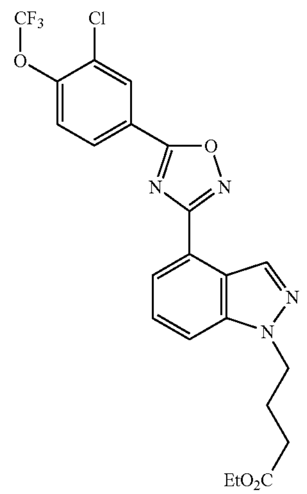 | ethyl 4-[4-(5-{3-chloro-4-[(trifluoromethyl)oxy]phenyl}-1,2,4-oxadiazol-3-yl)-1H-indazol-1-yl]butanoate | D56 | [MH+] 495 |
| D88 | 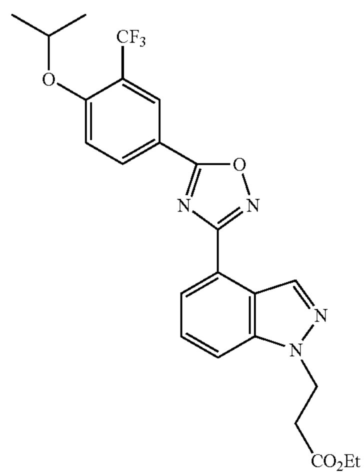 | ethyl 3-(4-{5-[4-[(1-methylethyl)oxy]-3-(trifluoromethyl)phenyl]-1,2,4-oxadiazol-3-yl}-1H-indazol-1-yl)propanoate | D97 & D36 | [MH+] 489 |
| D89 | 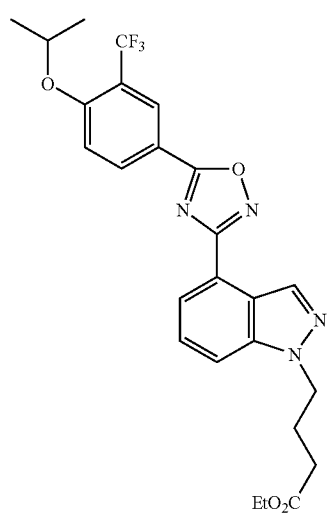 | ethyl 4-(4-{5-[4-[(1-methylethyl)oxy]-3-(trifluoromethyl)phenyl]-1,2,4-oxadiazol-3-yl}-1H-indazol-1-yl)butanoate | D56 & D36 | [MH+] 503 |

-continued
| Number | Structure | Name | Precursor | MS |
|---|---|---|---|---|
| D90 | 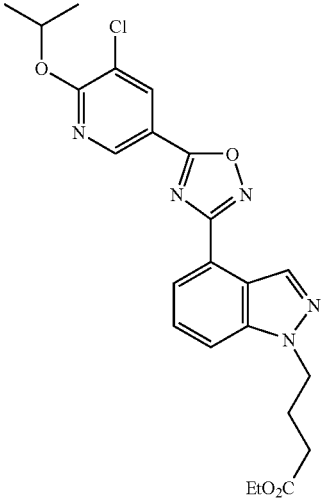 | ethyl 4-[4-(5-{5-chloro-6-[(1-methylethyl)oxy]-3-pyridinyl}-1,2,4-oxadiazol-3-yl)-1H-indazol-1-yl]butanoate | D56 & D31 | [MH+] 470, 472 |
| D91 | 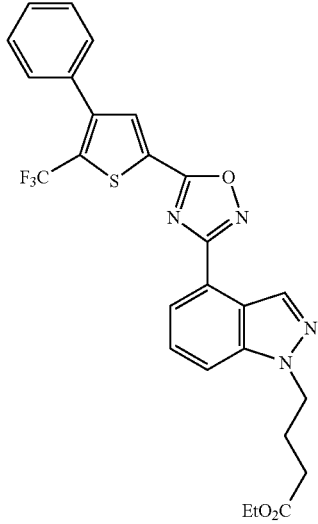 | ethyl 4-(4-{5-[4-phenyl-5-(trifluoromethyl)-2-thienyl]-1,2,4-oxadiazol-3-yl}-1H-indazol-1-yl)butanoate | D56 | [MH+] 527 |
| D92 | 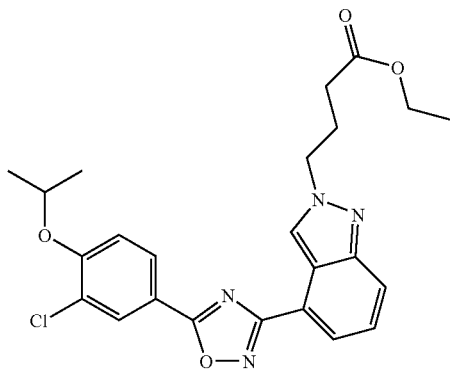 | ethyl 4-[4-(5-{3-chloro-4-[(1-methylethyl)oxy]phenyl}-1,2,4-oxadiazol-3-yl)-2H-indazol-2-yl]butanoate | D56 & D3 | [MH+] 469 |

-continued

| Number | Structure | Name | Precursor | MS |
|---|---|---|---|---|
| D93 | 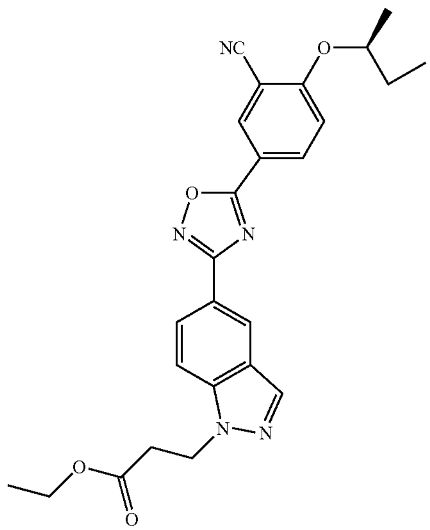 | ethyl 3-{5-[5-(3-cyano-4-{[(1S)-1-methylpropyl]oxy}phenyl)-1,2,4-oxadiazol-3-yl]-1H-indazol-1-yl}propanoate | D52 & D27 | [MH+] 460 |
| D94 | 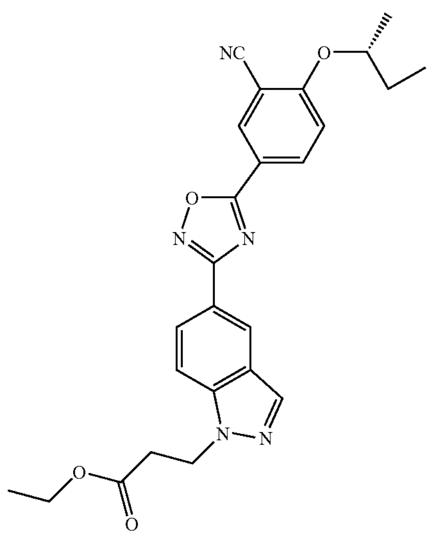 | ethyl 3-{5-[5-(3-cyano-4-{[(1R)-1-methylpropyl]oxy}phenyl)-1,2,4-oxadiazol-3-yl]-1H-indazol-1-yl}propanoate | D52 & D29 | [MH+] 460 |
| D95 | 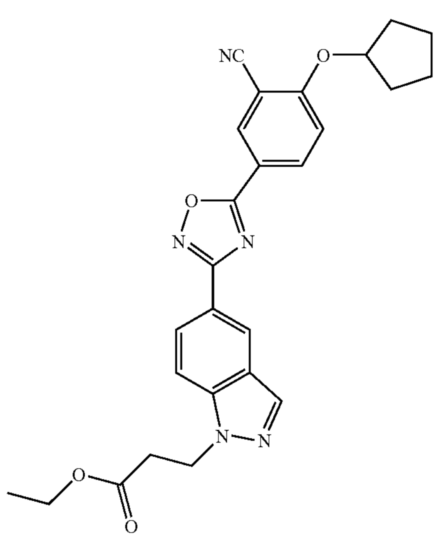 | ethyl 3-(5-{5-[3-cyano-4-(cyclopentyloxy)phenyl]-1,2,4-oxadiazol-3-yl}-1H-indazol-1-yl)propanoate | D52 & D42 | [MH+] 472 |

Description of D96

Ethyl 3-(4-cyano-1H-indazol-1-yl)propanoate (D96)

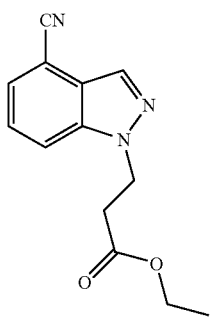

1H-indazole-4-carbonitrile (0.716 g, 5 mmol), ethyl 3-bromopropanoate (1.276 ml, 10.00 mmol) and caesium carbonate (4.90 g, 15.00 mmol) were added to N,N-dimethylformamide (DMF) (20 ml) and the mixture was was heated to 90° C. for 80 minutes. The mixture was cooled before being extracted in a mixture of ethyl acetate and water. The organic fraction was washed with 3×30 ml portions of water, dried (MgSO$_4$), filtered and evaporated. The crude product mixture was added to a Biotage column and was eluted with ethyl acetate/petrol 1:3 to give 0.95 g of the title compound. δH (CDCl$_3$, 400 MHz) 1.17 (3H, t), 3.01 (2H, t), 4.08 (2H, q), 4.71 (2H, t), 7.46 (1H, dd), 7.54 (1H, dd), 7.81 (1H, d), 8.21 (1H, d).

Description of D97

Ethyl 3-{4-[(hydroxyamino)(imino)methyl]-1H-indazol-1-yl}propanoate (D97)

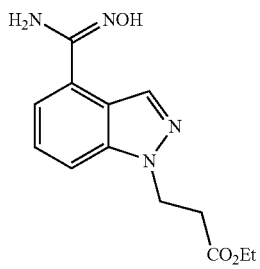

Ethyl 3-(4-cyano-1H-indazol-1-yl)propanoate (D96) (0.95 g, 3.91 mmol), hydroxylamine hydrochloride (1.086 g, 15.62 mmol), and sodium bicarbonate (3.28 g, 39.1 mmol), were heated in ethanol (20 ml) at 50° C. for 3 hours. The mixture was filtered and evaporated to give the title compound (760 mg) as a white powder. MS (ES): C$_{13}$H$_{16}$N$_4$O$_3$ requires 276; found (MH$^+$) 277.

Description of D98

Ethyl 3-bromo-2,2-dimethylpropanoate (D98)

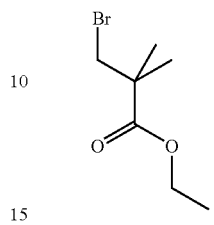

3-Bromo-2,2-dimethylpropanoic acid (commercially available from Fluka) (1 g, 5.52 mmol) was dissolved in thionyl chloride (5 ml, 68.5 mmol) and the resulting mixture was refluxed for 2 h then cooled to room temperature and concentrated in vacuo. The residue was dissolved in ethanol (10 ml) and stirred at room temperature for 30 min. Most of the solvent was removed in vacuo, the residue was dissolved in EtOAc. and was washed twice with a 1M aqueous NaOH solution, brine, dried and concentrated to give the title compound (0.939 g, 81%) as a pale yellow oil which was used in the next step without further purification.

Description of D99

Ethyl 4-bromo-2,2-dimethylbutanoate (D99)

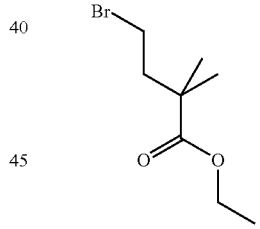

Hydrogen bromide was bubbled through 3,3-dimethyldihydro-2(3H)-furanone (1 g, 8.76 mmol) at room temperature for ca. 5 h and the resulting mixture was left at room temperature overnight. Nitrogen was then bubbled through the mixture. The crude acid was dissolved in DCM (10 ml) and treated with oxalyl chloride (2.3 ml, 26.3 mmol) and DMF (1 drop) and the resulting mixture was stirred at room temperature over the weekend then concentrated in vacuo. The residue was treated with ethanol (10 ml) and the resulting mixture stirred at room temperature for 1 hour then poured into water. The aqueous phase was extracted twice with diethyl ether and the ethereal solution was washed with brine, dried and concentrated in vacuo to give the title compound (949 mg, 49%) as a very pale yellow oil which was used in the next step without further purification.

Description of D100 and D101

Ethyl 3-[5-(5-{3-chloro-4-[(1-methylethyl)oxy]phenyl}-1,2,4-oxadiazol-3-yl)-1H-indazol-1-yl]-2,2-dimethylpropanoate (D100), N6128-6-A4 and ethyl 3-[5-(5-{3-chloro-4-[(1-methylethyl)oxy]phenyl}-1,2,4-oxadiazol-3-yl)-2H-indazol-2-yl]-2,2-dimethylpropanoate (D101)

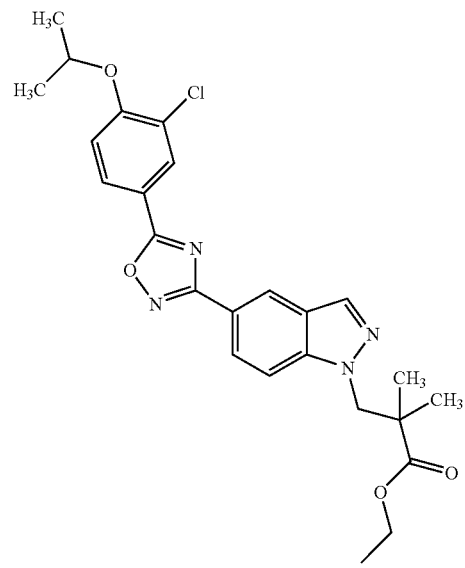

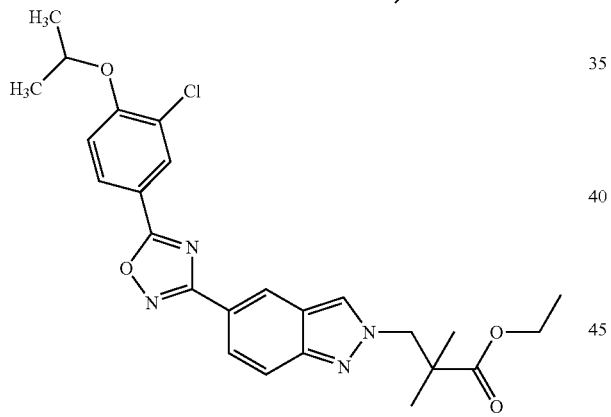

5-(5-{3-chloro-4-[(1-methylethyl)oxy]phenyl}-1,2,4-oxadiazol-3-yl)-1H-indazole (D4) (122 mg, 0.344 mmol) in DMF (2 ml) was treated with ethyl 3-bromo-2,2-dimethylpropanoate (D98) (79 mg, 0.378 mmol) and Cs$_2$CO$_3$ (134 mg, 0.413 mmol) and the resulting mixture was stirred at 80° C. overnight. More ethyl 3-bromo-2,2-dimethylpropanoate (D98) (29 mg, 0.4 mmol) and Cs$_2$CO$_3$ (56 mg, 0.5 mmol) were added and the resulting mixture stirred at 80° C. for 6 h then cooled to room temperature and concentrated in vacuo. The residue was dissolved in EtOAc and the organic phase was washed with water then brine, dried and concentrated in vacuo. Purification of the residue by flash chromatography on silica gel [gradient ethyl acetate/cyclohexane] gave ethyl 3-[5-(5-{3-chloro-4-[(1-methylethyl)oxy]phenyl}-1,2,4-oxadiazol-3-yl)-1H-indazol-1-yl]-2,2-dimethylpropanoate (D100) (92 mg, 55%) and ethyl 3-[5-(5-{3-chloro-4-[(1-methylethyl)oxy]phenyl}-1,2,4-oxadiazol-3-yl)-2H-indazol-2-yl]-2,2-dimethylpropanoate (D101) (49 mg, 30%). MS (ES) C$_{25}$H$_{27}$ClN$_4$O$_4$ requires 482, found 483 [M+H]$^+$

Description of D102

Ethyl 3-(4-cyano-1H-indazol-1-yl)-2,2-dimethylpropanoate (D102)

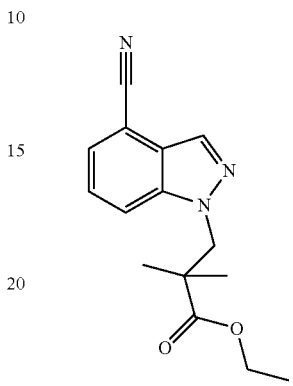

1H-Indazole-4-carbonitrile (commercially available from Insight Chemical Solutions Ltd.) (500 mg, 3.49 mmol), ethyl 3-bromo-2,2-dimethylpropanoate (D98) (803 mg, 3.84 mmol) and Cs$_2$CO$_3$ (1.36 g, 4.19 mmol) in dry DMF (3 ml) was heated to 80° C. overnight and then for a further 7 hours. The reaction mixture was then partitioned between EtOAc and H$_2$O. The two layers were separated and the organic phase was washed with more H$_2$O, brine, dried and concentrated a yellow oil. Purification of the residue by flash chromatography on silica gel [gradient ethyl acetate/cyclohexane] gave the title compound (356 mg, 37%) as a crystalline material. MS (ES) C$_{15}$H$_{17}$N$_3$O$_2$ requires 271, found 272 [M+H]$^+$ Description of D102 (Alternative Procedure)

Ethyl 3-(4-cyano-1H-indazol-1-yl)-2,2-dimethylpropanoate (D102)

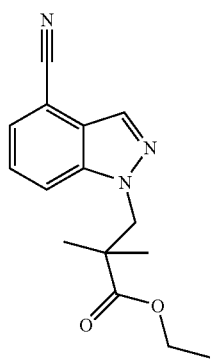

1H-indazole-4-carbonitrile (commercially available from Insight Chemical Solutions Ltd., 298 mg, 1.957 mmol) in dry N,N-Dimethylformamide (DMF) (1 ml), under nitrogen was treated with NaH (94 mg, 2.348 mmol). A solution of ethyl 3-bromo-2,2-dimethylpropanoate (D98) (450 mg, 2.153 mmol), in DMF (2 ml), was then added to the dark brown mixture. The reaction mixture was heated to 80° C. overnight then concentrated in vacuo. The residue was dissolved in EtOAc and the organic phase was washed with water then brine, dried and concentrated to give a brown gum. Purification of the residue by flash chromatography on silica gel [gradient ethyl acetate/cyclohexane] gave the title compound (217 mg, 86%) as a yellow oil. MS (ES) $C_{15}H_{15}N_3O_2$ requires 271, found 272 $[M+H]^+$ Description of D103

Ethyl 3-{4-[(hydroxyamino)(imino)methyl]-1H-indazol-1-yl}-2,2-dimethylpropanoate (D103)

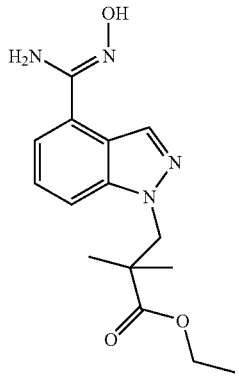

Ethyl 3-(4-cyano-1H-indazol-1-yl)-2,2-dimethylpropanoate (D102) (348 mg, 1.28 mmol), hydroxylamine hydrochloride (1.087 g, 10.26 mmol), NaHCO₃ (1.078 g, 12.83 mmol) in MeOH (20 ml) was heated at 65° C. for 24 h then at room temperature over the weekend. The mixture was filtered, concentrated, treated with water and vigorously stirred for 10 mins, filtered and dried to give a colourless solid, dried overnight in vacuo at 45° C. to give the title compound (373 mg, 90%). MS (ES) $C_{15}H_{20}N_4O_3$ requires 304, found 305 $[M+H]^+$ Description of D104

Ethyl 3-[4-(5-{3-chloro-4-[(1-methylethyl)oxy]phenyl}-1,2,4-oxadiazol-3-yl)-1H-indazol-1-yl]-2,2-dimethylpropanoate (D104)

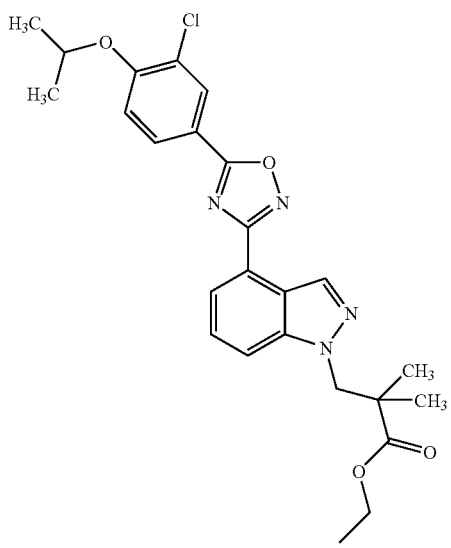

A mixture of 3-chloro-4-[(1-methylethyl)oxy]benzoic acid (D3) (245 mg, 1.143 mmol), ethyl 3-{4-[(hydroxyamino)(imino)methyl]-1H-indazol-1-yl}-2,2-dimethylpropanoate (D103) (348 mg, 1.143 mmol), in DMF (5 ml) at room temperature was treated with N-ethyl-N-(1-methylethyl)-2-propanamine (0.240 ml, 1.372 mmol) followed by HATU (522 mg, 1.372 mmol). The resulting mixture was stirred at room temperature for 1 hour and at 80° C. overnight and then for a further 4 hours, then cooled to room temperature and concentrated in vacuo. The residue was dissolved in EtOAc and the organic phase was washed twice with H₂O then brine, dried and concentrated in vacuo. Purification of the residue by flash chromatography on silica gel [gradient ethyl acetate/cyclohexane] gave the title compound (233 mg, 39%) as a cream solid. MS (ES) $C_{25}H_{27}ClN_4O_4$ requires 482, found 483 $[M+H]^+$ Description of D105

Ethyl 3-[4-(5-{5-chloro-6-[(1-methylethyl)oxy]-3-pyridinyl}-1,2,4-oxadiazol-3-yl)-1H-indazol-1-yl]-2,2-dimethylpropanoate (D105)

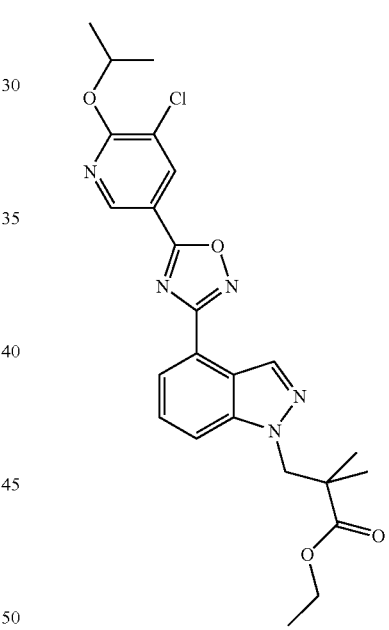

5-chloro-6-[(1-methylethyl)oxy]-3-pyridinecarboxylic acid (D31) (70.9 mg, 0.329 mmol), triethylamine (0.092 ml, 0.657 mmol), HOBT (60.4 mg, 0.394 mmol) then EDC (76 mg, 0.394 mmol) followed by ethyl 3-{4-[(hydroxyamino)(imino)methyl]-1H-indazol-1-yl}-2,2-dimethylpropanoate (D103) (100 mg, 0.329 mmol) were dissolved in N,N-Dimethylformamide (DMF) (5 ml). The resulting mixture was stirred at 50° C. overnight then cooled to room temperature and diluted in EtOAc. The organic phase was washed with H₂O, dried and concentrated in vacuo. Purification of the residue by flash chromatography on silica gel [15-40% EtOAc/cyclohexane] gave the title compound (30 mg, 17%) as a light yellow solid. MS (ES) $C_{24}H_{26}ClN_5O_4$ requires 483, found 484 $[M+H]^+$

Description of D106

3-Cyano-4-[(1-methylethyl)oxy]benzoyl chloride (D106)

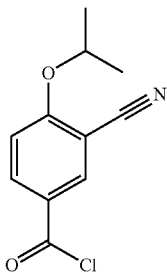

Oxalyl chloride (0.224 ml, 2.56 mmol) was added to a stirred solution of 3-cyano-4-[(1-methylethyl)oxy]benzoic acid (which can be prepared as described in WO2005/58848, 500 mg, 2.437 mmol) in DCM (10 ml), followed by DMF (20 µl) and the resulting mixture was stirred at room temperature for 2 h. The solvent was evaporated to give the title compound (545 mg, 100%) as an olive green solid which was used in the next step without further purification.

Description of D107

Ethyl 3-[5-(5-{3-cyano-4-[(1-methylethyl)oxy]phenyl}-1,2,4-oxadiazol-3-yl)-1H-indazol-1-yl]-2,2-dimethylpropanoate (D107)

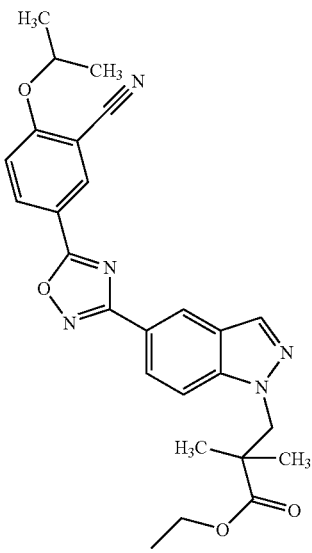

To a solution of 5-[3-(1H-indazol-5-yl)-1,2,4-oxadiazol-5-yl]-2-[(1-methylethyl)oxy]benzonitrile (D43) (85 mg, 0.246 mmol) in N,N-Dimethylformamide (DMF) (5 ml) was added ethyl 3-bromo-2,2-dimethylpropanoate (D98) (103 mg, 0.492 mmol) and $Cs_2CO_3$ (120 mg, 0.369 mmol). The resulting mixture was stirred at 80° C. for 48 h then cooled to room temperature and diluted with EtOAc. The organic phase was washed with water, dried over $MgSO_4$ and concentrated in vacuo. Purification of the residue by flash chromatography on silica gel [30-50% EtOAc/cyclohexene] gave the title compound (20 mg, 16%) as a yellow solid. MS (ES) $C_{26}H_{27}N_5O_4$ requires 473, found 474 $[M+H]^+$

Description of D108

Ethyl 4-[5-(5-{3-cyano-4-[(1-methylethyl)oxy]phenyl}-1,2,4-oxadiazol-3-yl)-1H-indazol-1-yl]-2,2-dimethylbutanoate (D108)

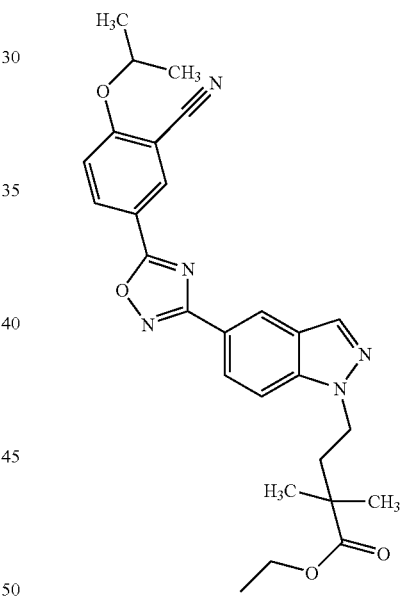

The title compound was obtained from 5-[3-(1H-indazol-5-yl)-1,2,4-oxadiazol-5-yl]-2-[(1-methylethyl)oxy]benzonitrile (D43) in 31% yield (50 mg) using a procedure analogous to the synthesis of ethyl 3-[5-(5-{3-cyano-4-[(1-methylethyl)oxy]phenyl}-1,2,4-oxadiazol-3-yl)-1H-indazol-1-yl]-2,2-dimethylpropanoate (D107), using ethyl 4-bromo-2,2-dimethylbutanoate (D99) as alkylating reagent instead of ethyl 3-bromo-2,2-dimethylpropanoate (D98). MS (ES) $C_{25}H_{25}N_5O_4$ requires 459, found 460 $[M+H]^+$

Description of D109

Ethyl 3-[4-(5-{3-cyano-4-[(1-methylethyl)oxy]phenyl}-1,2,4-oxadiazol-3-yl)-1H-indazol-1-yl]-2,2-dimethylpropanoate (D109)

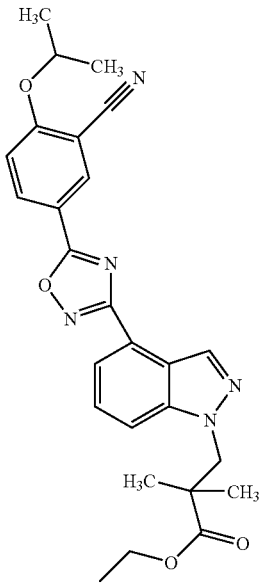

3-Cyano-4-[(1-methylethyl)oxy]benzoyl chloride (D106) (0.398 mmol) in acetonitrile (3.00 ml) at room temperature was treated with ethyl 3-{4-[(hydroxyamino)(imino)methyl]-1H-indazol-1-yl}-2,2-dimethylpropanoate (D103) (101 mg, 0.332 mmol) followed by triethylamine (0.069 ml, 0.498 mmol). The resulting yellow solution was stirred at room temperature for 1 hr, refluxed overnight, for a further 24 hours and again overnight then cooled to room temperature and concentrated in vacuo. Purification of the residue by flash chromatography on silica gel [gradient ethyl acetate/cyclohexane] gave the title compound (107 mg, 68%) as a colourless solid. MS (ES) $C_{26}H_{27}N_5O_4$ requires 473, found 474 [M+H]$^+$

Description of D110

5-(5-{5-Chloro-6-[(1-methylethyl)oxy]-3-pyridinyl}-1,2,4-oxadiazol-3-yl)-1H-indazole (D110), N6043-42

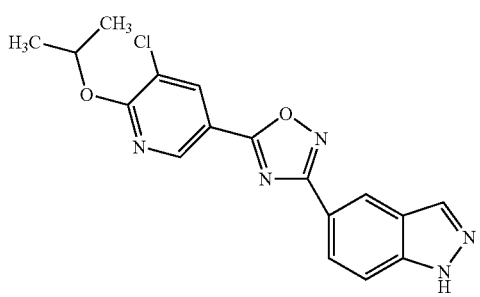

A mixture of 5-chloro-6-[(1-methylethyl)oxy]-3-pyridinecarboxylic acid (D31) (350 mg, 1.623 mmol), triethylamine (328 mg, 452 µl, 3.25 mmol), hydroxybenzotriazole hydrate (298 mg, 1.95 mmol), EDC (373 mg, 1.95 mmol) and N-hydroxy-1H-indazole-5-carboximidamide (D2) (430 mg, 2.43 mmol) in DMF (5 ml) was stirred at 50° C. for 4 days. The reaction mixture was cooled to room temperature and diluted with EtOAc (25 ml). The organic layer was washed with a saturated NaHCO₃ aqueous solution, water then brine. The organic phase was dried and concentrated in vacuo to give the title compound (334 mg, 58%) as a light red solid which was used in next step without further purification. MS (ES) $C_{17}H_{14}ClN_5O_2$ requires 355, found 356 [M+H]$^+$

Description of D111

Ethyl 3-[5-(5-{5-chloro-6-[(1-methylethyl)oxy]-3-pyridinyl}-1,2,4-oxadiazol-3-yl)-1H-indazol-1-yl]-2,2-dimethylpropanoate (D111)

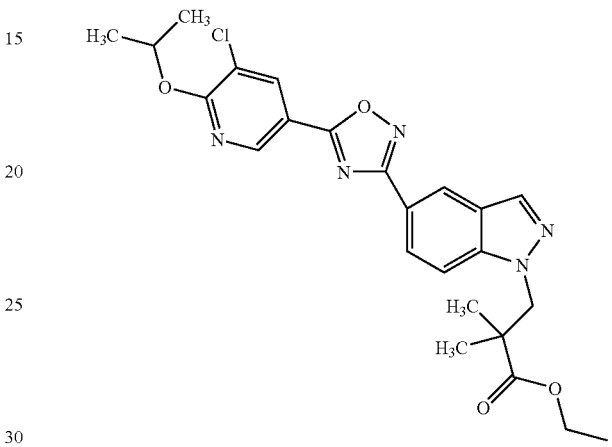

A mixture of 5-(5-{5-chloro-6-[(1-methylethyl)oxy]-3-pyridinyl}-1,2,4-oxadiazol-3-yl)-1H-indazole (D110) (335 mg, 0.94 mmol), ethyl 3-bromo-2,2-dimethylpropanoate (D98) (197 mg, 0.94 mmol) and K₂CO₃ (130 mg, 0.94 mmol) in DMF (5 ml) was stirred at 80° C. for 48 hours. The reaction mixture was then cooled to room temperature and partitioned between EtOAc and water (30 ml). The organic phase was separated, dried over MgSO₄ and concentrated in vacuo. Purification of the residue by flash chromatography on silica gel [20% ethyl acetate/cyclohexane] gave the title compound (100 mg, 22%) as a colourless solid. MS (ES) $C_{24}H_{26}ClN_5O_4$ requires 483, found 484 [M+H]$^+$

Description of D112

Ethyl 4-(4-bromo-1H-indazol-1-yl)-2,2-dimethylbutanoate (D112)

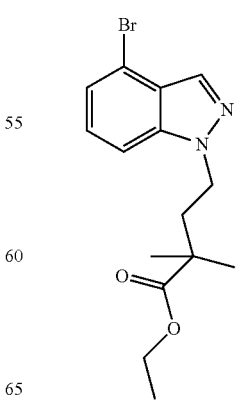

To a solution of 4-bromo-1H-indazole (commercially available from Insight Chemical Solutions Ltd., 826 mg, 4.19 mmol) in DMF (10 ml) at room temperature were added $Cs_2CO_3$ (1.37 g, 4.19 mmol) and ethyl 4-bromo-2,2-dimethylbutanoate (D99) (1.40 g, 6.29 mmol) and the resulting mixture was stirred at 80° C. for 24 h then cooled to room temperature and diluted with AcOEt. The organic phase was washed with water, dried over $MgSO_4$ and concentrated in vacuo. Purification of the residue by flash chromatography on silica gel [15-25% EtOAc/cyclohexane] gave the title compound (600 mg, 40%) as orange oil. MS (ES) $C_{15}H_{19}{}^{81}BrN_2O_2$ requires 340, found 341 $[M+H]^+$ Description of D113

Ethyl 4-(4-cyano-1H-indazol-1-yl)-2,2-dimethylbutanoate (D113), N6375-40

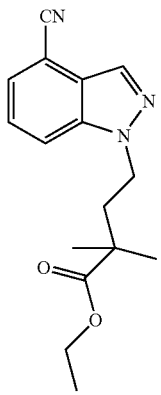

To a solution of ethyl 4-(4-bromo-1H-indazol-1-yl)-2,2-dimethylbutanoate (D112) (600 mg, 1.77 mmol) and $Zn(CN)_2$ (207 mg, 1.77 mmol) in DMF (5 ml) at room temperature was added $Pd(PPh_3)_4$ (204 mg, 0.18 mmol) and the resulting mixture was stirred at 100° C. over the weekend, heated for a further 5 hours and then cooled to room temperature and diluted with AcOEt. The organic phase was filtered through celite and washed with water then brine, dried and concentrated in vacuo. Purification of the residue by flash chromatography on silica gel [10-20% EtOAc/cyclohexane] gave the title compound (200 mg, 36%) as a colourless oil. MS (ES) $C_{16}H_{19}N_3O_2$ requires 285, found 286 $[M+H]^+$.

Description of D114

Ethyl 4-{4-[(hydroxyamino)(imino)methyl]-1H-indazol-1-yl}-2,2-dimethylbutanoate (D114)

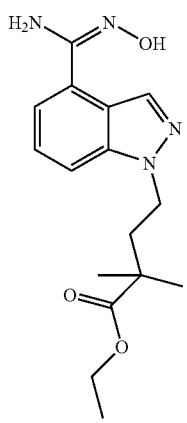

Ethyl 4-{4-[(hydroxyamino)(imino)methyl]-1H-indazol-1-yl}-2,2-dimethylbutanoate (D114) was obtained from ethyl 4-(4-cyano-1H-indazol-1-yl)-2,2-dimethylbutanoate (D113) in a similar manner to the procedure described for the synthesis of ethyl 3-{4-[(hydroxyamino)(imino)methyl]-1H-indazol-1-yl}-2,2-dimethylpropanoate (D103). Obtained 200 mg, 85% yield. MS (ES) $C_{16}H_{22}N_4O_3$ requires 318, found 319 $[M+H]^+$.

Description of D115

Ethyl 4-[4-(5-{3-cyano-4-[(1-methylethyl)oxy]phenyl}-1,2,4-oxadiazol-3-yl)-1H-indazol-1-yl]-2,2-dimethylbutanoate (D115)

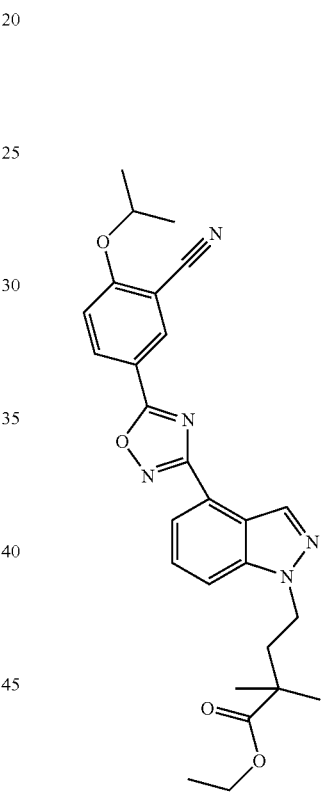

Ethyl 4-[4-(5-{3-cyano-4-[(1-methylethyl)oxy]phenyl}-1,2,4-oxadiazol-3-yl)-1H-indazol-1-yl]-2,2-dimethylbutanoate (D115) was obtained from 3-Cyano-4-[(1-methylethyl)oxy]benzoyl chloride (D106) and ethyl 4-{4-[(hydroxyamino)(imino)methyl]-1H-indazol-1-yl}-2,2-dimethylbutanoate (D114) in a similar manner to the procedure described as an alternative procedure for the synthesis of 5-[3-(1H-indazol-5-yl)-1,2,4-oxadiazol-5-yl]-2-[(1-methylethyl)oxy]benzonitrile (D43). 120 mg, 74% yield. MS (ES) $C_{27}H_{29}N_5O_4$ requires 487, found 488 $[M+H]^+$.

Description of D116

Ethyl 4-[4-(5-{5-chloro-6-[(1-methylethyl)oxy]-3-pyridinyl}-1,2,4-oxadiazol-3-yl)-1H-indazol-1-yl]-2,2-dimethylbutanoate (D116)

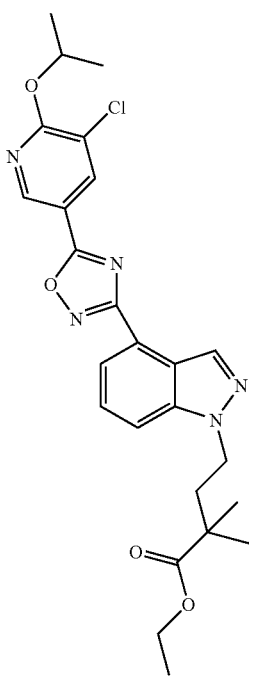

5-Chloro-6-[(1-methylethyl)oxy]-3-pyridinecarboxylic acid (D31) (67.7 mg, 0.314 mmol) then triethylamine (88 μl, 0.628 mmol) followed by HOBT (57.7 mg, 0.377 mmol), EDC (72.3 mg, 0.377) and ethyl 4-{4-[(hydroxyamino)(imino)methyl]-1H-indazol-1-yl}-2,2-dimethylbutanoate (D114) (100 mg, 0.314 mmol) were dissolved in DMF (4 ml) at room temperature then stirred at 50° C. for 5 days. The mixture was cooled to room temperature and diluted with EtOAc. The organic phase was washed with water, dried and concentrated in vacuo. Purification of the residue by flash chromatography on silica gel [15-40% EtOAc/cyclohexane] gave the title compound (110 mg, 67%) as a light yellow solid. MS (ES) $C_{25}H_{28}ClN_5O_4$ requires 497, found 498 [M+H]$^+$.

EXAMPLE 1

3-[5-(5-{3-Chloro-4-[(1-methylethyl)oxy]phenyl}-1,2,4-oxadiazol-3-yl)-1H-indazol-1-yl]propanoic acid (E1)

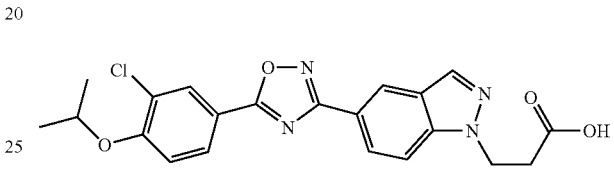

Ethyl 3-[5-(5-{3-chloro-4-[(1-methylethyl)oxy]phenyl}-1,2,4-oxadiazol-3-yl)-1H-indazol-1-yl]propanoate (D5) (240 mg) was dissolved in MeOH (5 ml), treated with 2 M aqueous NaOH (5 ml) and stirred at RT overnight and vacuumed to remove the MeOH. The reaction mixture was then diluted with 1M aqueous NaOH, washed with EtOAc (×2) and acidified to pH=3. This solution was extracted with EtOAc (×3) and the combined extracts washed with brine and evaporated to give the crude product. This was purified using the MDAP system to give the title compound (13 mg) as a white solid. δH (CDCl$_3$, 400 MHz): 1.44 (6H, d), 3.03 (2H, t), 4.68-4.75 (3H, m), 7.05 (1H, d), 7.60 (1H, d), 8.06 (1H, d), 8.11 (1H, s), 8.15 (1H, d), 8.24 (1H, s), 8.56 (1H, s). MS (ES): $C_{21}H_{19}{}^{35}ClN_4O_4$ requires 426; found 427 (MH$^+$).

EXAMPLE 1 (ALTERNATIVE PROCEDURE)

3-[5-(5-{3-Chloro-4-[(1-methylethyl)oxy]phenyl}-1,2,4-oxadiazol-3-yl)-1H-indazol-1-yl]propanoic acid (E1)

Ethyl 3-[5-(5-{3-chloro-4-[(1-methylethyl)oxy]phenyl}-1,2,4-oxadiazol-3-yl)-1H-indazol-1-yl]propanoate (D5) (1.95 g, 4.29 mmol) was dissolved in ethanol. 2M NaOH (2.143 ml, 4.29 mmol) was added and the solution was stood at R.T. for 3 hours. Ethanol was evaporated and the mixture was dissolved in EtOAc and water and acidified with acetic acid. Organic layer was dried (MgSO$_4$) and evaporated to give (1.34 g) of white solid. δH (d$_6$-DMSO, 400 MHz): 1.37 (6H, d), 2.89 (2H, t), 4.65 (2H, t), 4.89 (1H, m), 7.45 (1H, d), 7.89 (1H, d), 8.06 (1H, d), 8.12 (1H, d), 8.20 (1H, s), 8.27 (1H, s), 8.55 (1H, s). MS (ES): $C_{21}H_{19}{}^{35}ClN_4O_4$ requires 426; found 427 (MH$^+$).

EXAMPLE 2

Sodium 3-(5-{5-[3-chloro-4-(ethyloxy)phenyl]-1,2,4-oxadiazol-3-yl}-1H-indazol-1-yl)propanoate (E2)

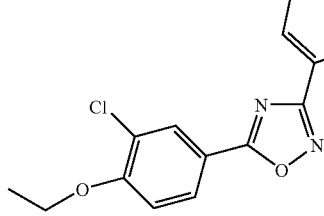

Ethyl 3-(5-{5-[3-chloro-4-(ethyloxy)phenyl]-1,2,4-oxadiazol-3-yl}-1H-indazol-1-yl)propanoate (D57) (77 mg, 0.17 mmol) was suspended in 2M aq. NaOH (2 ml) and ethanol (2 ml). The mixture was heated at 50° C. until dissolved then cooled. The ethanol was removed in vacuo and the resultant solid was filtered, washed with ethanol, water and diethyl ether then dried under high vacuum to afford the title compound (63.6 mg) as a pink solid. δH (methanol-$d_4$, 400 MHz) 1.49 (3H, t), 2.77 (2H, t), 4.25 (2H, q), 4.71 (2H, t), 7.27 (1H, d), 7.82 (1H, d), 8.09-8.25 (4H, m), 8.55 (1H, s). MS (ES): $C_{20}H_{17}{}^{35}ClN_4O_4$ requires; 412 found (MH$^+$) 413.

EXAMPLE 3

Sodium 3-[5-(5-{3-cyano-4-[(1-methylethyl)oxy]phenyl}-1,2,4-oxadiazol-3-yl)-1H-indazol-1-yl]propanoate (E3)

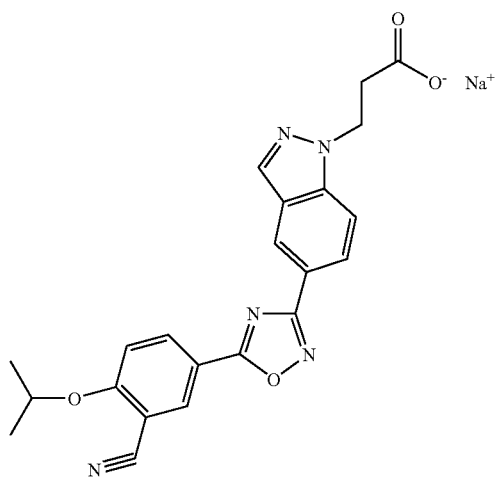

Ethyl 3-[5-(5-{3-cyano-4-[(1-methylethyl)oxy]phenyl}-1,2,4-oxadiazol-3-yl)-1H-indazol-1-yl]propanoate (D58) (99 mg, 0.22 mmol) was dissolved in ethanol (2 ml) and 2M aq NaOH (0.55 ml) was added. The reaction was heated at 80° C. for 30 minutes and the reagents dissolved. The reaction mixture was cooled to room temperature and then left overnight. The resultant precipitate was filtered, washed with water and then ether, dried by heating in vacuo to afford the title compound (29.1 mg). δH (methanol-$d_4$, 400 MHz) 1.46 (6H, d), 2.78, (2H, t), 4.71 (2H, t), 4.88-5.00 (estimate 1H [partially overlapping water peak], m). 7.43 (1H, d), 7.83 (1H, d), 8.10-8.17 (2H, m), 8.37-8.49 (2H, m), 8.56 (1H, s), MS (ES): $C_{22}H_{19}N_5O_4$ requires 417; found (MH$^+$) 418.

EXAMPLE 4

3-[5-(5-{3-Cyano-4-[(1-methylethyl)oxy]phenyl}-1,2,4-oxadiazol-3-yl)-1H-indazol-1-yl]propanoic acid (E4)

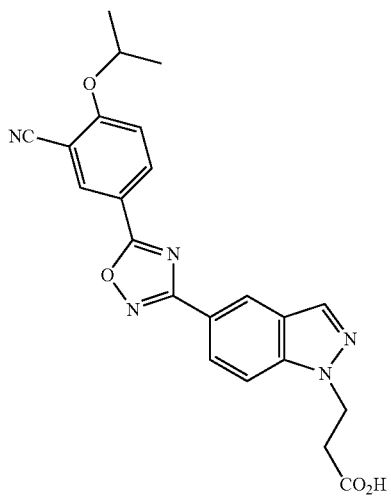

Ethyl 3-[5-(5-{3-cyano-4-[(1-methylethyl)oxy]phenyl}-1,2,4-oxadiazol-3-yl)-1H-indazol-1-yl]propanoate (D58) (523 mg, 1.17 mmol) was dissolved in mixture of ethanol (20 ml) and THF (10 ml) by warming at 50° C. Cooled to RT and added 2N NaOH (1 ml, 2 mmol) and left standing at RT for 30 minutes. Evaporated off the solvent, added water (50 ml) and washed with EtOAc (50 ml). Acidified aqueous layer and extracted product into EtOAc (50 ml). The EtOAc layer was dried (MgSO$_4$) and the solvent evaporated. Triturating with diethyl ether gave the title compound (139 mg) as a beige solid. δH ($d_6$-DMSO, 400 MHz): 1.39 (6H, d), 2.90 (2H, t), 4.66 (2H, t), 4.94-5.03 (1H, m), 7.57 (1H, d), 7.90 (1H, d), 8.07 (1H, dd), 8.28 (1H, d), 8.42 (1H, dd), 8.54 (2H, dd), 12.35 (1H, broad s). MS (ES): $C_{22}H_{19}N_5O_4$ requires 417; found (MH$^+$) 418.

EXAMPLE 5

4-[5-(5-{3-cyano-4-[(1-methylethyl)oxy]phenyl}-1,2,4-oxadiazol-3-yl)-1H-indazol-1-yl]butanoic acid (E5)

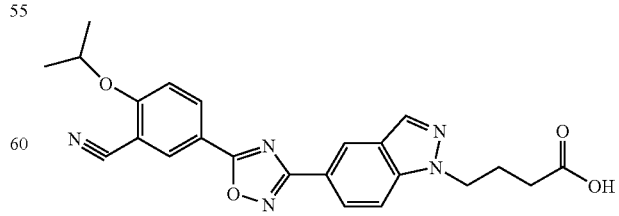

Ethyl 4-[5-(5-{3-cyano-4-[(1-methylethyl)oxy]phenyl}-1,2,4-oxadiazol-3-yl)-1H-methylethyl)oxy]phenyl}-1,2,4-oxadiazol-3-yl)-2H-indazol-2-yl]butanoate (D44) (73 mg, 0.16 mmol), 33% dimethylamine in ethanol (4 ml) was heated in the microwave for at 160° C. for 1 hour. Added 2 drops of water, and heated in the microwave at 160° C. for 3 hours. The reaction was left to cool overnight and then evaporated to dryness in vacuo. Attempted MDAP purification generated crude material.

To a solution of Ethyl 4-[5-(5-{3-cyano-4-[(1-methylethyl)oxy]phenyl}-1,2,4-oxadiazol-3-yl)-1H-methylethyl)oxy]phenyl}-1,2,4-oxadiazol-3-yl)-2H-indazol-2-yl]butanoate (D44) (65 mg, 0.14 mmol) in ethanol (10 ml) was added 2M aq. NaOH (1 ml). Heated for 1 hour at 80° C. and then left overnight at room temperature. The solvent was evaporated and the crude material purified by MDAP. The resultant material was triturated with ether and water to generate crude material.

Crude batches were combined and purified by MDAP, the fractions containing product were freeze dried to generate the title compound (11.1 mg). δH (d$_6$-DMSO, 400 MHz) 1.39 (6H, d), 2.01-2.11 (2H, m), 2.23 (2H, t), 4.50 (2H, t), 4.98 (1H, sept), 7.56 (1H, d), 7.86 (1H, d), 8.07 (1H, dd), 8.28 (1H, d), 8.42 (1H, dd), 8.52 (1H, d), 8.57 (1H, dd). MS (ES): C$_{23}$H$_{21}$N$_5$O$_4$ requires 431; found (MH$^+$) 432.

EXAMPLE 6

3-(5-{5-[4-[(1-Methylethyl)oxy]-3-(trifluoromethyl)phenyl]-1,2,4-oxadiazol-3-yl}-1H-indazol-1-yl)propanoic acid (E6)

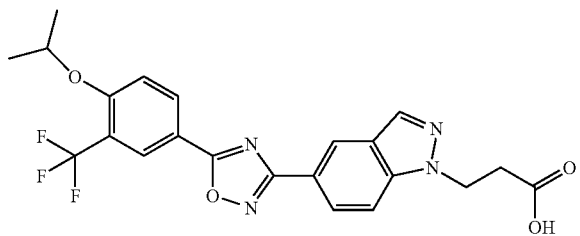

Ethyl 3-(5-{5-[4-[(1-methylethyl)oxy]-3-(trifluoromethyl)phenyl]-1,2,4-oxadiazol-3-yl}-1H-indazol-1-yl)propanoate (D59) (82 mg, 0.17 mmol) was dissolved in ethanol (4 ml) and then 2M aq. NaOH added (0.5 ml). The reaction was stirred at room temperature overnight and then the ethanol was evaporated in vacuo. Ethyl acetate was added but as the compound appeared to be in both aqueous and organic layers the mixture was evaporated. Purification by MDAP (in two batches) followed by freeze-drying gave the title compound (28.7 mg). δH (400 MHz, d$_6$-DMSO) 1.36 (6H, d), 2.88 (2H, t), 4.65 (2H, t), 4.98 (1H, sept.), 7.59 (1H, d), 7.89 (1H, d), 8.07 (1H, dd), 8.27 (1H, d), 8.32 (1H, d), 8.41 (1H, dd), 8.57 (1H, dd). MS (ES): C$_{22}$H$_{19}$F$_3$N$_4$O$_4$ requires 460; found (MH$^+$) 461.

EXAMPLE 7

4-[4-(5-{3-Chloro-4-[(1-methylethyl)oxy]phenyl}-1,2,4-oxadiazol-3-yl)-1H-indazol-1-yl]butanoic acid (E7)

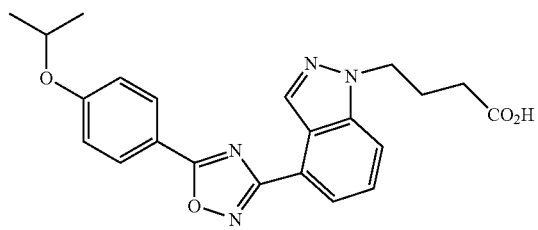

2M Sodium hydroxide (1 ml, 2 mmol) was added to a solution of ethyl 4-[4-(5-{3-chloro-4-[(1-methylethyl)oxy]phenyl}-1,2,4-oxadiazol-3-yl)-1H-indazol-1-yl]butanoate (D60) (N2666-13-A1) (0.062 g, 0.132 mmol) in ethanol (5 ml) and the reaction was heated to 80° C. to effect dissolution then left to cool for 2 hours. Evaporated, dissolved in ethyl acetate/water (25 ml of each) and acidified with acetic acid. Organic dried (magnesium sulphate), evaporated, azeotroped with 15 ml of toluene and triturated with ether. Filtered to give the title compound (42 mg) as a white solid. δH (d$_6$-DMSO, 400 MHz): 1.37 (6H, d), 2.09 (2H, m), 2.24 (2H, t), 4.54 (2H, t), 4.90 (1H, m), 7.47 (1H, d), 7.62 (1H, dd), 7.97 (1H, d), 8.01 (1H, d), 8.17 (1H, dd), 8.26 (1H, d), 8.56 (1H, s). MS (ES): C$_{22}$H$_{21}$$^{35}$ClN$_4$O$_4$ requires 440; found (MH$^+$) 441.

EXAMPLE 7 (ALTERNATIVE PROCEDURE)

4-[4-(5-{3-Chloro-4-[(1-methylethyl)oxy]phenyl}-1,2,4-oxadiazol-3-yl)-1H-indazol-1-yl]butanoic acid (E7)

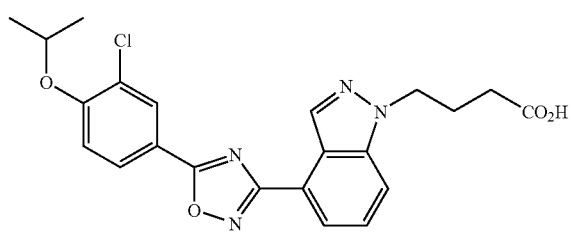

A solution of ethyl 4-[4-(5-{3-chloro-4-[(1-methylethyl)oxy]phenyl}-1,2,4-oxadiazol-3-yl)-1H-indazol-1-yl]butanoate (D60) (1.5 g, 3.20 mmol) in hot ethanol (15 ml) was treated with sodium hydroxide (7.5 ml, 15.00 mmol) and stood for 1 hr. The solvents were evaporated and the residue partitioned between ethyl acetate/water. Acetic acid was added to adjust the pH to 5 and the layers separated. The organic layer was dried over magnesium sulphate and evaporated. The crude material was triturated with ether to give the title compound (1.1 g) as a white solid. δH (d$_6$-DMSO, 400 MHz): 1.37 (6H, d), 2.08 (2H, m), 2.23 (2H, t), 4.54 (2H, t), 4.90 (1H, m), 7.47 (1H, d), 7.62 (1H, dd), 7.97 (1H, d), 8.01 (1H, d), 8.17 (1H, dd), 8.26 (1H, d), 8.56 (1H, s), MS (ES): $C_{22}H_{21}{}^{35}ClN_4O_4$ requires 440; found (MH$^+$) 441.

EXAMPLE 8

3-[4-(5-{3-Chloro-4-[(1-methylethyl)oxy]phenyl}-1,2,4-oxadiazol-3-yl)-1H-indazol-1-yl]propanoic acid (E8)

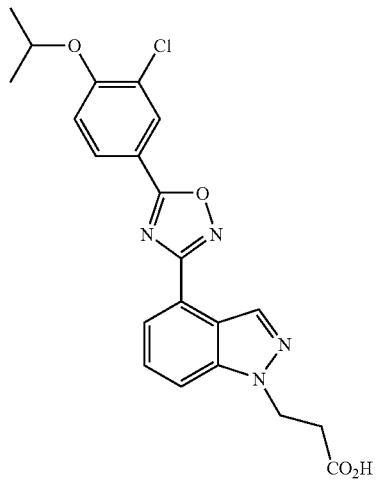

Ethyl 3-[4-(5-{3-chloro-4-[(1-methylethyl)oxy]phenyl}-1,2,4-oxadiazol-3-yl)-1H-indazol-1-yl]propanoate (D61) (380 mg, 0.835 mmol) was dissolved in hot ethanol (4 ml), 2M sodium hydroxide (2 ml, 4.00 mmol) added and the solution stirred for 30 mins. Precipitate had formed. The ethanol was evaporated and the residue partitioned between EtOAc/water. The aqueous layer was neutralised with AcOH and the layers separated. The organic layer was dried over magnesium sulphate and evaporated. The crude material was triturated with ether to give (240 mg) white solid. δH (d$_6$-DMSO) 1.36 (6H, d), 2.90 (2H, t), 4.68 (2H, t), 4.89 (1H, m), 7.46 (1H, d), 7.59 (1H, t), 7.99 (2H, d), 8.16 (1H, dd), 8.25 (1H, d), 8.55 (1H, s), 11.90 (1H, br. s). MS (ES): $C_{21}H_{19}{}^{35}ClN_4O_4$ requires 426; found (MH$^+$) 427.

The following examples were made by similar hydrolysis reactions. Unless otherwise stated the reactions were performed at between room temperature and 80° C. The reaction solvent was a mixture of ethanol and 2M NaOH (aq). On some occasions an additional solvent such as DCM was added to aid dissolution. In some cases alternative solvents such as DCM were used instead of EtOAc in the work-up procedure. In some cases the reaction mixture was acidified (using either acetic acid or hydrochloric acid) to generate the carboxylic acid whilst in other cases the product was isolated as the sodium salt. In some cases evaporation of some of the reaction solvent caused the product to precipitate and this material could be isolated by filtration. Alternatively, the carboxylic acid was sometimes isolated and then converted to the sodium salt by treatment with sodium hydroxide. In the case of E23, E24, the use of hydrochloric acid to acidify the reaction on work-up generated the hydrochloride salt. The compounds were purified by either MDAP or trituration. Freeze drying was sometimes used to generate solid material.

| Example | Structure | Name | Precursor | MS |
|---|---|---|---|---|
| E9 | 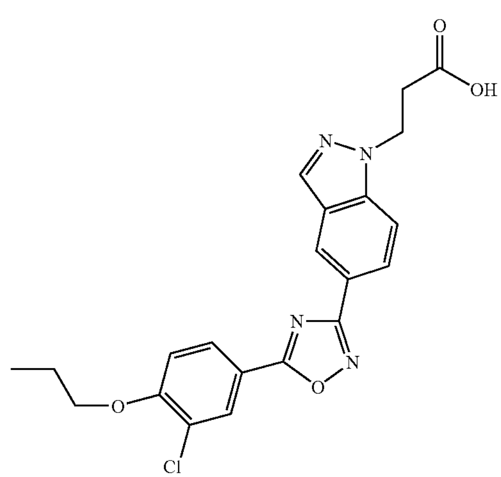 | 3-(5-{5-[3-chloro-4-(propyloxy)phenyl]-1,2,4-oxadiazol-3-yl}-1H-indazol-1-yl)propanoic acid | D62 | [MH$^+$] 427 |

| Example | Structure | Name | Precursor | MS |
|---|---|---|---|---|
| E10 | 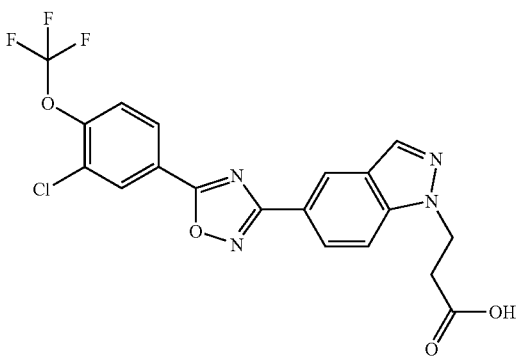 | 3-[5-(5-{3-chloro-4-[(trifluoromethyl)oxy]phenyl}-1,2,4-oxadiazol-3-yl)-1H-indazol-1-yl]propanoic acid | D65 | [MH+] 453 |
| E11 | 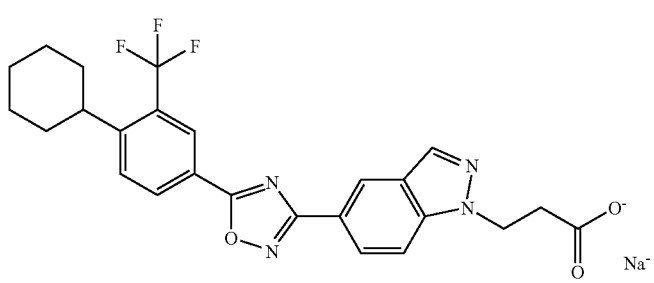 | sodium 3-(5-{5-[4-cyclohexyl-3-(trifluoromethyl)phenyl]-1,2,4-oxadiazol-3-yl}-1H-indazol-1-yl)propanoate | D66 | [MH+] 485 |
| E12 | 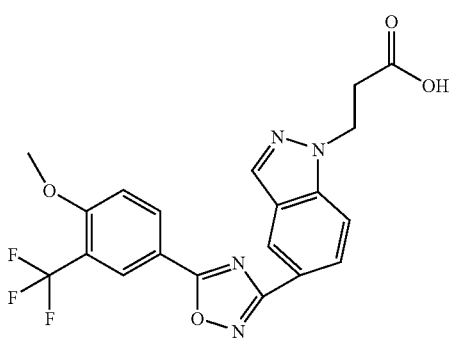 | 3-(5-{5-[4-(methyloxy)-3-(trifluoromethyl)phenyl]-1,2,4-oxadiazol-3-yl}-1H-indazol-1-yl)propanoic acid | D67 | [MH+] 433 |
| E13 | 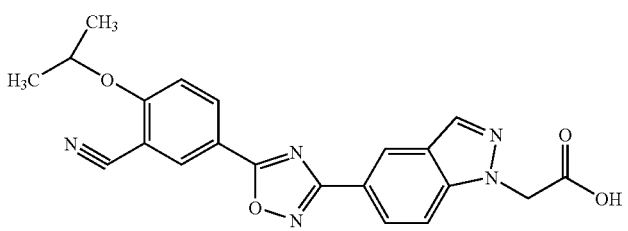 | [5-(5-{3-cyano-4-[(1-methylethyl)oxy]phenyl}-1,2,4-oxadiazol-3-yl)-1H-indazol-1-yl]acetic acid | D46 | [MH+] 404 |

| Example | Structure | Name | Precursor | MS |
|---|---|---|---|---|
| E14 | 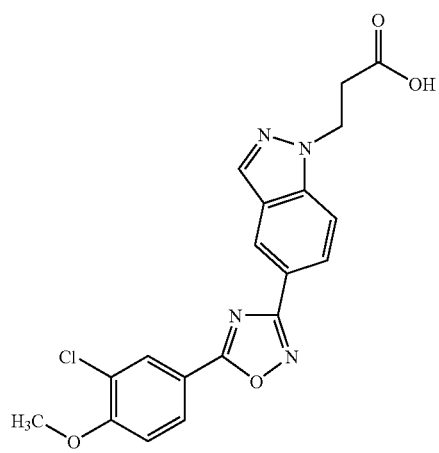 | 3-(5-{5-[3-chloro-4-(methyloxy)phenyl]-1,2,4-oxadiazol-3-yl}-1H-indazol-1-yl)propanoic acid | D68 | [MH+] 399 |
| E15 | 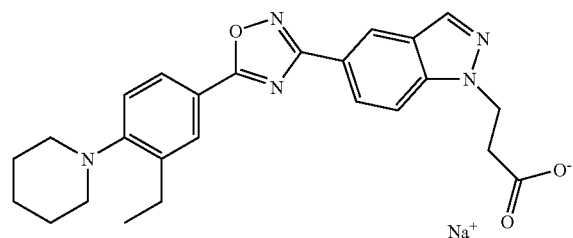 | sodium 3-(5-{5-[3-ethyl-4-(1-piperidinyl)phenyl]-1,2,4-oxadiazol-3-yl}-1H-indazol-1-yl)propanoate | D69 | [MH+] 446 |
| E16 | 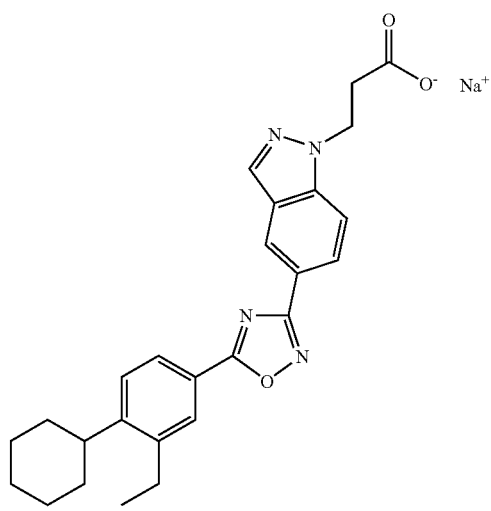 | sodium 3-{5-[5-(4-cyclohexyl-3-ethylphenyl)-1,2,4-oxadiazol-3-yl]-1H-indazol-1-yl}propanoate | D70 | [MH+] 445 |

| Example | Structure | Name | Precursor | MS |
|---|---|---|---|---|
| E17 | 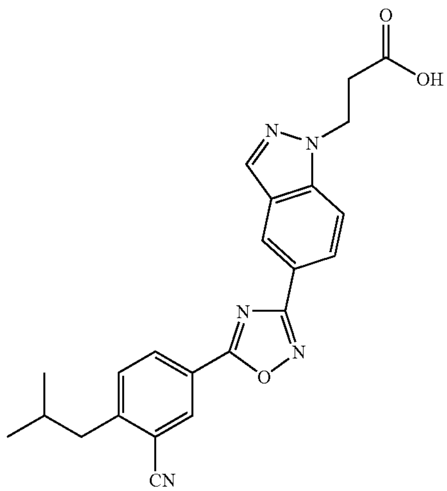 | 3-(5-{5-[3-cyano-4-(2-methylpropyl)phenyl]-1,2,4-oxadiazol-3-yl}-1H-indazol-1-yl)propanoic acid | D71 | [MH$^+$] 416 |
| E18 | 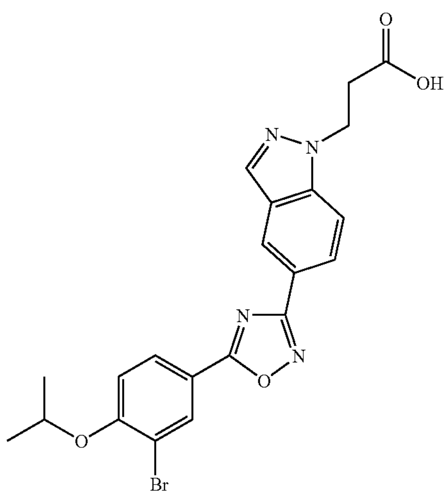 | 3-[5-(5-{3-bromo-4-[(1-methylethyl)oxy]phenyl}-1,2,4-oxadiazol-3-yl)-1H-indazol-1-yl]propanoic acid | D72 | [MH$^+$] 471, 473 |
| E19 | 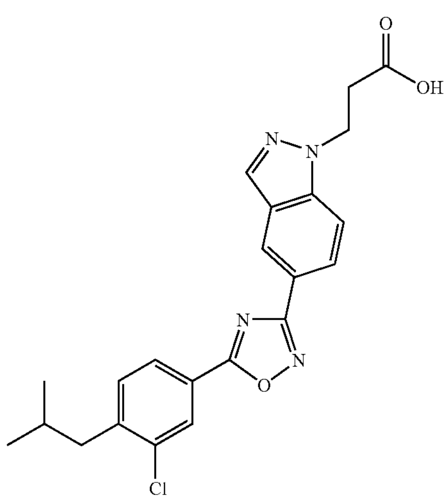 | 3-(5-{5-[3-chloro-4-(2-methylpropyl)phenyl]-1,2,4-oxadiazol-3-yl}-1H-indazol-1-yl)propanoic acid | D73 | [MH$^+$] 425, 427 |

| Example | Structure | Name | Precursor | MS |
|---|---|---|---|---|
| E20 | 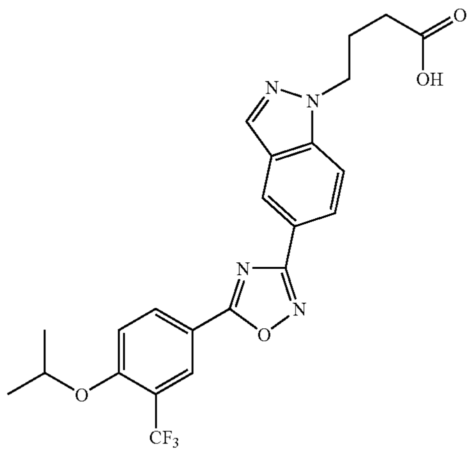 | 4-(5-{5-[4-[(1-methylethyl)oxy]-3-(trifluoromethyl)phenyl]-1,2,4-oxadiazol-3-yl}-1H-indazol-1-yl)butanoic acid | D74 | [MH+] 475 |
| E21 | 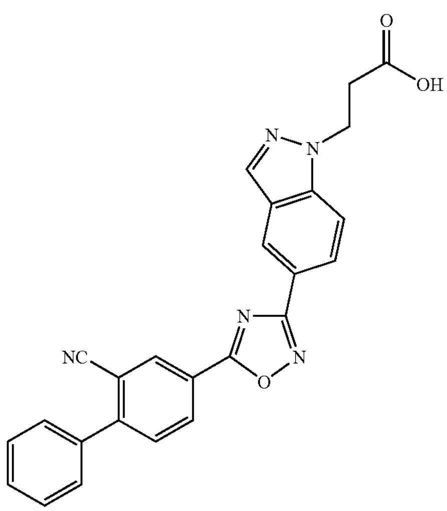 | 3-{5-[5-(2-cyano-4-biphenylyl)-1,2,4-oxadiazol-3-yl]-1H-indazol-1-yl}propanoic acid | D75 | [M − H+] 434 |
| E22 | 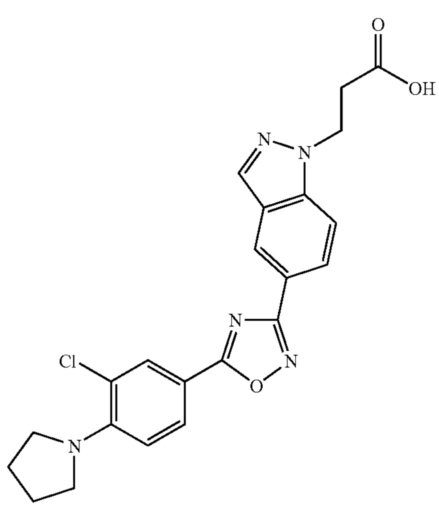 | 3-(5-{5-[3-chloro-4-(1-pyrrolidinyl)phenyl]-1,2,4-oxadiazol-3-yl}-1H-indazol-1-yl)propanoic acid | D76 | [M − H+] 436, 438 |

-continued
| Example | Structure | Name | Precursor | MS |
|---|---|---|---|---|
| E23 | 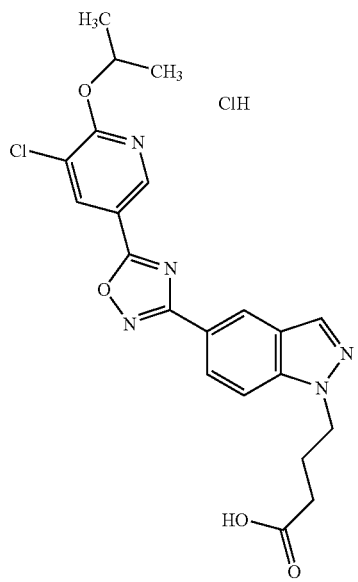 | 4-[5-(5-{5-chloro-6-[(1-methylethyl)oxy]-3-pyridinyl}-1,2,4-oxadiazol-3-yl)-1H-indazol-1-yl]butanoic acid hydrochloride | D77 | [MH$^+$] for $^{35}$Cl 442 |
| E24 | 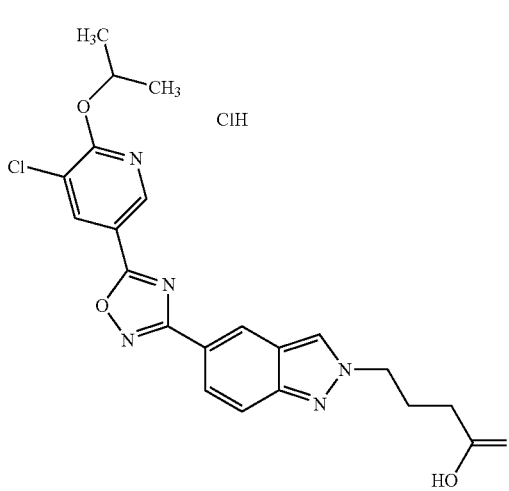 | 4-[5-(5-{5-chloro-6-[(1-methylethyl)oxy]-3-pyridinyl}-1,2,4-oxadiazol-3-yl)-2H-indazol-2-yl]butanoic acid hydrochloride | D78 | [MH$^+$] for $^{35}$Cl 442 |

| Example | Structure | Name | Precursor | MS |
|---|---|---|---|---|
| E25 | 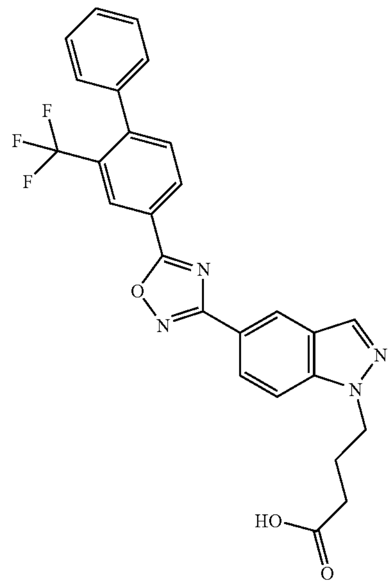 | 4-(5-{5-[2-(trifluoromethyl)-4-biphenylyl]-1,2,4-oxadiazol-3-yl}-1H-indazol-1-yl)butanoic acid | D79 | [MH+] 493 |
| E26 | 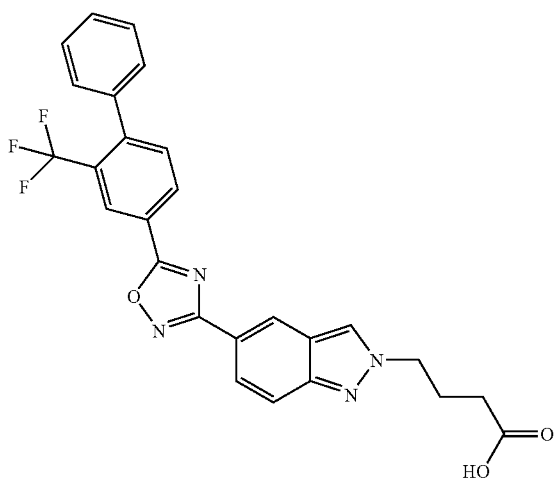 | 4-(5-{5-[2-(trifluoromethyl)-4-biphenylyl]-1,2,4-oxadiazol-3-yl}-2H-indazol-2-yl)butanoic acid | D80 | [MH+] 493 |
| E27 | 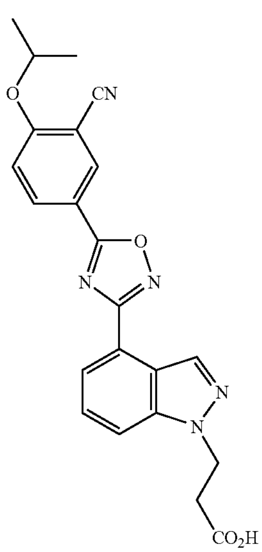 | 3-[4-(5-{3-cyano-4-[(1-methylethyl)oxy]phenyl}-1,2,4-oxadiazol-3-yl)-1H-indazol-1-yl]propanoic acid | D81 | [MH+] 418 |

-continued

| Example | Structure | Name | Precursor | MS |
|---|---|---|---|---|
| E28 | 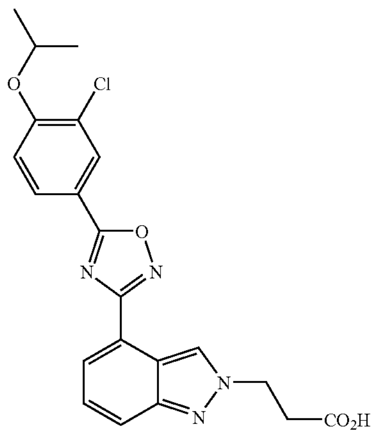 | 3-[4-(5-{3-chloro-4-[(1-methylethyl)oxy]phenyl}-1,2,4-oxadiazol-3-yl)-2H-indazol-2-yl]propanoic acid | D82 | [MH+] 427 |
| E29 | 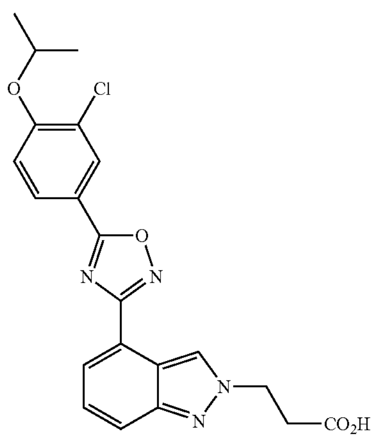 | 3-[4-(5-{3-cyano-4-[(1-methylethyl)oxy]phenyl}-1,2,4-oxadiazol-3-yl)-2H-indazol-2-yl]propanoic acid | D83 | [MH+] 418 |
| E30 | 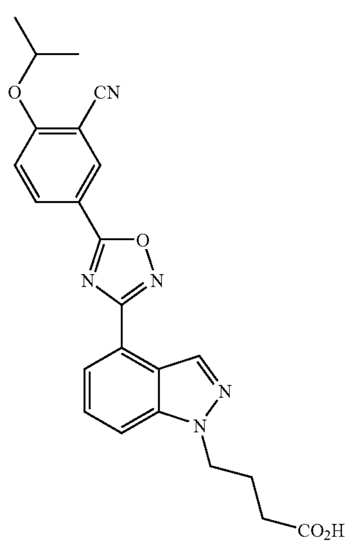 | 4-[4-(5-{3-cyano-4-[(1-methylethyl)oxy]phenyl}-1,2,4-oxadiazol-3-yl)-1H-indazol-1-yl]butanoic acid | D84 | [MH+] 432 |

| Example | Structure | Name | Precursor | MS |
|---|---|---|---|---|
| E31 | 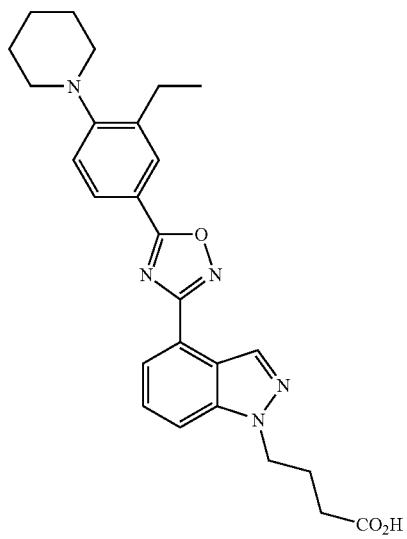 | 4-(4-{5-[3-ethyl-4-(1-piperidinyl)phenyl]-1,2,4-oxadiazol-3-yl}-1H-indazol-1-yl)butanoic acid | D85 | [MH+] 460 |
| E32 | 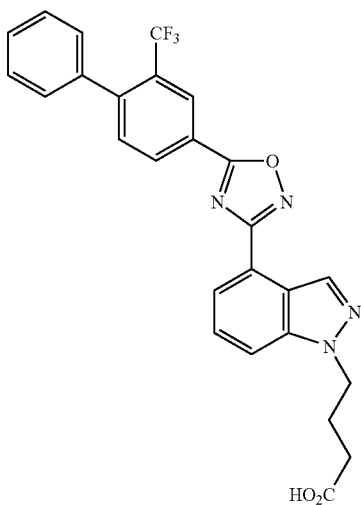 | 4-(4-{5-[2-(trifluoromethyl)-4-biphenylyl]-1,2,4-oxadiazol-3-yl}-1H-indazol-1-yl)butanoic acid | D86 | [MH+] 493 |
| E33 | 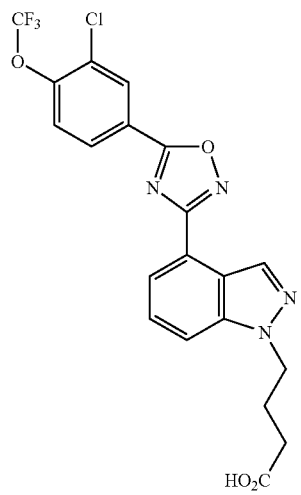 | 4-[4-(5-{3-chloro-4-[(trifluoromethyl)oxy]phenyl}-1,2,4-oxadiazol-3-yl)-1H-indazol-1-yl]butanoic acid | D87 | [MH+] 467 |

| Example | Structure | Name | Precursor | MS |
|---|---|---|---|---|
| E34 | 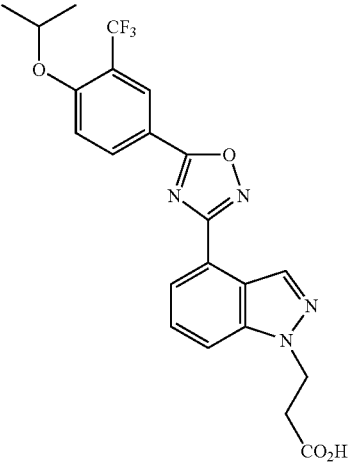 | 3-(4-{5-[4-[(1-methylethyl)oxy]-3-(trifluoromethyl)phenyl]-1,2,4-oxadiazol-3-yl}-1H-indazol-1-yl)propanoic acid | D88 | [MH+] 461 |
| E35 | 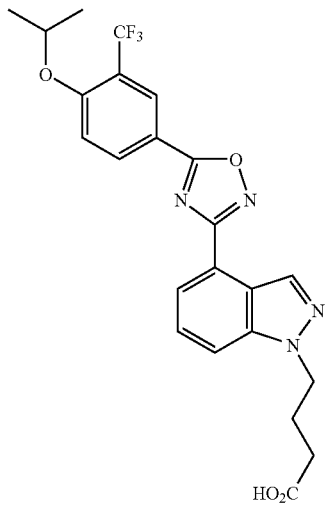 | 4-(4-{5-[4-[(1-methylethyl)oxy]-3-(trifluoromethyl)phenyl]-1,2,4-oxadiazol-3-yl}-1H-indazol-1-yl)butanoic acid | D89 | [MH+] 475 |
| E36 | 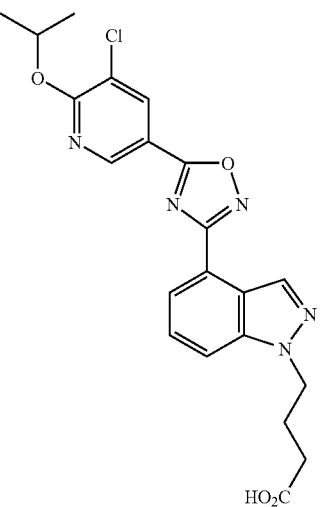 | 4-[4-(5-{5-chloro-6-[(1-methylethyl)oxy]-3-pyridinyl}-1,2,4-oxadiazol-3-yl)-1H-indazol-1-yl]butanoic acid | D90 | [MH+] 442 |

-continued
| Example | Structure | Name | Precursor | MS |
|---|---|---|---|---|
| E37 | 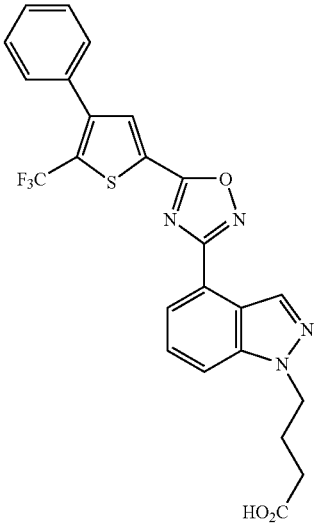 | 4-(4-{5-[4-phenyl-5-(trifluoromethyl)-2-thienyl]-1,2,4-oxadiazol-3-yl}-1H-indazol-1-yl)butanoic acid | D91 | [MH+] 499 |
| E38 | 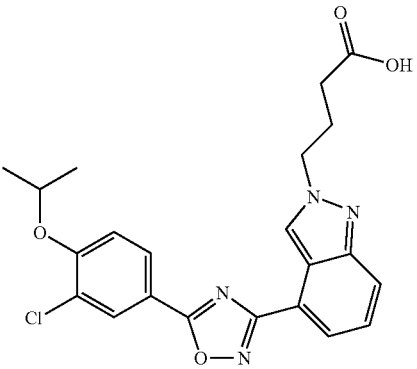 | 4-[4-(5-{3-chloro-4-[(1-methylethyl)oxy]phenyl}-1,2,4-oxadiazol-3-yl)-2H-indazol-2-yl]butanoic acid | D92 | [MH+] 441 |
| E39 | 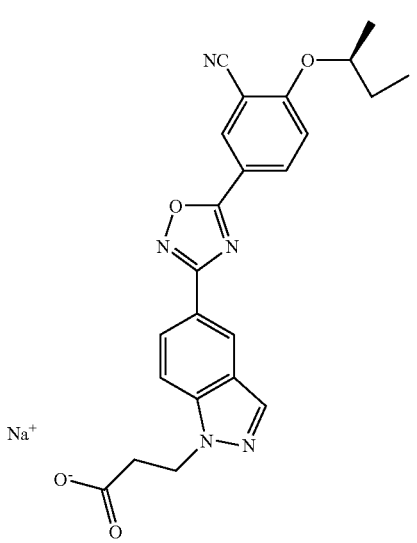 | 3-{5-[5-(3-cyano-4-{[(1S)-1-methylpropyl]oxy}phenyl)-1,2,4-oxadiazol-3-yl]-1H-yl}propanoic acid sodium salt | D93 | [MH+] 432 |

-continued

| Example | Structure | Name | Precursor | MS |
|---|---|---|---|---|
| E40 | 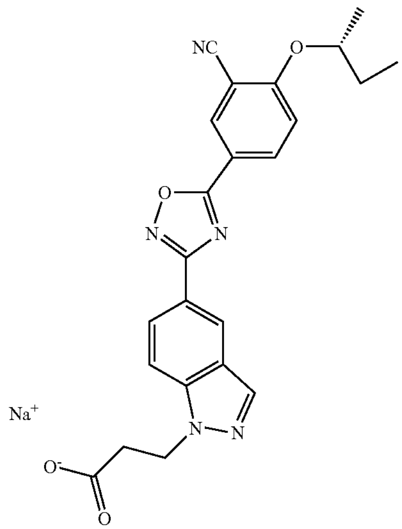 | 3-{5-[5-(3-cyano-4-{[(1R)-1-methylpropyl]oxy}phenyl)-1,2,4-oxadiazol-3-yl]-1H-indazol-1-yl}propanoic acid sodium salt | D94 | [MH+] 432 |
| E41 | 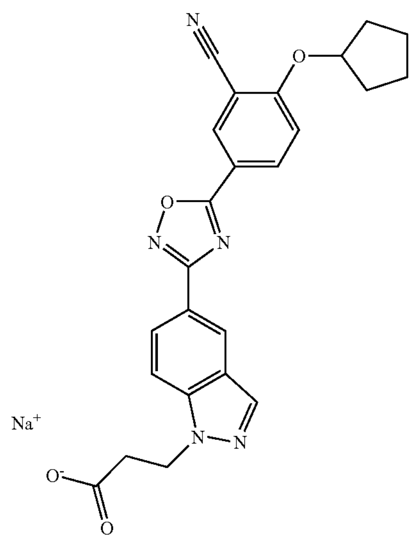 | 3-(5-{5-[3-cyano-4-(cyclopentyloxy)phenyl]-1,2,4-oxadiazol-3-yl}-1H-indazol-1-yl)propanoic acid sodium salt | D95 | [MH+] 444 |

EXAMPLE 42

4-[5-(5-{3-Chloro-4-[(1-methylethyl)oxy]phenyl}-1,2,4-oxadiazol-3-yl)-1H-indazol-1-yl]butanoic acid (E42)

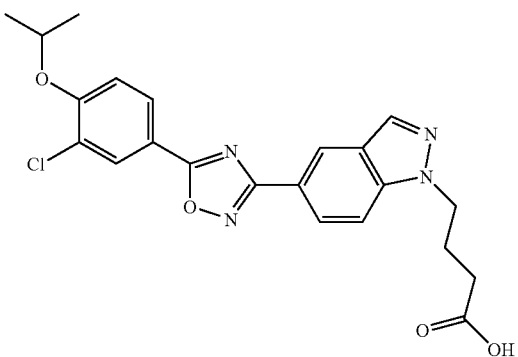

Ethyl 4-[5-(5-{3-chloro-4-[(1-methylethyl)oxy]phenyl}-1,2,4-oxadiazol-3-yl)-1H-indazol-1-yl]butanoate (D63) (127 mg, 0.27 mmol) was dissolved in ethanol (5 ml) and then sodium hydroxide (11 mg) was added. The reaction mixture was heated at 100° C. for 1 hour in a microwave reactor and then allowed to cool. The resultant solid was separated by filtration and then washed with acetone. Purification by MDAP, followed by freeze drying of the resultant material afforded the title compound (38.1 mg). MS (ES): $C_{22}H_{21}{}^{35}ClN_4O_4$ requires 440; found (MH+) 441.

The following examples were prepared using a similar method to that described above.

| Example | Structure | Name | Precursor | MS |
|---|---|---|---|---|
| E43 | 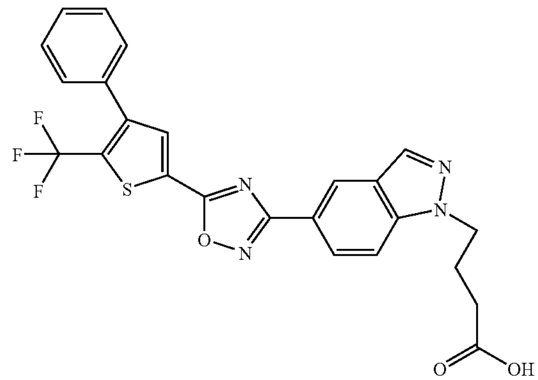 | 4-(5-{5-[4-phenyl-5-(trifluoromethyl)-2-thienyl]-1,2,4-oxadiazol-3-yl}-1H-indazol-1-yl)butanoic acid | D64 | [MH+] 499 |

EXAMPLE 44

4-[5-(5-{3-[Cyano-4-[(1-methylethyl)oxy]phenyl}-1,2,4-oxadiazol-3-yl)-2H-indazol-2-yl]buanoic acid (E44)

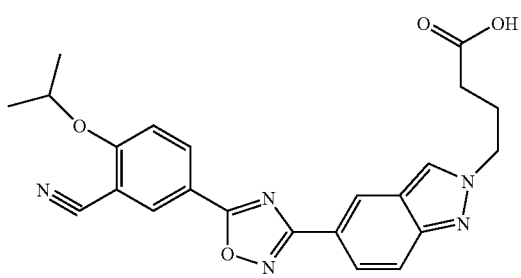

Ethyl 4-[5-(5-{3-cyano-4-[(1-methylethyl)oxy]phenyl}-1,2,4-oxadiazol-3-yl)-2H-indazol-2-yl]butanoate (D45) (60 mg, 0.13 mmol) was added to a solution of dimethylamine in ethanol (4 ml) followed by the addition of a few drops of water. The mixture was heated to 160° C. in a microwave reactor for four hours and then left to cool. The solvent was removed in vacuo and the crude material was purified by MDAP to afford the title compound (28.3 mg) as a white solid. MS (ES): $C_{23}H_{21}N_5O_4$ requires 431; found (MH+) 432.

EXAMPLE 45

3-[5-(5-{3-Chloro-4-[(1-methylethyl)oxy]phenyl}-1,2,4-oxadiazol-3-yl)-1H-indazol-1-yl]-2,2-dimethylpropanoic acid (E45)

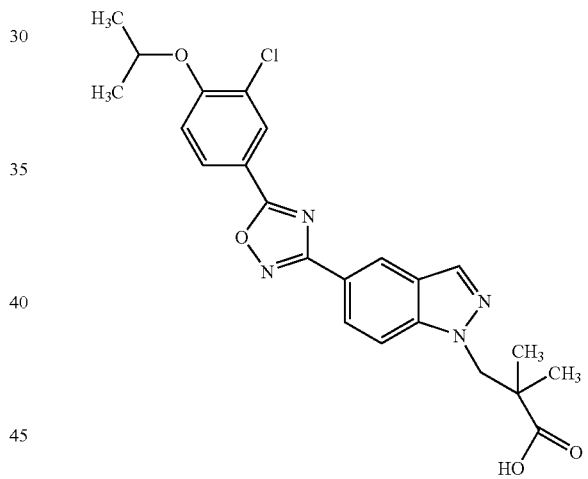

To a solution of ethyl 3-[5-(5-{3-chloro-4-[(1-methylethyl)oxy]phenyl}-1,2,4-oxadiazol-3-yl)-1H-indazol-1-yl]-2,2-dimethylpropanoate (D100) (85 mg, 176 mmol) in THF (2 ml) at room temperature was added NaOH (2N in $H_2O$, 440 µl, 880 mmol) and the resulting mixture was stirred at 50° C. overnight. NaOH (2N in $H_2O$, 440 µl, 880 mmol) and THF (2 ml) were added and the resulting mixture stirred at 80° C. for two nights then cooled to room temperature. Most of THF was removed in vacuo and the resulting aqueous phase was acidified to pH 3. The precipitate formed was filtered off and washed with $H_2O$ then dried at 60° C. under vacuum to give the title compound (73 mg, 91%) as a white solid. MS (ES): $C_{23}H_{23}ClN_4O_4$ requires 454; found (MH+) 455.

The following examples were prepared using a similar method to that described for Example 45 (E45), using EtOH rather than THF as organic solvent:

| Example | Structure | Name | Precursor | MS |
|---|---|---|---|---|
| E46 | 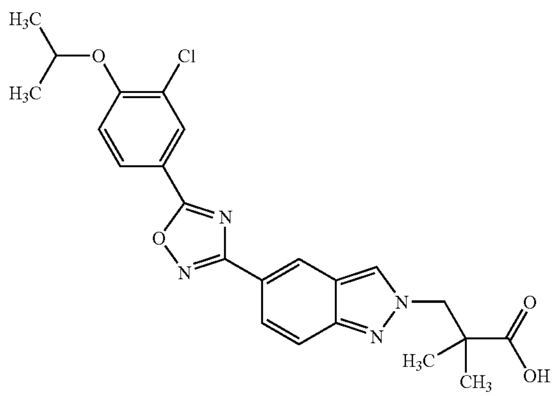 | 3-[5-(5-{3-Chloro-4-[(1-methylethyl)oxy]phenyl}-1,2,4-oxadiazol-3-yl)-2H-indazol-2-yl]-2,2-dimethylpropanoic acid | D101 | [MH+] 455 |
| E47 | 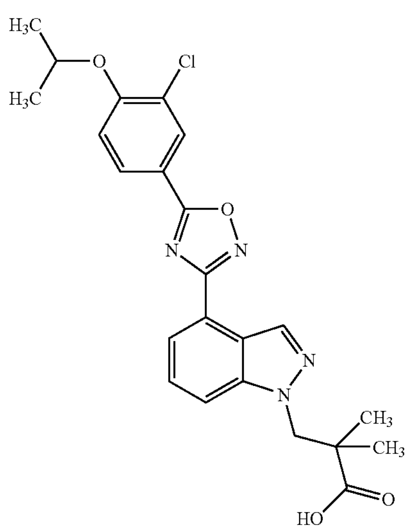 | 3-[4-(5-{3-Chloro-4-[(1-methylethyl)oxy]phenyl}-1,2,4-oxadiazol-3-yl)-1H-indazol-1-yl]-2,2-dimethylpropanoic acid | D104 | [MH+] 455 |

EXAMPLE 48

3-[4-(5-{5-Chloro-6-[(1-methylethyl)oxy]-3-pyridinyl}-1,2,4-oxadiazol-3-yl)-1H-indazol-1-yl]-2,2-dimethylpropanoic acid (E48)

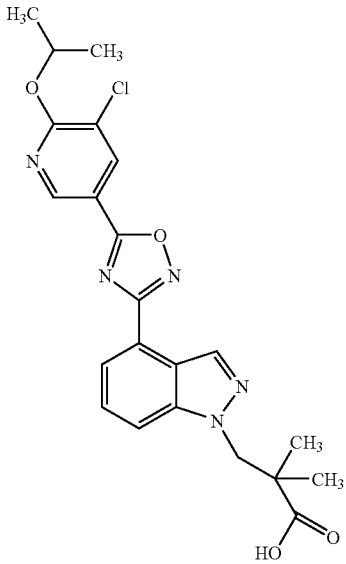

Ethyl 3-[4-(5-{5-chloro-6-[(1-methylethyl)oxy]-3-pyridinyl}-1,2,4-oxadiazol-3-yl)-1H-indazol-1-yl]-2,2-dimethylpropanoate (D105) (50 mg, 0.103 mmol) was dissolved in ethanol (10 ml). Sodium hydroxide (2N in H$_2$O, 0.258 ml, 0.517 mmol) was added and the resulting mixture was stirred at 60° C. overnight then cooled to room temperature. Solvent was evaporated, then the residue was diluted with water. The aqueous phase was neutralised with a 2N HCl aqueous solution then extracted with EtOAc. The organic phase was washed with H$_2$O, dried over MgSO$_4$ and concentrated in vacuo to give the title compound (22 mg, 42%) as an off-white solid. MS (ES): C$_{22}$H$_{22}$ClN$_5$O$_4$ requires 455; found (MH$^+$) 456.

EXAMPLE 49

3-[5-(5-{3-Cyano-4-[(1-methylethyl)oxy]phenyl}-1,2,4-oxadiazol-3-yl)-1H-indazol-1-yl]-2,2-dimethylpropanoic acid (E49)

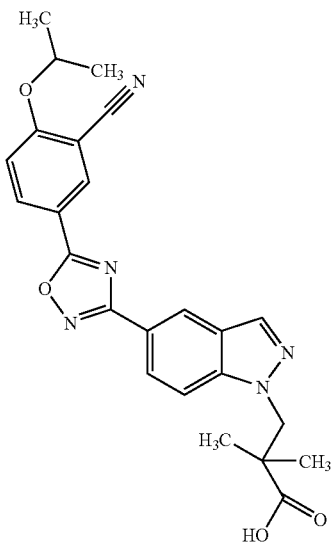

Ethyl 3-[5-(5-{3-cyano-4-[(1-methylethyl)oxy]phenyl}-1,2,4-oxadiazol-3-yl)-1H-indazol-1-yl]-2,2-dimethylpropanoate (D107) (50 mg, 0.106 mmol) was dissolved in Ethanol (10 ml). Sodium hydroxide (2N in H$_2$O, 0.264 ml, 0.528 mmol) was added and the resulting mixture was stirred at room temperature for 2 h. Most of the solvent was removed in vacuo, and the residue was diluted with water. The aqueous phase was neutralised with a 2N HCl aqueous solution then extracted with EtOAc. The organic phase was washed with H$_2$O, dried over MgSO$_4$ and concentrated in vacuo to give the title compound (15 mg, 30%) as a light yellow solid. MS (ES): C$_{23}$H$_{24}$N$_5$O$_4$ requires 445; found (MH$^+$) 446.

EXAMPLE 50

4-[5-(5-{3-Cyano-4-[(1-methylethyl)oxy]phenyl}-1,2,4-oxadiazol-3-yl)-1H-indazol-1-yl]-2,2-dimethylbutanoic acid (E50)

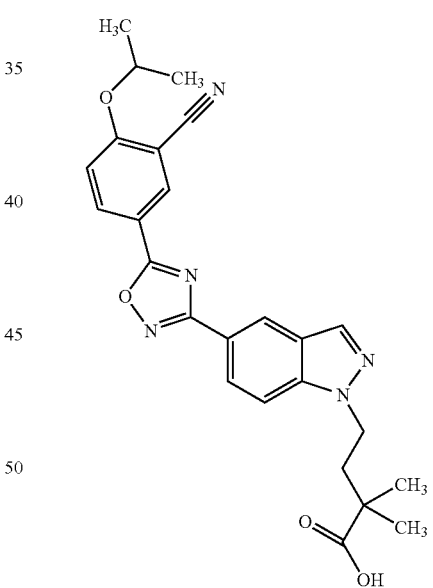

The title compound (E50) was obtained from ethyl 4-[5-(5-{3-cyano-4-[(1-methylethyl)oxy]phenyl}-1,2,4-oxadiazol-3-yl)-1H-indazol-1-yl]-2,2-dimethylbutanoate (D108) using an similar procedure to the preparation of Example 49 (E49) (16 mg, 32%). MS (ES): C$_{25}$H$_{25}$N$_5$O$_4$ requires 459; found (MH$^+$) 460.

EXAMPLE 51

3-[4-(5-{3-Cyano-4-[(1-methylethyl)oxy]phenyl}-1,2,4-oxadiazol-3-yl)-1H-indazol-1-yl]-2,2-dimethylpropanoic acid (E51)

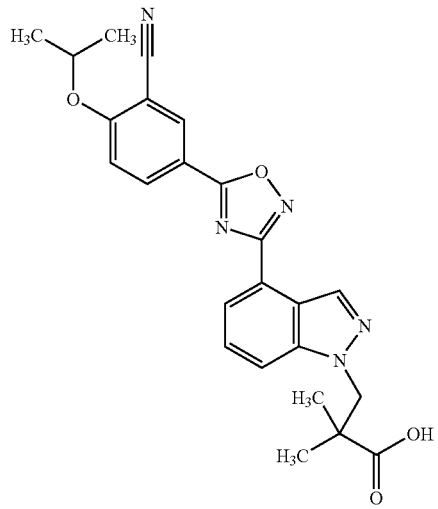

A solution of ethyl 3-[4-(5-{3-cyano-4-[(1-methylethyl)oxy]phenyl}-1,2,4-oxadiazol-3-yl)-1H-indazol-1-yl]-2,2-dimethylpropanoate (D109) (100 mg, 0.21 mmol) in ethanol (2 ml) was treated with 2M sodium hydroxide aqueous solution (1 ml, large excess) and heated at 80° C. for 2 hours. The reaction mixture was cooled and most the ethanol was removed in vacuo. The residue was diluted with water (3 ml) and acidified with a concentrated.HCl aqueous solution and extracted with EtOAc (3×10 ml). The combined extracts were dried and concentrated in vacuo. Purification of the residue by MDAP gave the desired product (5 mg, 5%) as a colourless solid. MS (ES) $C_{24}H_{23}N_5O_4$ requires 445; found (MH+) 446.

EXAMPLE 52

3-[5-(5-{5-Chloro-6-[(1-methylethyl)oxy]-3-pyridinyl}-1,2,4-oxadiazol-3-yl)-1H-indazol-1-yl]-2,2-dimethylpropanoic acid (E52)

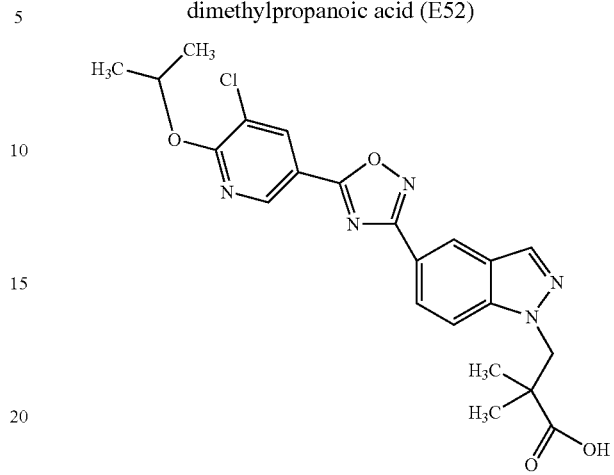

A solution of ethyl 3-[5-(5-{5-chloro-6-[(1-methylethyl)oxy]-3-pyridinyl}-1,2,4-oxadiazol-3-yl)-1H-indazol-1-yl]-2,2-dimethylpropanoate (D111) (100 mg, 0.21 mmol) in Ethanol (2 ml) was treated with a 2M sodium hydroxide aqueous solution (1 ml) and heated at 80° C. with stirring for 4 hours. The reaction mixture was cooled to room temperature and diluted with water (5 ml). The aqueous solution was acidified with glacial acetic acid, and extracted with EtOAc (2×10 ml). The combined organic phases were dried over $MgSO_4$ and concentrated in vacuo. Purification of the residue by MDAP gave the desired product (3 mg, 3%) as a colourless solid. MS (ES): $C_{22}H_{22}ClN_5O_4$ requires 455; found (MH+) 456.

The following examples were prepared using a similar method to that described for Example 48 (E48)

| Example | Structure | Name | Precursor | MS |
|---|---|---|---|---|
| E53 | ![structure] | 4-[4-(5-{3-Cyano-4-[(1-methylethyl)oxy]phenyl}-1,2,4-oxadiazol-3-yl)-1H-indazol-1-yl]-2,2-dimethylbutanoic acid | D115 | [MH+] 460 |

| Example | Structure | Name | Precursor | MS |
|---|---|---|---|---|
| E54 | 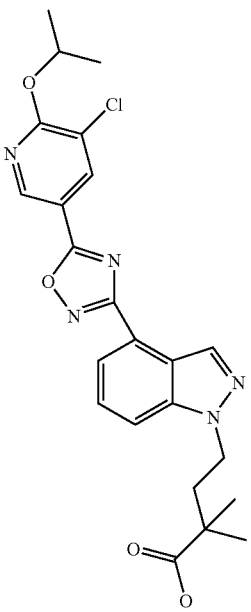 | 4-[4-(5-{5-Chloro-6-[(1-methylethyl)oxy]-3-pyridinyl}-1,2,4-oxadiazol-3-yl)-1H-indazol-1-yl]-2,2-dimethylbutanoic acid | D116 | [MH+] 470 |

S1P1 GTPγS Binding Assay

Rat Basophilic Leukaemia cells (RBL) stably expressing S1P1 receptor were grown to 80% confluency before being harvested into 10 ml Phospho-Buffered Saline (PBS) and centrifuged at 1200 rpm for 5 minutes. After removal of the supernatant, the pellet was re-suspended and homogenised in 20 volumes assay buffer (20 mM HEPES pH 7.4, 100 mM NaCl, 10 mM $MgCl_2.6H_2O$, 10 μM GDP Saponin 10 μg/ml). The membrane suspension was further centrifuged for 20 minutes at 20,000 rpm re-homogenised and spun again. Following the second centrifugation the pellet was resuspended in an appropriate volume (1 ml for each flask of cells) and assayed for protein concentration.

Concentrated stock of S1P was sonicated before serial dilutions were prepared from a starting concentration of $10^{-5}$ M. Diluted membranes (10 μg/well) were incubated with various concentrations of S1P and 0.3 nM $^{35}$S-GTPγS (NEN; specific activity 1250 Ci/mmol) in 96 deep well plates. Binding was performed at 30° C. for 45 minutes and terminated by harvesting the membranes onto GF/B filter plates using a Packard Universal Harvester. After drying the plates for 45 minutes, 50 μl of Microscint 0 was added to each well and binding measured on a Topcount NXT (Perkin Elmer). Data was analysed using Graphpad Prism 4 and expressed as percentage stimulation above basal. EC50 values were defined as the concentration of agonist required to give 50% of the maximal stimulation.

Example 1 of the invention had a pEC50>6 in this GTPγS binding assay.

S1P1 GTPγS Binding Assay (Alternative Method)

For membrane preparations all steps were performed at 4° C. Rat hepatoma cells stably expressing the human S1P1 receptor or Rat Basophilic Leukaemia cells (RBL) stably expressing human S1P3 receptor were grown to 80% confluency before being harvested into 10 ml Phospho-Buffered Saline (PBS) and centrifuged at 1200 rpm for 5 minutes. After removal of the supernatant, the pellet was re-suspended and cells were homogenised within a glass Waring blender for 2 bursts of 15 secs in 200 mls of buffer (50 mM HEPES, 1 mM leupeptin, 25 μg/ml bacitracin, 1 mM EDTA, 1 mM PMSF, 2 μM pepstatin A). The blender was plunged into ice for 5 mins after the first burst and 10-40 mins after the final burst to allow foam to dissipate. The material was then spun at 500 g for 20 mins and the supernatant spun for 36 mins at 48,000 g. The pellet was resuspended in the same buffer as above but without PMSF and pepstatin A. The material was then forced through a 0.6 mm needle, made up to the required volume, (usually ×4 the volume of the original cell pellet), aliquoted and stored frozen at −80° C.

Human S1P1 rat hepatoma membranes (1.5 μg/well) were adhered to a wheatgerm agglutinin (WGA)-coated scintillation proximity assay (SPA) beads (0.125 mg/well) in assay buffer (HEPES 20 mM, $MgCl_2$ 10 mM, NaCl 100 mM and pH adjusted to 7.4 using KOH 5M, GDP 10 μM FAC (final assay concentration) and saponin 90 μg/ml FAC was also added).

After 30 minutes pre-coupling on ice the bead and membrane suspension was dispensed into a white Greiner polypropylene LV384-well plate (5 μl/well), containing 0.1 μl of the compound. 5 μl/well [$^{35}$S]-GTPγS (0.5 nM final radioligand conc) made up in assay buffer was then added to agonist plates. The final assay cocktail (10.1 μl) was then centrifuged at 1000 rpm for 5 minutes then read immediately on a Viewlux reader.

All test compounds were dissolved in DMSO at a concentration of 10 mM and were prepared in 100% DMSO using a 1 in 4 dilution step to provide 11 point dose response curves. The dilutions were transferred to the assay plates ensuring that the DMSO concentration was constant across the plate for all assays. All data was normalized to the mean of 16 high and 16 low control wells on each plate. A four parameter curve fit was then applied.

Examples 1 to 52 of the invention had a pEC50>5 in this assay.

S1P3 GTPγS Binding Assay

S1P3 membranes from rat basophilic leukaemia cells (RBL-2H3)(1.5 µg/well) were adhered to WGA-coated SPA beads (0.125 mg/well) in assay buffer (HEPES 20 mM, MgCl$_2$ 3 mM, NaCl 100 mM and pH adjusted to 7.4 using KOH 5M), GDP 10 µM FAC and saponin 90 µg/ml FAC was also added).

After 30 minutes pre-coupling on ice the bead and membrane suspension was dispensed into a white Greiner polypropylene LV384-well plate (5 µl/well), containing 0.1 µl of the compound. 5 µl/well [$^{35}$S]-GTPγS (0.5 nM final radio-ligand conc) made up in assay buffer was then added to agonist plates. The final assay cocktail (10.1 µl) was centrifuged at 1000 rpm for 5 minutes then read immediately on a Viewlux reader.

All test compounds were dissolved in DMSO at a concentration of 10 mM and were prepared in 100% DMSO using a 1 in 4 dilution step to provide 11 point dose response curves. The dilutions were transferred to the assay plates ensuring that the DMSO concentration was constant across the plate for all assays.

All data was normalized to the mean of 16 high and 16 low control wells on each plate. A four parameter curve fit was then applied.

Examples 1 to 46 and 52 had a pEC50<6.5, many of the examples tested had a pEC50<5 in this assay.

Yeast Binding Assay

Yeast (*Saccharomyces cerevisiae*) cells expressing the human S1P1 receptor were generated by integration of an expression cassette into the ura3 chromosomal locus of yeast strain MMY23. This cassette consisted of DNA sequence encoding the human S1P1 receptor flanked by the yeast GPD promoter to the 5' end of S1P1 and a yeast transcriptional terminator sequence to the 3' end of S1P1. MMY23 expresses a yeast/mammalian chimeric G-protein alpha subunit in which the C-terminal 5 amino acids of Gpa1 are replaced with the C-terminal 5 amino acids of human Gαi1/2 (as described in Brown et al. (2000), *Yeast* 16:11-22). Cells were grown at 30° C. in liquid Synthetic Complete (SC) yeast media (Guthrie and Fink (1991), Methods in Enzymology, Vol. 194) lacking uracil, tryptophan, adenine and leucine to late logarithmic phase (approximately 6 OD$_{600}$/ml).

Agonists were prepared as 10 mM solutions in DMSO. EC$_{50}$ values (the concentration required to produce 50% maximal response) were estimated using 4 fold dilutions (BiomekFX, Beckman) into DMSO. Agonist solutions in DMSO (1% final assay volume) were transferred into black microtitre plates from Greiner (384-well). Cells were suspended at a density of 0.2 OD$_{600}$/ml in SC media lacking histidine, uracil, tryptophan, adenine and leucine and supplemented with 0.1 mM 3-aminotriazole, 0.1M sodium phosphate pH 7.0, and 10 µM fluorescein di-β-D-glucopyranoside (FDGlu). This mixture (50 ul per well) was added to agonist in the assay plates (Multidrop 384, Labsystems). After incubation at 30° C. for 24 hours, fluorescence resulting from degradation of FDGlu to fluorescein due to exoglucanase, an endogenous yeast enzyme produced during agonist-stimulated cell growth, was determined using a fluorescence microtitre plate reader (Tecan Spectrofluor or LJL Analyst excitation wavelength: 485 nm; emission wavelength: 535 nm). Fluorescence was plotted against compound concentration and iteratively curve fitted using a four parameter fit to generate a concentration effect value. Efficacy (E$_{max}$) was calculated from the equation $$E_{max}=Max_{[compound\ X]}-Min_{[compound\ X]}/Max_{[S1P]}-Min_{[S1P]}\times 100\%$$

where Max$_{[compound\ X]}$ and Min$_{[compound\ X]}$ are the fitted maximum and minimum respectively from the concentration effect curve for compound X, and Max$_{[S1P]}$ and Min$_{[S1P]}$ are the fitted maximum and minimum respectively from the concentration effect curve for Sphingosine-1-Phosphate (available from Sigma). Equieffective molar ratio (EMR) values were calculated from the equation $$EMR=EC_{50\ [compound\ X]}/EC_{50\ [S1P]}$$

Where EC$_{50\ [compound\ X]}$ is the EC$_{50}$ of compound X and EC$_{50\ [S1P]}$ is the EC$_{50}$ of S1P.

Exemplified compounds of the invention tested in this assay had a pEC50>5.

The invention claimed is:

1. A compound of formula (I) or salts thereof:

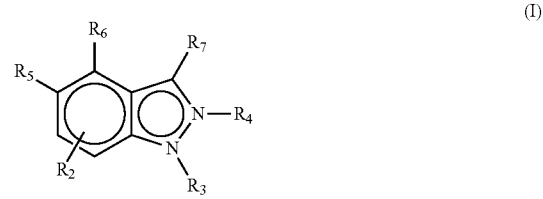

wherein
one of R$_5$ and R$_6$ is hydrogen and the other is (a):

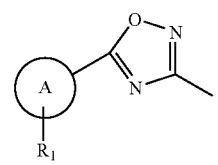

one of R$_3$ and R$_4$ is (b):

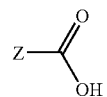

A is a phenyl or a 5 or 6-membered heteroaryl ring;
R$_1$ is hydrogen or up to three substituents independently selected from halogen, C$_{(1-4)}$alkyl, C$_{(1-4)}$alkoxy, C$_{(5-7)}$cycloalkyl, C$_{(5-7)}$cycloalkoxy, trifluoromethoxy, difluoromethoxy, trifluoromethyl, cyano, phenyl, 5 or 6 membered heteroaryl rings, piperidinyl and pyrrolidinyl;
R$_2$ is hydrogen or up to three substituents independently selected from halogen, C$_{(1-4)}$alkyl, C$_{(1-4)}$alkoxy, trifluoromethoxy, difluoromethoxy, trifluoromethyl and cyano;
R$_7$ is hydrogen or halogen;
Z is C$_{(1-4)}$alkyl may be optionally interrupted once by N or O and may be optionally substituted on carbon by up to four substituents independently selected from halogen, methyl and hydroxyl, with the proviso that no carbon atom is substituted by two hydroxyl groups.

2. A compound of claim 1 of formula (IA) or salts thereof,

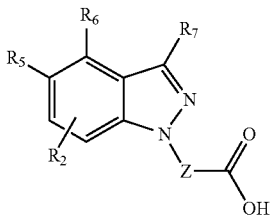
(IA)

wherein $R_1$, $R_2$, $R_5$, $R_6$, $R_7$ and Z are defined according to claim 1.

3. A compound of claim 1 of formula (IB) or salts thereof,

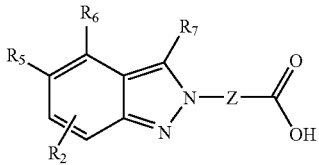
(IB)

wherein $R_1$, $R_2$, $R_5$, $R_6$, $R_7$ and Z are defined according to claim 1.

4. A compound according to claim 1 wherein:
A is optionally substituted thiophene, pyridyl or phenyl;
$R_1$ is two substituents independently selected from hydrogen, chloro, bromo, isopropoxy, propoxy, methoxy, 1-methylpropoxy, cyano, trifluoromethyl, trifluoromethoxy, cyclohexyl, piperidine, pyrrolidinyl, ethyl, 2-methylpropyl, phenyl and cyclopentoxy;
$R_2$ is hydrogen;
$R_7$ is hydrogen; and
Z is ethylene or propylene optionally substituted by gem-dimethyl.

5. A compound selected from:
3-[5-(5-{3-Chloro-4-[(1-methylethyl)oxy]phenyl}-1,2,4-oxadiazol-3-yl)-1H-indazol-1-yl]propanoic acid;
3-(5-{5-[3-Chloro-4-(ethyloxy)phenyl]-1,2,4-oxadiazol-3-yl}-1H-indazol-1-yl)propanoic acid;
3-[5-(5-{3-Cyano-4-[(1-methylethyl)oxy]phenyl}-1,2,4-oxadiazol-3-yl)-1H-indazol-1-yl]propanoic acid;
4-[5-(5-{3-Cyano-4-[(1-methylethyl)oxy]phenyl}-1,2,4-oxadiazol-3-yl)-1H-indazol-1-yl]butanoic acid;
3-(5-{5-[4-[(1-Methylethyl)oxy]-3-(trifluoromethyl)phenyl]-1,2,4-oxadiazol-3-yl}-1H-indazol-1-yl)propanoic acid;
4-[4-(5-{3-Chloro-4-[(1-methylethyl)oxy]phenyl}-1,2,4-oxadiazol-3-yl)-1H-indazol-1-yl]butanoic acid;
3-[4-(5-{3-Chloro-4-[(1-methylethyl)oxy]phenyl}-1,2,4-oxadiazol-3-yl)-1H-indazol-1-yl]propanoic acid;
3-(5-{5-[3-Chloro-4-(propyloxy)phenyl]-1,2,4-oxadiazol-3-yl}-1H-indazol-1-yl)propanoic acid;
3-[5-(5-{3-Chloro-4-[(trifluoromethyl)oxy]phenyl}-1,2,4-oxadiazol-3-yl)-1H-indazol-1-yl]propanoic acid;
3-(5-{5-[4-Cyclohexyl-3-(trifluoromethyl)phenyl]-1,2,4-oxadiazol-3-yl}-1H-indazol-1-yl)propanoic acid;
3-(5-{5-[4-(Methyloxy)-3-(trifluoromethyl)phenyl]-1,2,4-oxadiazol-3-yl}-1H-indazol-1-yl)propanoic acid;
[5-(5-{3-Cyano-4-[(1-methylethyl)oxy]phenyl}-1,2,4-oxadiazol-3-yl)-1H-indazol-1-yl]acetic acid;
3-(5-{5-[3-Chloro-4-(methyloxy)phenyl]-1,2,4-oxadiazol-3-yl}-1H-indazol-1-yl)propanoic acid;
3-(5-{5-[3-Ethyl-4-(1-piperidinyl)phenyl]-1,2,4-oxadiazol-3-yl}-1H-indazol-1-yl)propanoic acid;
3-{5-[5-(4-Cyclohexyl-3-ethylphenyl)-1,2,4-oxadiazol-3-yl]-1H-indazol-1-yl}propanoic acid;
3-(5-{5-[3-Cyano-4-(2-methylpropyl)phenyl]-1,2,4-oxadiazol-3-yl}-1H-indazol-1-yl)propanoic acid;
3-[5-(5-{3-Bromo-4-[(1-methylethyl)oxy]phenyl}-1,2,4-oxadiazol-3-yl)-1H-indazol-1-yl]propanoic acid;
3-(5-{5-[3-Chloro-4-(2-methylpropyl)phenyl]-1,2,4-oxadiazol-3-yl}-1H-indazol-1-yl)propanoic acid;
4-(5-{5-[4-[(1-Methylethyl)oxy]-3-(trifluoromethyl)phenyl]-1,2,4-oxadiazol-3-yl}-1H-indazol-1-yl)butanoic acid;
3-{5-[5-(2-Cyano-4-biphenylyl)-1,2,4-oxadiazol-3-yl]-1H-indazol-1-yl}propanoic acid;
3-(5-{5-[3-Chloro-4-(1-pyrrolidinyl)phenyl]-1,2,4-oxadiazol-3-yl}-1H-indazol-1-yl)propanoic acid;
4-[5-(5-{5-Chloro-6-[(1-methylethyl)oxy]-3-pyridinyl}-1,2,4-oxadiazol-3-yl)-1H-indazol-1-yl]butanoic acid hydrochloride;
4-[5-(5-{5-Chloro-6-[(1-methylethyl)oxy]-3-pyridinyl}-1,2,4-oxadiazol-3-yl)-2H-indazol-2-yl]butanoic acid hydrochloride;
4-(5-{5-[2-(Trifluoromethyl)-4-biphenylyl]-1,2,4-oxadiazol-3-yl}-1H-indazol-1-yl)butanoic acid;
4-(5-{5-[2-(Trifluoromethyl)-4-biphenylyl]-1,2,4-oxadiazol-3-yl}-2H-indazol-2-yl)butanoic acid;
3-[4-(5-{3-Cyano-4-[(1-methylethyl)oxy]phenyl}-1,2,4-oxadiazol-3-yl)-1H-indazol-1-yl]propanoic acid;
3-[4-(5-{3-Chloro-4-[(1-methylethyl)oxy]phenyl}-1,2,4-oxadiazol-3-yl)-2H-indazol-2-yl]propanoic acid;
4-[4-(5-{3-Cyano-4-[(1-methylethyl)oxy]phenyl}-1,2,4-oxadiazol-3-yl)-1H-indazol-1-yl]butanoic acid;
4-(4-{5-[3-Ethyl-4-(1-piperidinyl)phenyl]-1,2,4-oxadiazol-3-yl}-1H-indazol-1-yl)butanoic acid;
4-(4-{5-[2-(Trifluoromethyl)-4-biphenylyl]-1,2,4-oxadiazol-3-yl}-1H-indazol-1-yl)butanoic acid;
4-[4-(5-{3-Chloro-4-[(trifluoromethyl)oxy]phenyl}-1,2,4-oxadiazol-3-yl)-1H-indazol-1-yl]butanoic acid;
3-(4-{5-[4-[(1-Methylethyl)oxy]-3-(trifluoromethyl)phenyl]-1,2,4-oxadiazol-3-yl}-1H-indazol-1-yl)propanoic acid;
4-[4-(5-{5-Chloro-6-[(1-methylethyl)oxy]-3-pyridinyl}-1,2,4-oxadiazol-3-yl)-1H-indazol-1-yl]butanoic acid;
4-(4-{5-[4-Phenyl-5-(trifluoromethyl)-2-thienyl]-1,2,4-oxadiazol-3-yl}-1H-indazol-1-yl)butanoic acid;
4-[4-(5-{3-Chloro-4-[(1-methylethyl)oxy]phenyl}-1,2,4-oxadiazol-3-yl)-2H-indazol-2-yl]butanoic acid;
3-{5-[5-(3-Cyano-4-{[(1S)-1-methylpropyl]oxy}phenyl)-1,2,4-oxadiazol-3-yl]-1H-indazol-1-yl}propanoic acid sodium salt;
3-{5-[5-(3-Cyano-4-{[(1R)-1-methylpropyl]oxy}phenyl)-1,2,4-oxadiazol-3-yl]-1H-indazol-1-yl}propanoic acid sodium salt;
3-(5-{5-[3-Cyano-4-(cyclopentyloxy)phenyl]-1,2,4-oxadiazol-3-yl}-1H-indazol-1-yl)propanoic acid;
4-[5-(5-{3-Chloro-4-[(1-methylethyl)oxy]phenyl}-1,2,4-oxadiazol-3-yl)-1H-indazol-1-yl]butanoic acid;
4-(5-{5-[4-Phenyl-5-(trifluoromethyl)-2-thienyl]-1,2,4-oxadiazol-3-yl}-1H-indazol-1-yl)butanoic acid;
4-[5-(5-{3-Cyano-4-[(1-methylethyl)oxy]phenyl}-1,2,4-oxadiazol-3-yl)-2H-indazol-2-yl]butanoic acid;
3-[5-(5-{3-Chloro-4-[(1-methylethyl)oxy]phenyl}-1,2,4-oxadiazol-3-yl)-1H-indazol-1-yl]-2,2-dimethylpropanoic acid;

3-[5-(5-{3-Chloro-4-[(1-methylethyl)oxy]phenyl}-1,2,4-oxadiazol-3-yl)-2H-indazol-2-yl]-2,2-dimethylpropanoic acid;

3-[4-(5-{3-Chloro-4-[(1-methylethyl)oxy]phenyl}-1,2,4-oxadiazol-3-yl)-1H-indazol-1-yl]-2,2-dimethylpropanoic acid;

3-[4-(5-{5-Chloro-6-[(1-methylethyl)oxy]-3-pyridinyl}-1,2,4-oxadiazol-3-yl)-1H-indazol-1-yl]-2,2-dimethylpropanoic acid;

3-[5-(5-{3-Cyano-4-[(1-methylethyl)oxy]phenyl}-1,2,4-oxadiazol-3-yl)-1H-indazol-1-yl]-2,2-dimethylpropanoic acid;

4-[5-(5-{3-Cyano-4-[(1-methylethyl)oxy]phenyl}-1,2,4-oxadiazol-3-yl)-1H-indazol-1-yl]-2,2-dimethylbutanoic acid;

3-[4-(5-{3-Cyano-4-[(1-methylethyl)oxy]phenyl}-1,2,4-oxadiazol-3-yl)-1H-indazol-1-yl]-2,2-dimethylpropanoic acid;

3-[5-(5-{5-Chloro-6-[(1-methylethyl)oxy]-3-pyridinyl}-1,2,4-oxadiazol-3-yl)-1H-indazol-1-yl]-2,2-dimethylpropanoic acid;

4-[4-(5-{3-Cyano-4-[(1-methylethyl)oxy]phenyl}-1,2,4-oxadiazol-3-yl)-1H-indazol-1-yl]-2,2-dimethylbutanoic acid; and 4-[4-(5-{5-Chloro-6-[(1-methylethyl)oxy]-3-pyridinyl}-1,2,4-oxadiazol-3-yl)-1H-indazol-1-yl]-2,2-dimethylbutanoic acid;

or salts thereof.

6. A pharmaceutical composition comprising a compound according to claim 1 and one or more pharmaceutically-acceptable excipients.

7. A method of treating multiple sclerosis, comprising administering a safe and effective amount of a compound or salt according to claim 1 to a patient in need thereof.

* * * * *